United States Patent
Lamarque et al.

(10) Patent No.: US 12,398,158 B2
(45) Date of Patent: Aug. 26, 2025

(54) FLUORESCENT GTP ANALOGUES AND USE

(71) Applicant: CISBIO BIOASSAYS, Codolet (FR)

(72) Inventors: Laurent Lamarque, Saint-Victor la Coste (FR); Emmanuel Bourrier, Bagnols-sur-Ceze (FR); Thomas Roux, Nimes (FR); Eric Trinquet, Pont-Saint-Esprit (FR); Elodie Dupuis, Caissargues (FR)

(73) Assignee: CISBIO BIOASSAYS, Codolet (FR)

( * ) Notice: Subject to any disclaimer, the term of this patent is extended or adjusted under 35 U.S.C. 154(b) by 922 days.

(21) Appl. No.: 17/427,200

(22) PCT Filed: Jan. 30, 2020

(86) PCT No.: PCT/FR2020/050149
§ 371 (c)(1),
(2) Date: Jul. 30, 2021

(87) PCT Pub. No.: WO2020/157439
PCT Pub. Date: Aug. 6, 2020

(65) Prior Publication Data
US 2022/0144860 A1 May 12, 2022

(30) Foreign Application Priority Data

Jan. 30, 2019 (FR) ...................................... 1900856

(51) Int. Cl.
*C07F 5/00* (2006.01)
(52) U.S. Cl.
CPC ...................... *C07F 5/00* (2013.01)
(58) Field of Classification Search
CPC .... C07H 23/00; G01N 33/20; C09K 11/7728; C09K 11/7743
See application file for complete search history.

(56) References Cited

U.S. PATENT DOCUMENTS

2007/0287162 A1 12/2007 Briggs et al.
2023/0091315 A1* 3/2023 Dupuis .............. G01N 33/5735
530/387.1

FOREIGN PATENT DOCUMENTS

| WO | 2003008435 A2 | 1/2003 | |
|---|---|---|---|
| WO | 2006035208 A1 | 4/2006 | |
| WO | WO-2006035207 A2 * | 4/2006 | ............. C07H 19/10 |
| WO | 2006086883 A1 | 8/2006 | |
| WO | WO-2008063721 A2 * | 5/2008 | ............ G01N 33/582 |
| WO | WO-2009068751 A1 * | 6/2009 | ............ G01N 33/542 |

OTHER PUBLICATIONS

C. Spangler et al., 394 Analytical and Bioanalytical Chemistry, 989-996 (2009) (Year: 2009).*
CAS Abstract and Indexed Compounds J. Vuojola et al., 81 Analytical Chemistry, 5033-5038 (2009) (Year: 2009).*
J. Vuojola et al., 81 Analytical Chemistry, 5033-5038 (2009) (Year: 2009).*
D. Geißler et al., 1 Current Inorganic Chemistry, 17-35 (2011) (Year: 2011).*
Q. Wang et al., 52 Inorganic Chemistry, 8461-8456 (2013) (Year: 2013).*
Takalo, 5 Bioconjugate Chemistry, 278-282 (1994) (Year: 1994).*
Z. Izadi et al., 182 Biomaterials, 191-201 (2018) (Year: 2018).*
Bünemann, et al., Gi protein activation in intact cells involves subunit rearrangement rather than dissociation, Proceedings of the National Academy of Sciences, vol. 100, No. 26, 2003, pp. 16077-16082.
Bünzli, Lanthanide Luminescence for Biomedical Analyses and Imaging, American Chemical Society, vol. 110, No. 5, 2010, pp. 2729-2755.
Faulkner, et al., Lanthanide Complexes for Luminescence Imaging Applications, Applied Spectroscopy Review, vol. 40, 2005, pp. 1-31.
Heffern, et al., Lanthanide Probes for Bioresponsive Imaging, Chemical Reviews, vol. 114, No. 8, 2014, pp. 1-122.
Hemmilä, et al., Novel detection strategies for drug discovery, www.drugdiscoverytoday.com, vol. 7, No. 18, 2002, pp. S150-S156.
International Search Report and Written Opinion from PCT/FR2020/050149 dated Mar. 30, 2020, 13 pages.
Mathis, Probing molecular interactions with homogeneous techniques based on rare earth cryptates and fluorescence energy transfer, Clinical Chemistry, vol. 41, No. 9, 1995, pp. 1391-1397.
Van Lode, et al., A Europium Chelate for Quantitative Point-of-Care Immunoassays Using Direct Surface Measurement, Analytical Chemistry, vol. 75, No. 13, 2003, pp. 3193-3201.
Vuojola, et al., Resonance Energy Transfer from Lanthanide Chelates to Overlapping and Nonoverlapping Fluorescent Protein Acceptors, Analytical Chemistry, vol. 81, No. 12, 2009, pp. 5033-5038.
Wang, et al., Stable and Highly Fluorescent Europium(III) Chelates for Time-Resolved Immunoassays, Inorganic Chemistry, vol. 52, No. 15, 2013, pp. 8461-8466.
Wei, et al., Advances in luminescent lanthanide complexes and applications, Science China Technological Sciences, vol. 61, No. 9, 2018, pp. 1265-1285.

(Continued)

*Primary Examiner* — Alexander R Pagano
(74) *Attorney, Agent, or Firm* — Calfee, Halter & Griswold LLP

(57) ABSTRACT

The invention relates to compounds of formula:

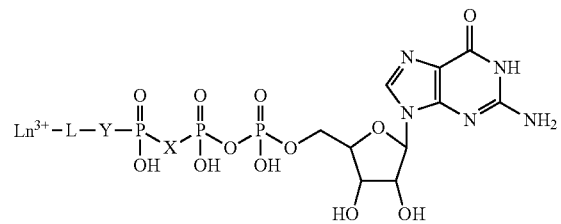

in which X, Y, L and $Ln^{3+}$ are as defined in the description.

1 Claim, 6 Drawing Sheets

(56) References Cited

OTHER PUBLICATIONS

Xu, et al., A bioluminescence resonance energy transfer (BRET) system: Application to interacting circadian clock proteins, Proceedings of the National Academy of Sciences, vol. 96, 1999, pp. 151-156.
Yuan, et al., Lanthanide Complex-Based Fluorescence Label for Time-Resolved Fluorescence Bioassay, Journal of Fluorescence, vol. 15, No. 4, 2005, pp. 559-568.
Zhang et al., Tools for GPCR Drug Discovery, Acta Pharmacologica Sinica, vol. 33, 2012, pp. 372-384.

* cited by examiner

Non-Specific Signal (Excess unlabeled GTPgS)
Total signal

Non-Specific Signal (Excess unlabeled GTPgS)
Total signal

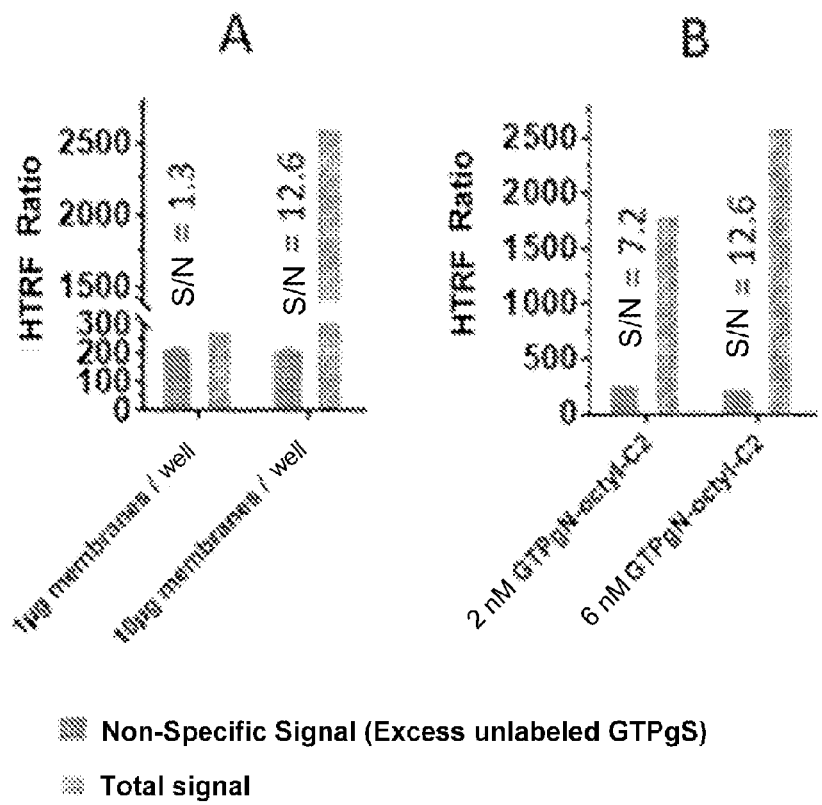
▓ Non-Specific Signal (Excess unlabeled GTPgS)
▓ Total signal
Fig.11A-11B
GTPgN-octyl-thiosuccinimidyl C2    Ab DSV36S-d2
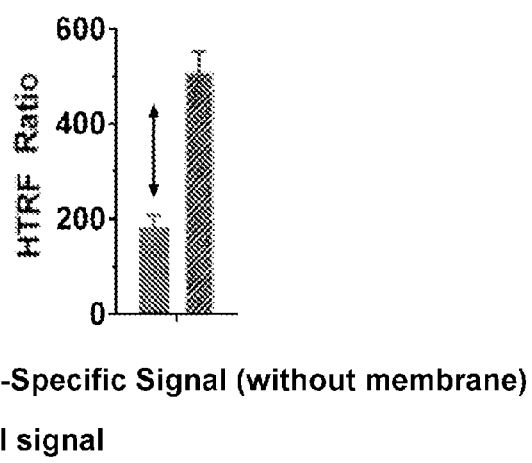
▓ Non-Specific Signal (without membrane)
▓ Total signal
Fig.12

FLUORESCENT GTP ANALOGUES AND USE

This application is the U.S. national stage entry of PCT/FR2020/050149, filed on Jan. 30, 2020, which claims priority to and all benefit of French Patent Application Serial No. 1900856, filed on Jan. 30, 2019, the entire disclosures of which are fully incorporated herein by reference.

FIELD OF THE INVENTION

The present invention relates to fluorescent GTP analogs useful for detecting, by energy transfer techniques, molecules capable of modulating the activation of a G protein-coupled receptor.

STATE OF THE ART

G protein-coupled receptors (GPCRs) are a family of membrane receptors in mammals and throughout the animal kingdom. G proteins are heterotrimeric proteins (3 subunits: alpha, beta and gamma) which are activated by GPCRs. Through the GPCRs, the G proteins have a role of transducing a signal from outside the cell to the inside of the cell (i.e. cellular response to an external stimulus). Their commonly described mechanism of action is presented in FIG. 1 and summarized below:

in its inactive, resting, state, the alpha subunit of the G protein is bound to the nucleotide GDP (full GDP-bound G protein);

after activation of the GPCR, the latter binds to the alpha subunit of the G protein and initiates a process of activation of the G protein consisting of two stages:

1) the departure of the GDP from the G protein to give an empty G protein, and the formation of an inactive GPCR/empty G protein complex, and
2) the binding of GTP which results in the formation of an active G protein, in GTP form (full GTP-bound G protein). In the first stage, the G protein bound to the receptor is in a form called "empty form". This state is described in the literature as being transient since it is described that the nucleotide GTP binds rapidly to the alpha subunit of the G protein. In addition, the beta/gamma subunits of the activated G protein dissociate from the alpha subunit;

the alpha subunit of the full GTP-bound G protein then binds to the effectors in order to activate them. The effectors in their turn activate signaling pathways resulting in a cellular response;

the GTP is subsequently hydrolyzed to give GDP by the alpha subunit of the G protein and the alpha subunit reassociates with the beta/gamma subunits to reform the full GDP-bound G protein (inactive state).

There exist several subtypes of G alpha proteins exhibiting different selectivity profiles for the different effectors (Journal of Molecular Biology, 2016, 428, 3850) and thus bringing about the activation of preferential signaling pathways.

GPCRs are associated with many important physiological functions and are considered to be one of the favored therapeutic targets for a large number of pathologies. Thus, many in vitro screening tests have been developed in order to identify molecules capable of modulating GPCRs. The tests developed make use of different mechanisms for the activation of G proteins and employ varied technologies (Zhang et al.; Tools for GPCR Drug Discovery; Acta Pharmacologica Sinica, 2012, 33, 372). Mention may in particular be made of affinity tests which use radiolabeled ligands to measure the affinity of the ligand for GPCR, proximity scintigraphy tests which use scintigraphy beads to which GPCRs have been attached or functional tests using weakly or non-hydrolyzable GTP, such as GTPγS (GTP-gamma-S). These tests are nevertheless difficult to carry out and sometimes require membrane filtration stages which can limit their use as high-throughput screening (HTS) tests. Other tests have been developed to demonstrate the activation of GPCRs. These tests are based in particular on energy transfer techniques (RET—Resonance Energy Transfer), such as FRET (Fluorescence Resonance Energy Transfer)—see Clinical Chemistry, 1995, 41, 1391—or BRET (Bioluminescence Resonance Energy Transfer)—see Proceedings of the National Academy of Sciences, 1999, 96 (1), 151.

These two techniques involve notions of molecules capable of giving energy (referred to as donors) or of accepting energy (referred to as acceptors)—see Physical Chemistry Chemical Physics, 2007, 9, 5847. Mention may be made, for example, of the energy transfer techniques demonstrating the interaction between a GPCR and the G protein by using either a donor conjugated to the GPCR and an acceptor conjugated to the G protein (WO 2006/086883 and WO 2003/008435) or an acceptor conjugated to the alpha subunit of the G protein and a donor conjugated to the beta and/or gamma subunit of the G protein (Bunemann et al., Proceedings of the National Academy of Sciences, 2003, 26, 16077). These techniques are nevertheless restrictive since they require the preparation of fusion proteins and they do not make it possible to study the GPCRs and the G proteins expressed endogenously by the cells (i.e. unmodified and not overexpressed). On the other hand, in order to discriminate between the different subtypes of G alpha proteins which can be activated by the receptor, these techniques require the preparation of multiple membrane samples (a specific preparation for each subtype of G alpha protein). Energy transfer techniques have also been used for the development of tests targeted at visualizing the modulation of the GTP (active) form of the G protein or of the GDP (inactive) form of the G protein. Mention may be made, for example, of the applications WO 2006/035208 and US 2007/0287162, in which a GTP analog coupled to a cyanine-type molecule is employed.

Application WO 2009/068751 describes a method in which an energy transfer signal is detected using labeled ATP derivatives; these derivatives cannot, however, bind to the G protein. A GTP analog is described in the journal Drug Discovery Today, 2002, 7 (18), S150), as capable of being used in a time-resolved fluorescence detection technique. This analog consists of a europium chelate coupled to the phosphate atom in the gamma position of GTP via a nitrogen atom. The structure of the europium chelate, however, is not disclosed, no more than the method used to synthesize the analog in question. Another GTP analog is described in Analytical Chemistry, 2009, 81, 5033, which results from the coupling of gamma-[(8-aminooctyl)imido]guanosine-5'-triphosphate and {2,2',2",2'''-{[[2-(4-isothiocyanatophenyl)ethyl]imino]bis(methylene)bis{4-{[4-(R-D-glucopyranoxy)phenyl]ethynyl}pyridine-6,2-diyl}bis(methylenenitrilo)}tetrakis(acetato)}europium(III), the synthesis of which has been described in Analytical Chemistry, 2003, 75, 3193.

There thus exists a real need to have available compounds capable of binding to the G protein and which can de facto be used in a method for the detection, by energy transfer techniques, of molecules capable of modulating the activation of a G protein-coupled receptor.

SUMMARY OF THE INVENTION

An object of the present invention is the provision of new molecules of GTP or derivatives thereof, which are coupled to lanthanide complexes and which are represented by the general formula (I):

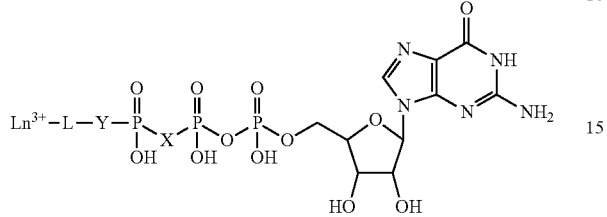

(I)

in which:
X=O, NH or CH$_2$;
Y=O, NH or CH$_2$;
L is a divalent linking group;
Ln$^{3+}$ is a lanthanide complex which can optionally carry a reactive group G$_3$ (as defined below);
it being understood that, when X represents NH and L-Y represents an octylamino group, then Ln$^{3+}$ is not {2,2',2",2"'-{[[2-(4-isothiocyanatophenyl)ethyl]imino]bis(methylene)bis{4-{[4-(R-D-glucopyranoxy)phenyl]ethynyl}pyridine-6,2-diyl}bis(methylenenitrilo)} tetrakis (acetato)}europium(III).

BRIEF DESCRIPTION OF THE DRAWINGS

FIGS. 11A and 11B illustrate the effect of the concentration of membranes and of test compound on the binding of said compound to the Gαi protein.

FIG. 12 illustrates a test for binding a compound of the invention to the Gαi protein.

DESCRIPTION OF THE INVENTION

Figure 1:
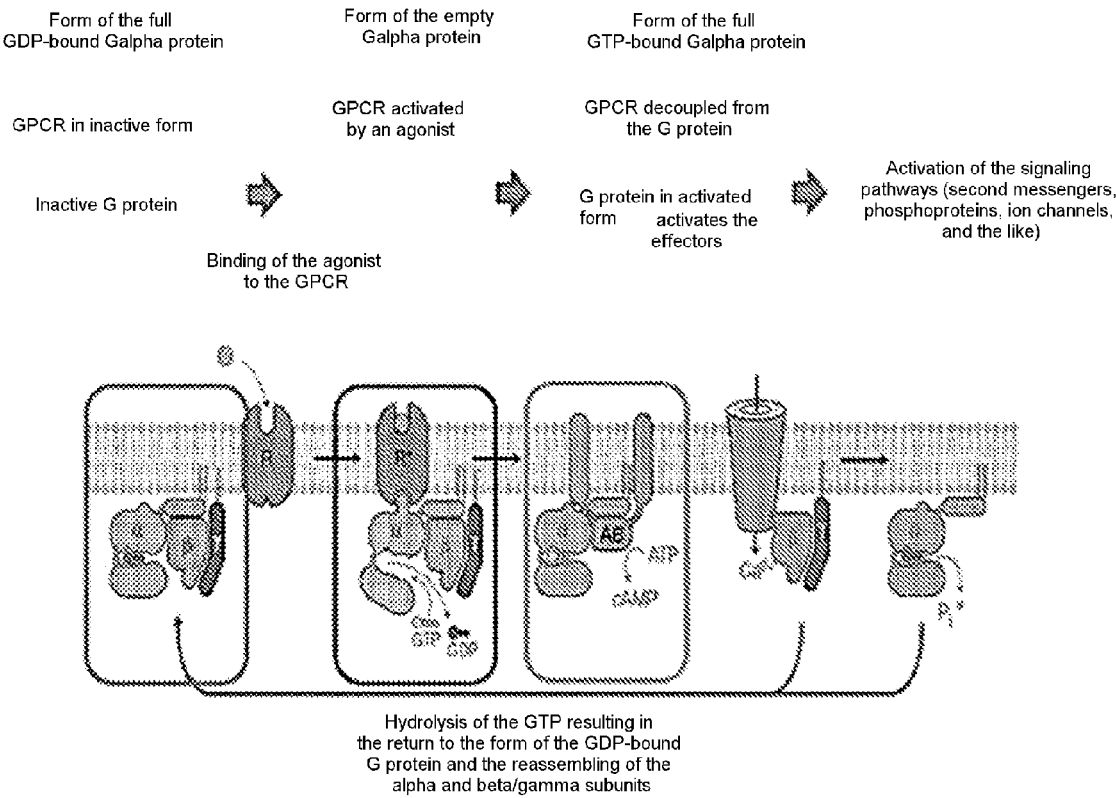
FIG. 1 illustrates the mechanism of action of G proteins.

According to one aspect, the present invention relates to compounds of formula (I):

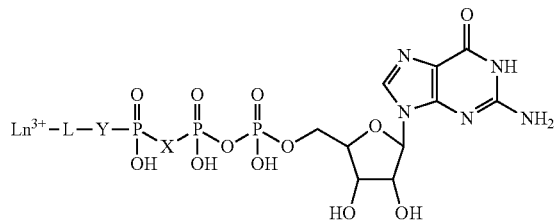

(I)

in which:
X=O, NH or CH$_2$;
Y=O, NH or CH$_2$;
L is a divalent linking group;
Ln$^{3+}$ is a lanthanide complex which can optionally carry a reactive group G$_3$ (as defined below);
provided that, when X represents NH and L-Y represents an octylamino group, then Ln$^{3+}$ is not {2,2',2",2"'-{[[2-(4-isothiocyanatophenyl)ethyl]imino]bis(methylene)bis{4-{[4-(R-D-glucopyranoxy)phenyl]ethynyl}pyridine-6,2-diyl}bis(methylenenitrilo)} tetrakis (acetato)}europium(III).

The term "lanthanide complex" is understood to mean a chelate, a macrocycle, a cryptate or any organic entity capable of complexing an atom of the lanthanide family, the lanthanide (Ln) being chosen from: Eu, Sm, Tb, Gd, Dy, Nd or Er; preferably, the lanthanide is Tb, Sm or Eu and more preferably still Eu or Tb.

The families of the various compounds of formula (I) are represented by the formulae (Ia) to (Ig):

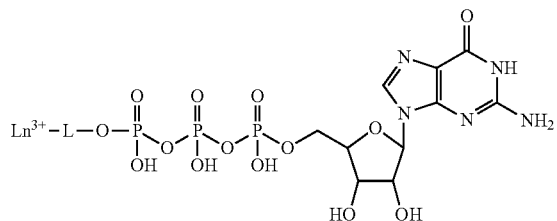

(Ia)

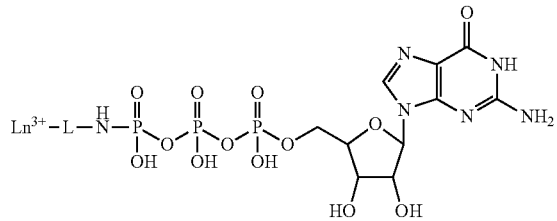

(Ib)

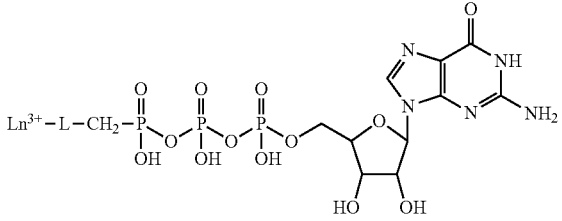

(Ic)

(Id)

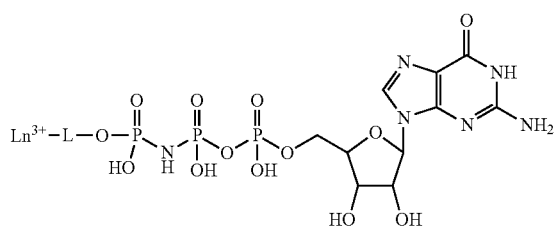

(Ie)

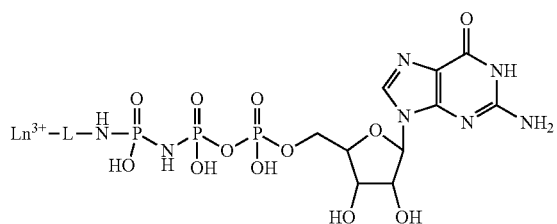

(If)

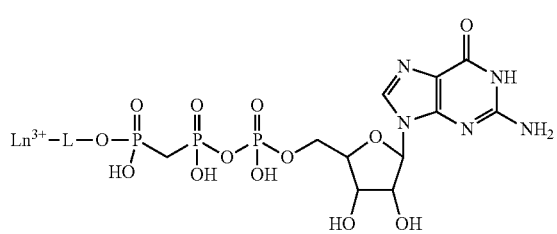

(Ig)

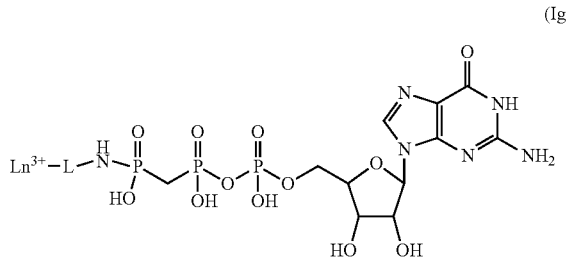

in which L and Ln³⁺ have the meanings indicated above.

A first family of compounds according to the invention consists of the compounds of formulae (Ia), (Id) and (If). This family is called the GTP-gamma-O family (because the divalent linking group is bonded to the phosphate in the gamma position of the GTP via an oxygen atom). A second family of compounds according to the invention consists of the compounds of formulae (Ib), (Ie) and (Ig). This family is called the GTP-gamma-N family (because the divalent linking group is bonded to the phosphate in the gamma position of the GTP via a nitrogen atom). A third family of compounds according to the invention consists of the compounds of formula (Ic). This family is called the GTP-gamma-C family (because the divalent linking group is bonded to the phosphate in the gamma position of the GTP via a carbon atom).

In one embodiment, X is O. In another embodiment, X is NH. In another embodiment, X is CH$_2$.

In one embodiment, the divalent linking group L is chosen from:
- a direct link;
- a linear or branched C$_1$-C$_{20}$, preferably C$_1$-C$_8$, alkylene group, optionally containing one or more double or triple bonds;
- a C$_5$-C$_8$ cycloalkylene group; or
- a C$_6$-C$_{14}$ arylene group;

said alkylene, cycloalkylene or arylene groups optionally containing one or more heteroatoms, such as oxygen, nitrogen, sulfur or phosphorus, or one or more carbamoyl or carboxamido group(s), and said alkylene, cycloalkylene or arylene groups optionally being substituted by 1 to 5, preferably 1 to 3, C$_1$-C$_8$ alkyl, C$_6$-C$_{14}$ aryl, sulfonate or oxo groups.

The divalent linking group L is advantageously chosen from the following groups:

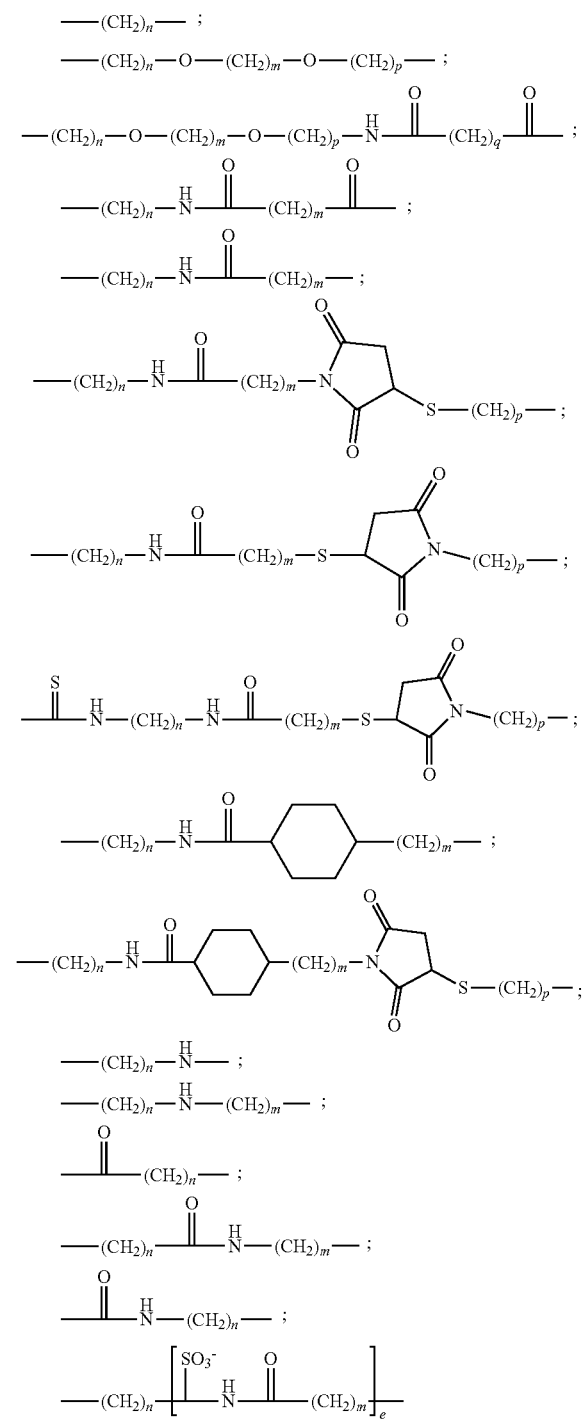

in which n, m, p and q are integers from 1 to 16, preferably from 1 to 5, and e is an integer ranging from 1 to 6, preferably from 1 to 4.

In a particularly advantageous way, the divalent linking group L is chosen from a direct link, a linear or branched $C_1$-$C_8$ alkylene group or a group of formula:

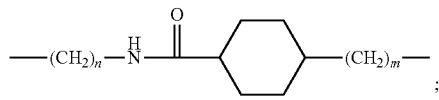

The divalent linking group L is preferably chosen from:

-continued

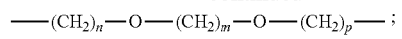

the —$(CH_2)_n$— group being very particularly preferred.

According to another embodiment, the divalent linking group L is a group of formula:

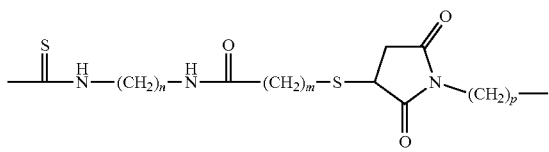

in which m, n and p are integers from 1 to 16, preferably from 1 to 5.

In one embodiment, the lanthanide complex $Ln^{3+}$ is chosen from one of the complexes below:

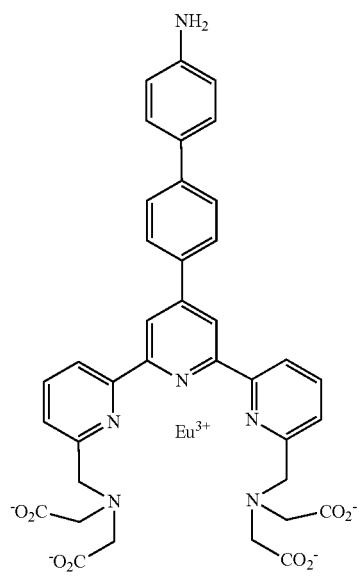

C1

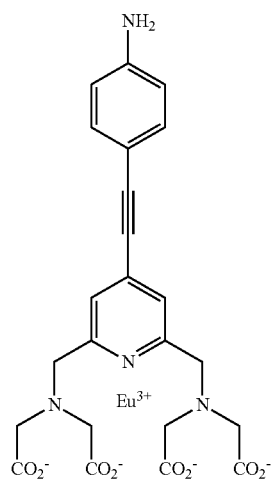

C2

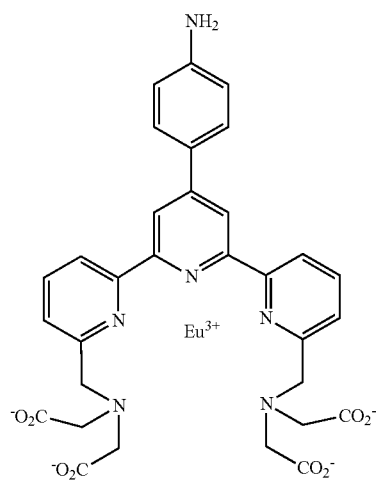

C3

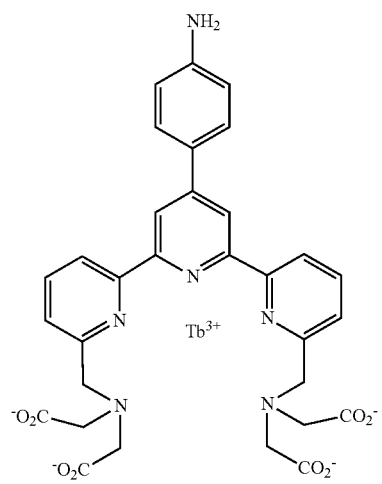

C4

-continued
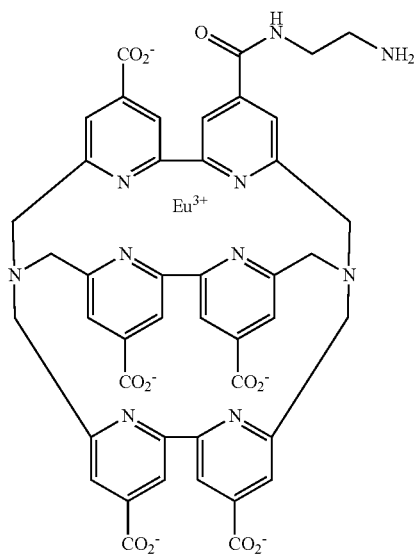
C5
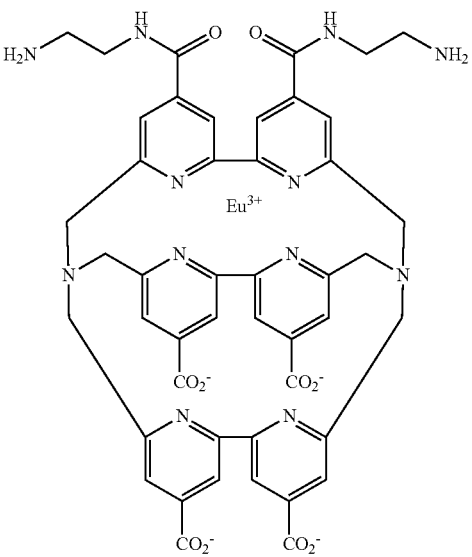
C6
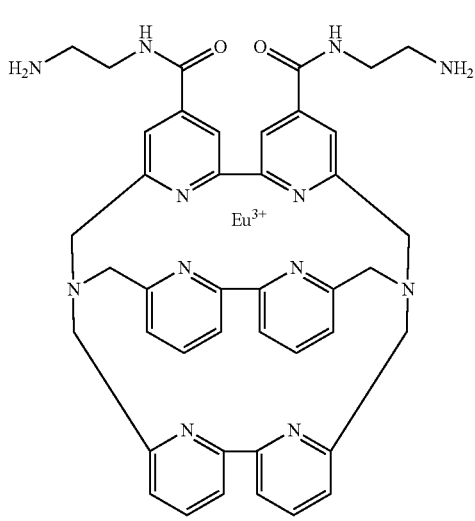
C7
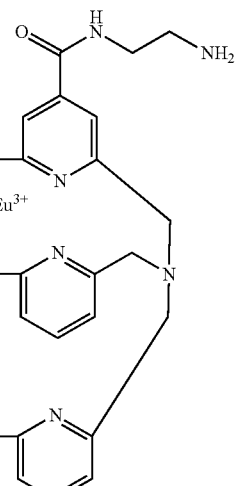
C8
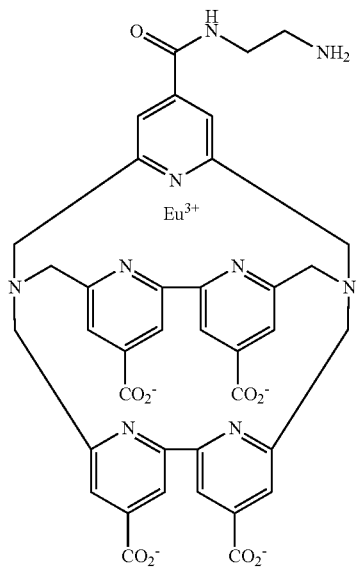
C9
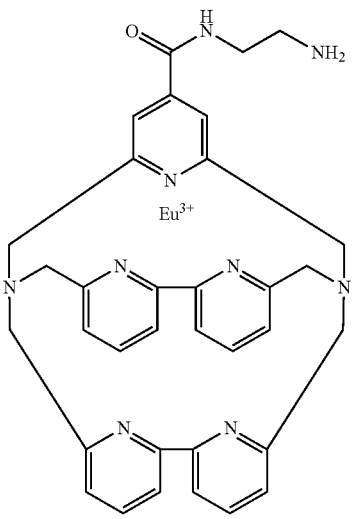
C10

-continued
C11
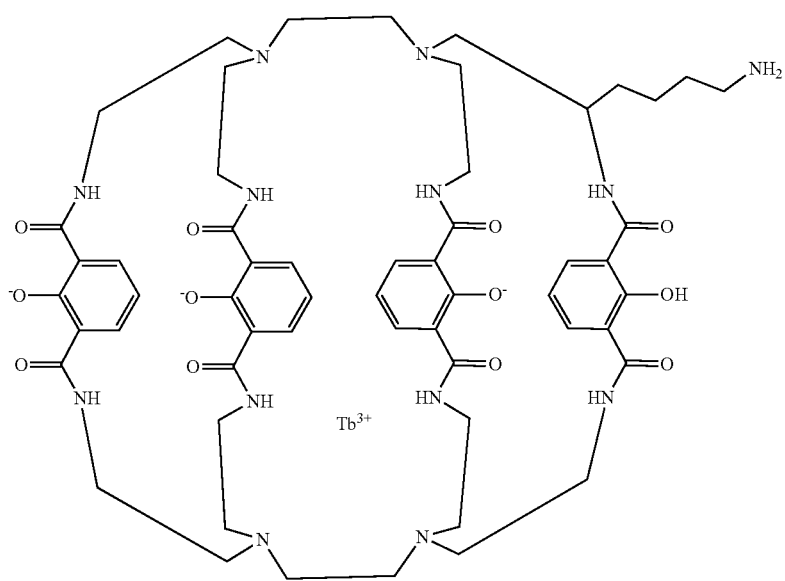
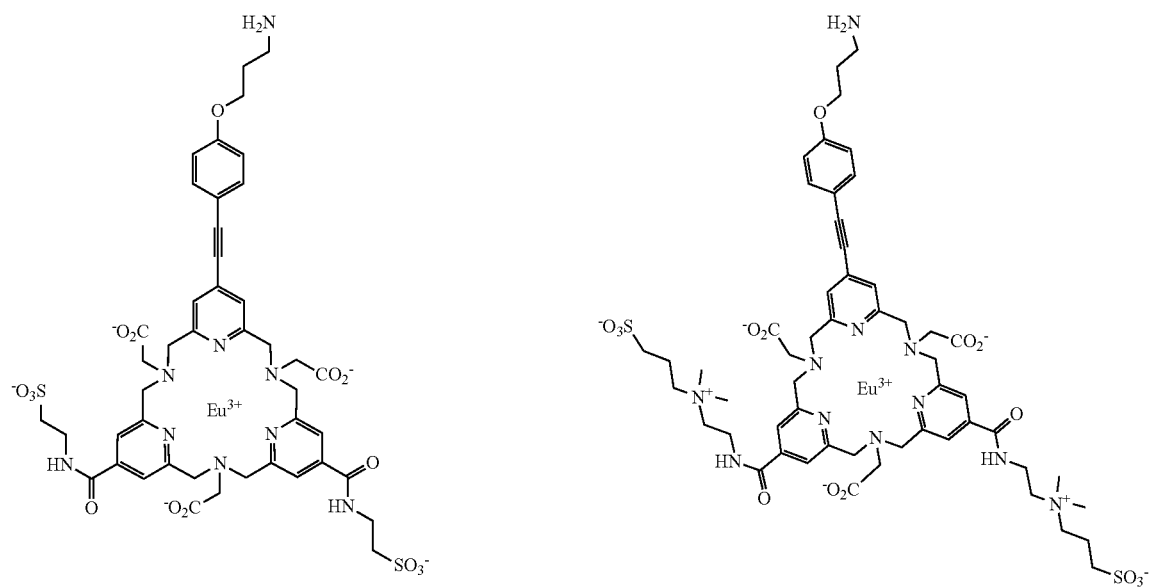

-continued
13
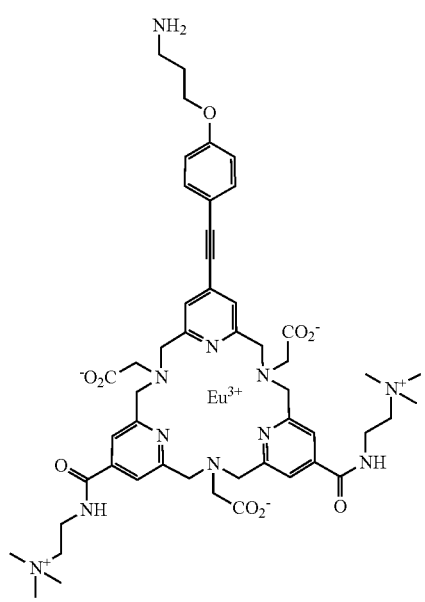
14
C14
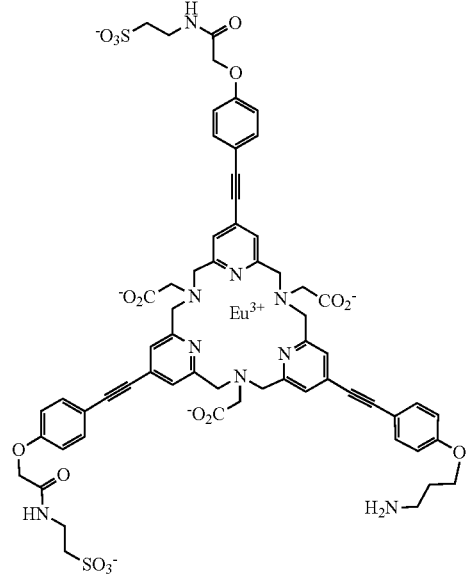
C15
C16
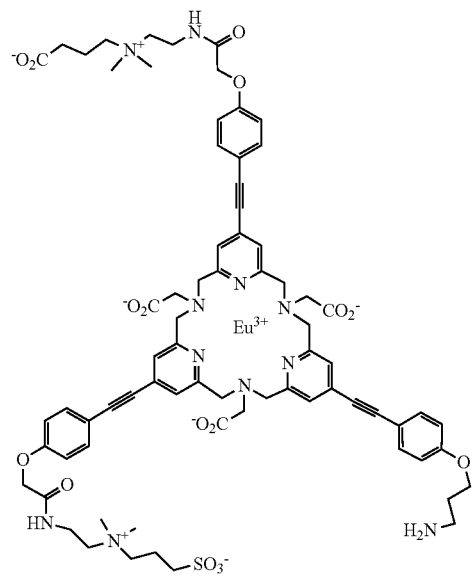
C17
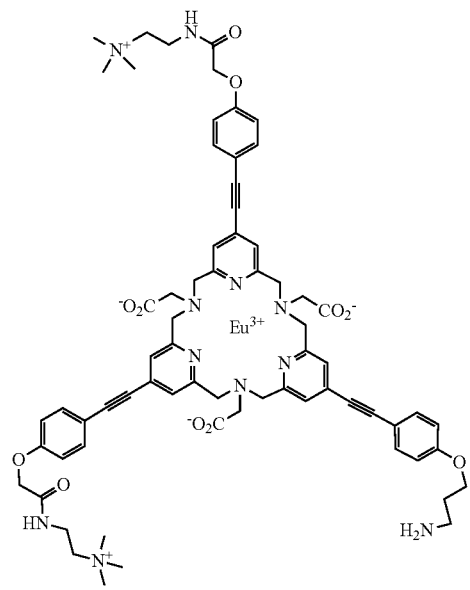

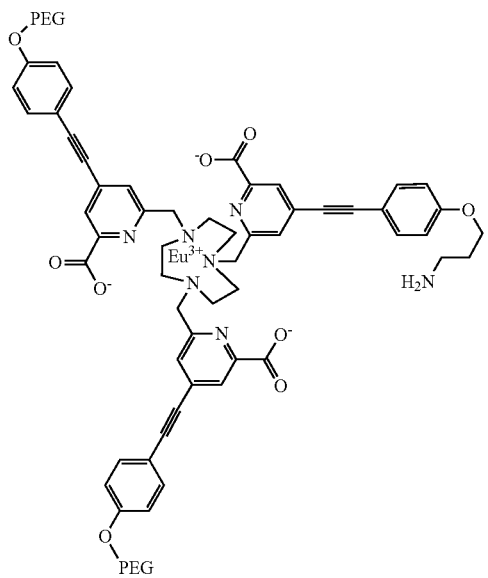
C18
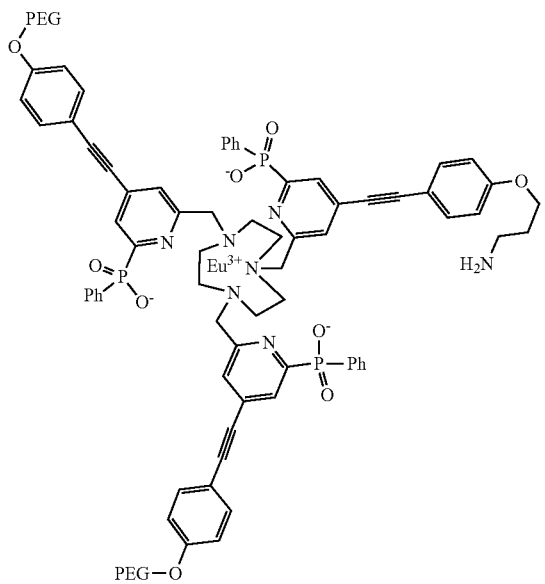
C19
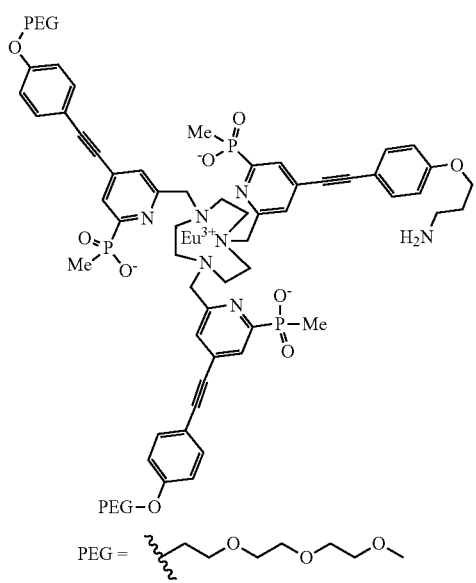
C20
PEG = $\sim\!\!\sim\!\!\sim\!\!\text{O}\frown\text{O}\frown\text{O}\frown$

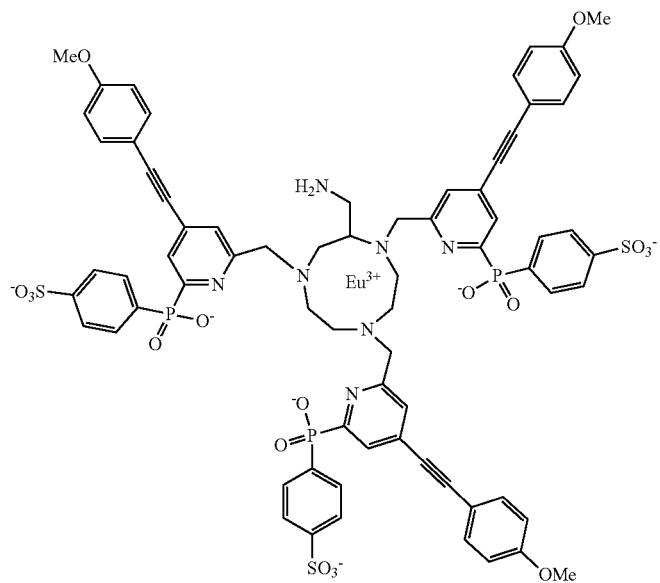
C21
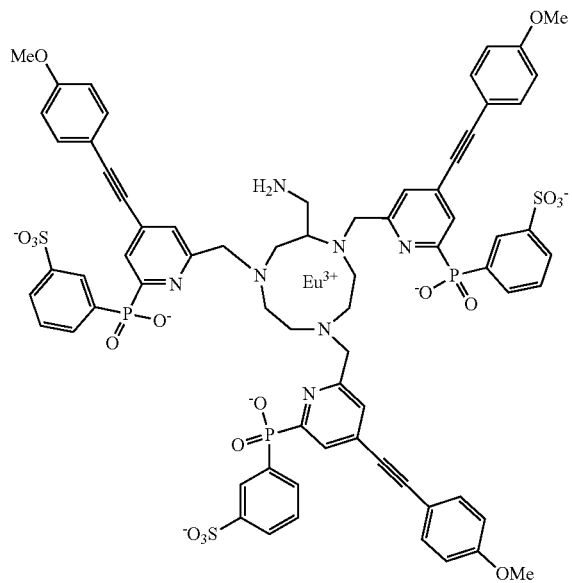
C22

C23
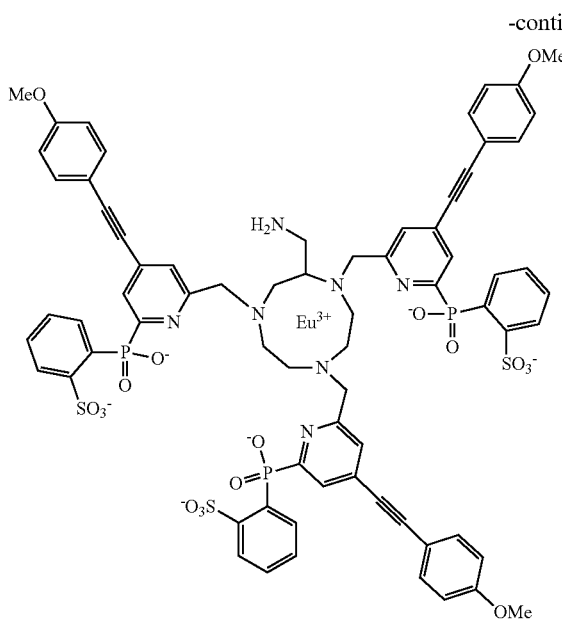
C24
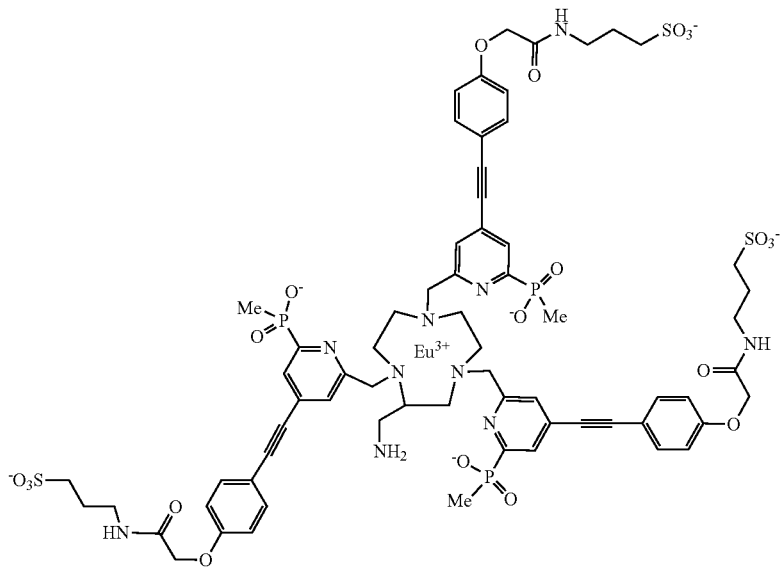

C25
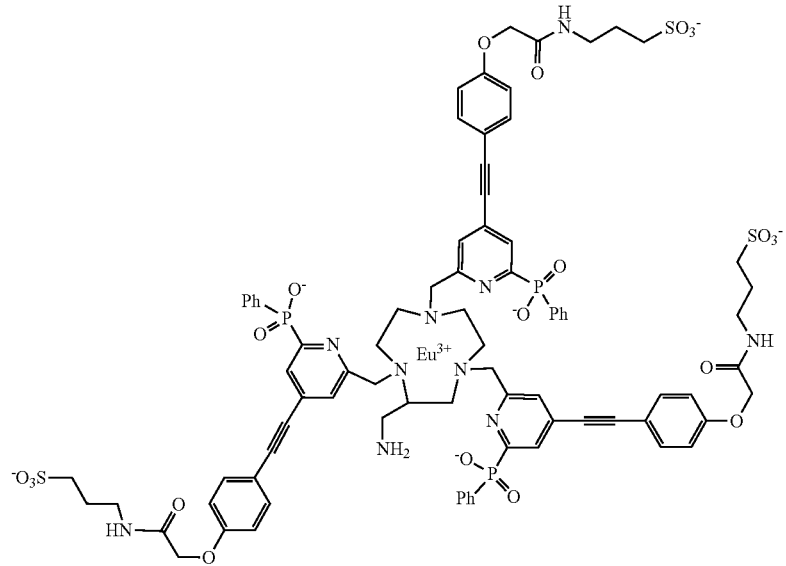
C26
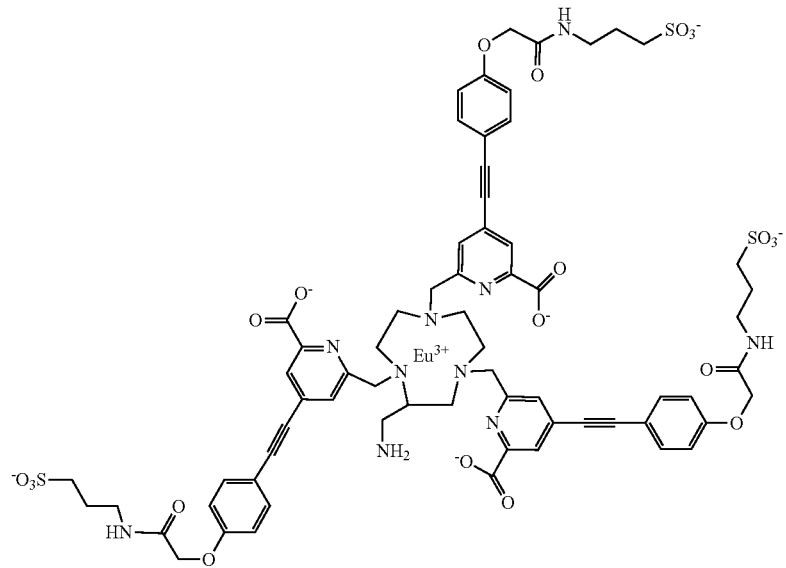

-continued
C27
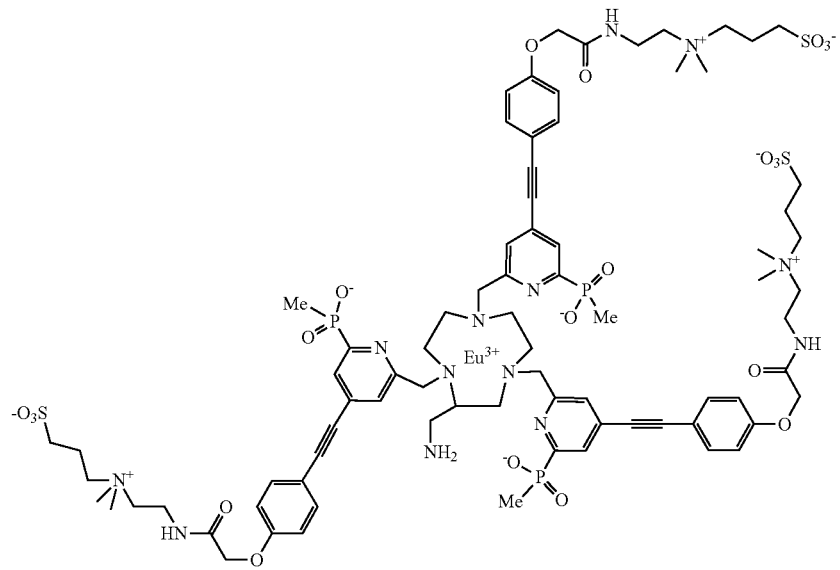
C28
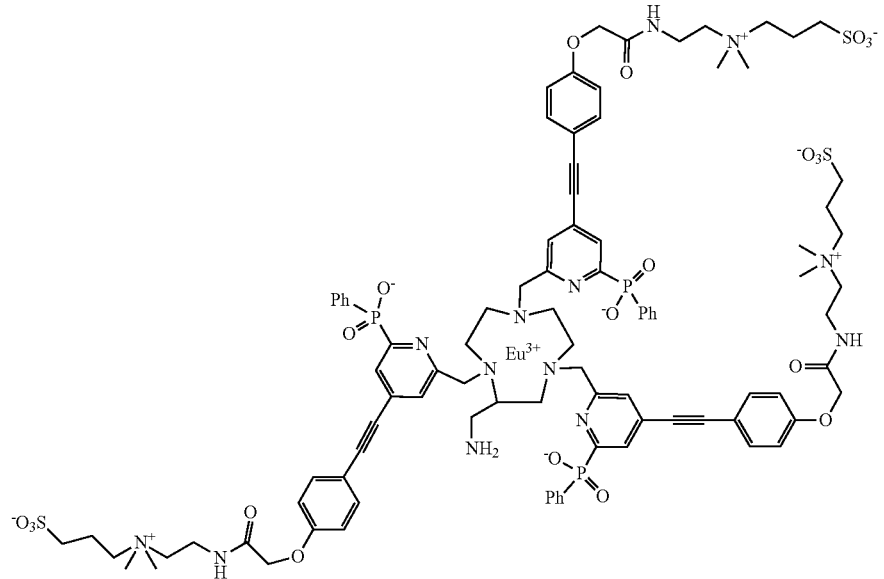

C29
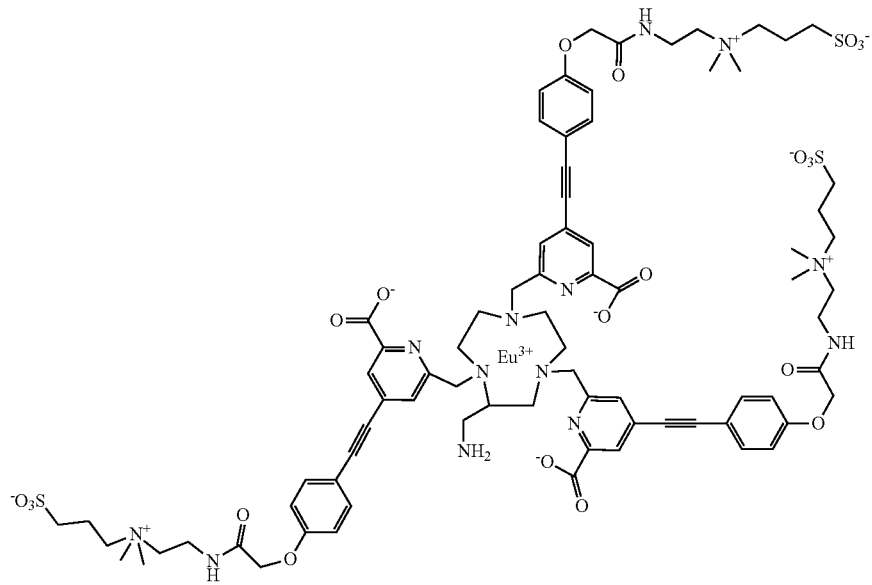
C30
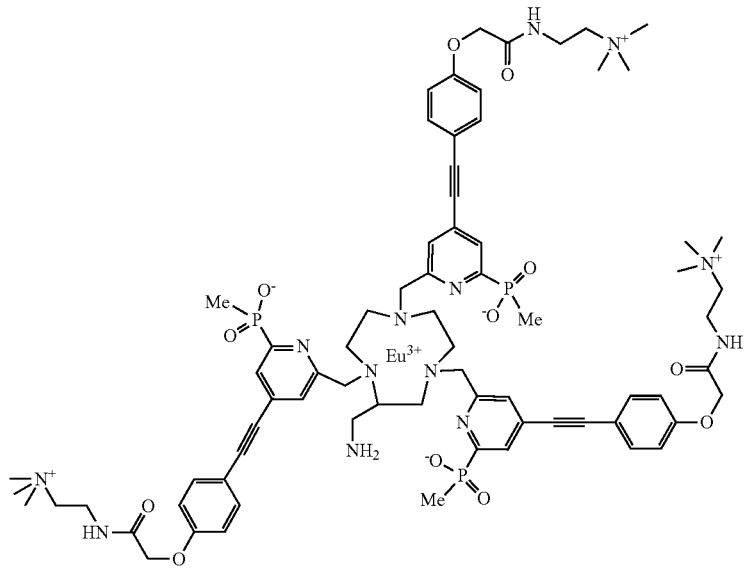

C31
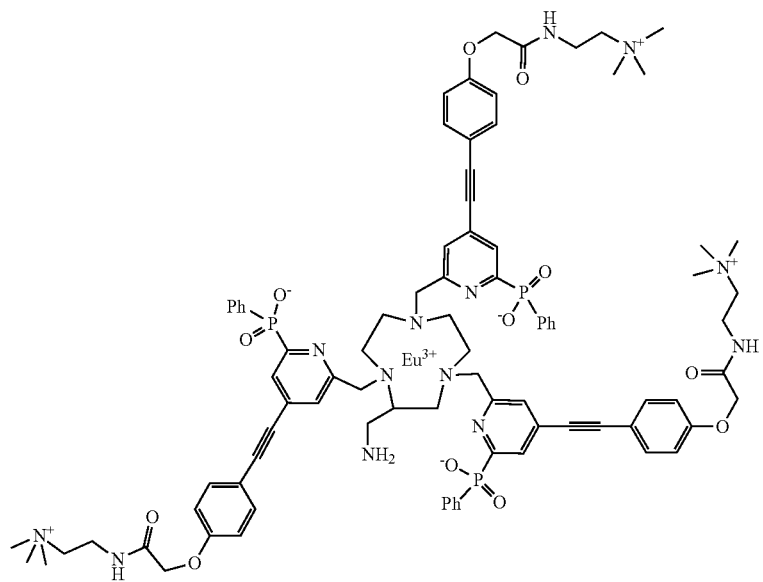
C32
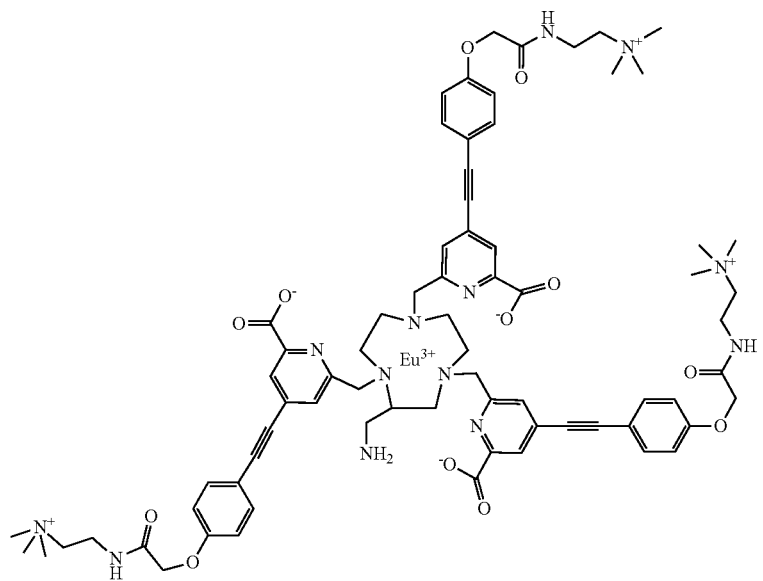

C33
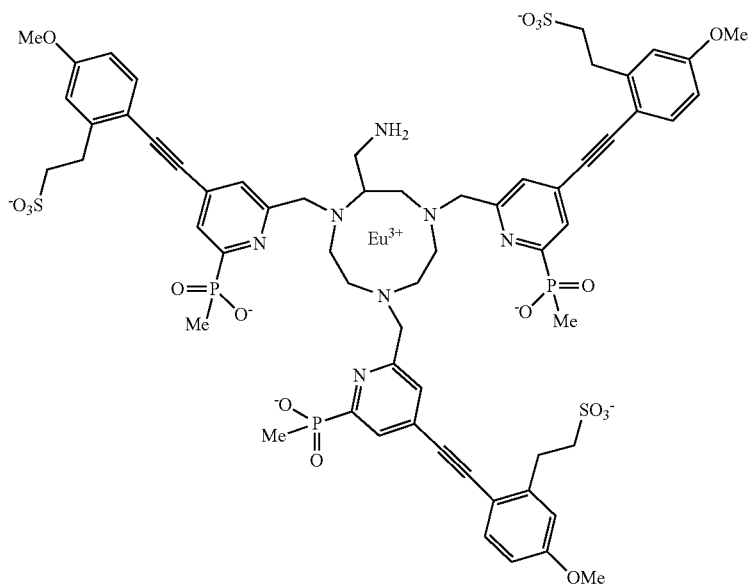
C34
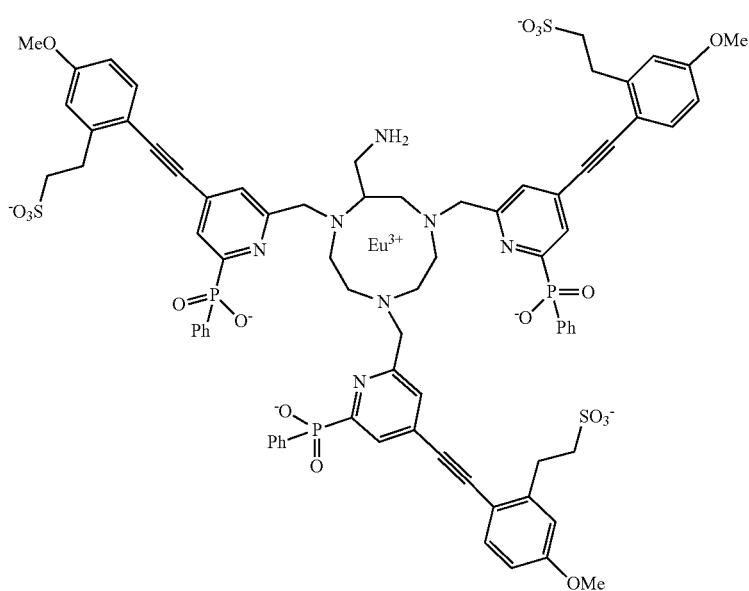

-continued
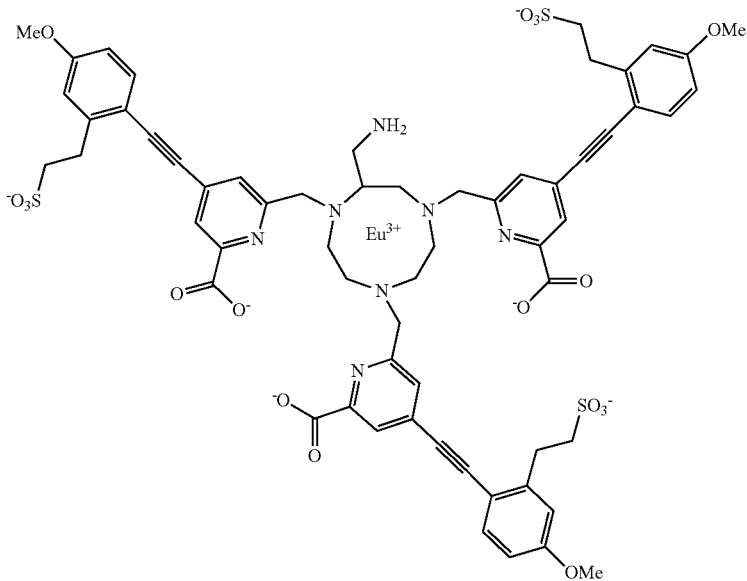
C35
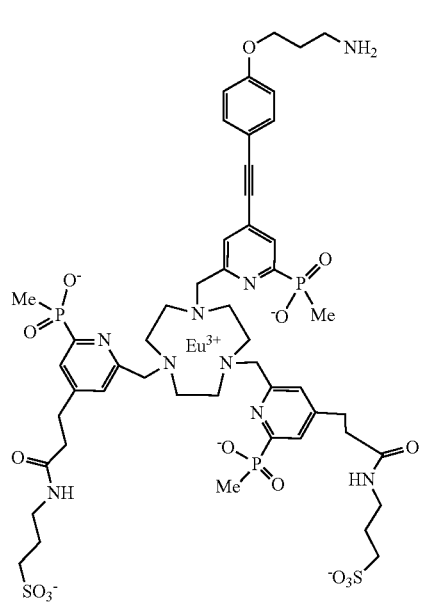
C36
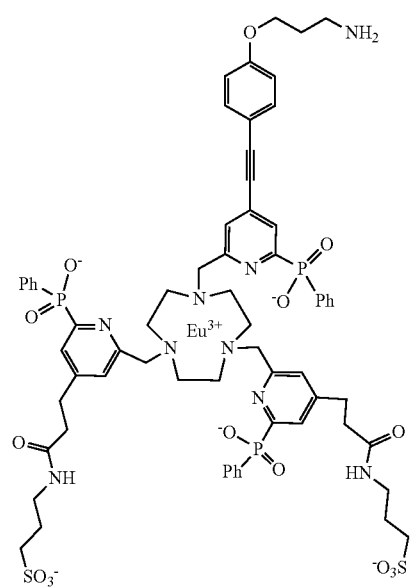
C37

-continued
33
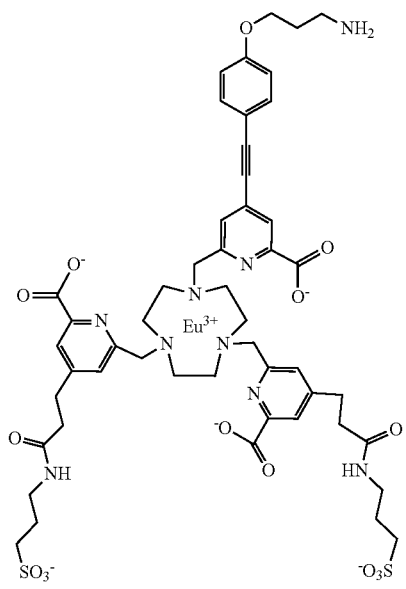
C38
34
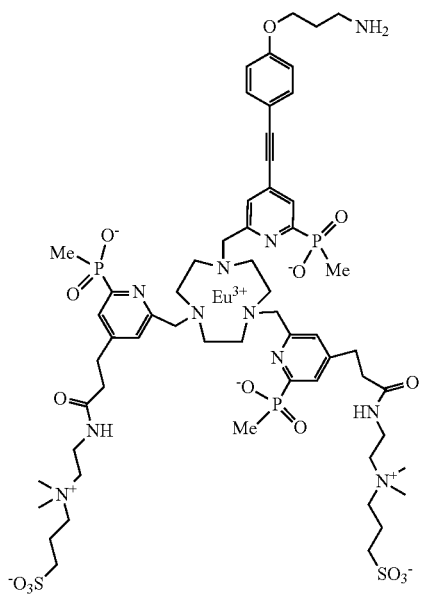
C39
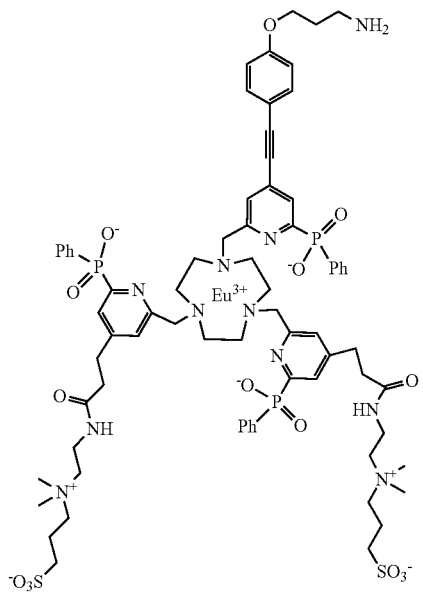
C40
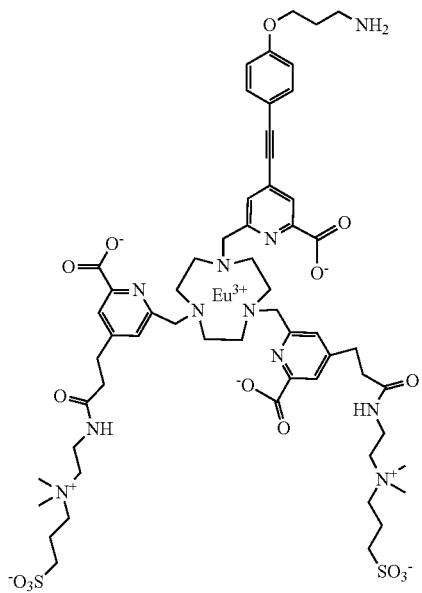
C41

-continued
C42
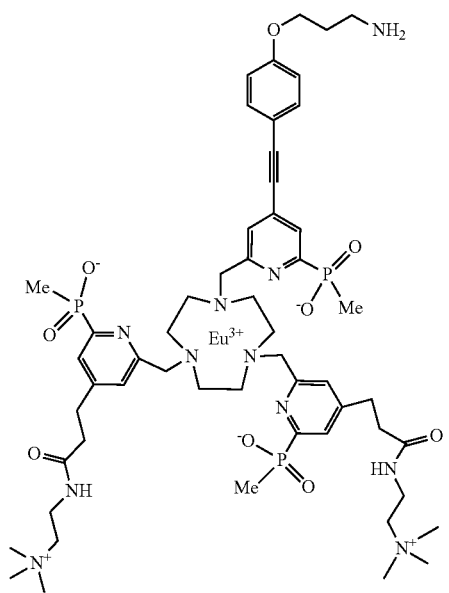
C43
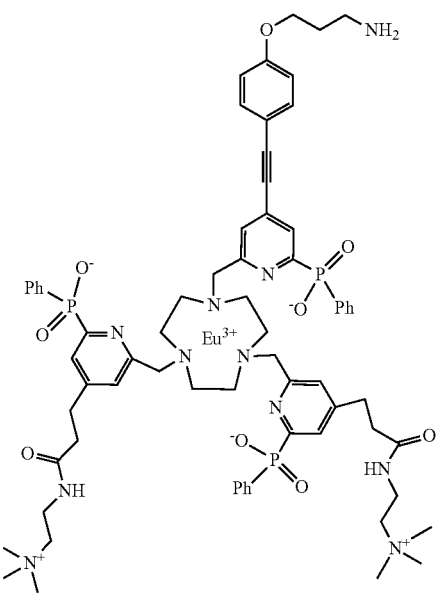
C44
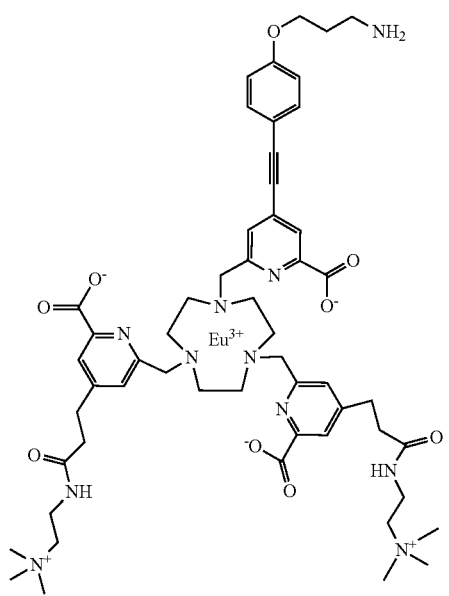
C45
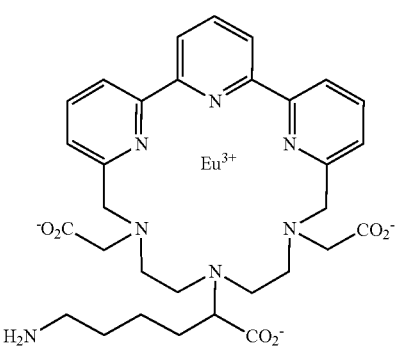
C46
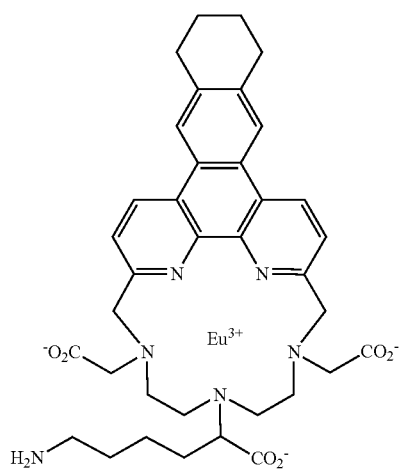
C47
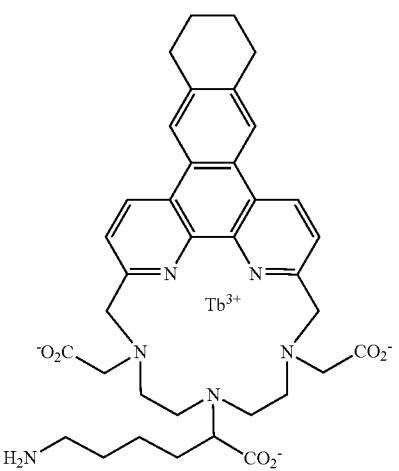

C48
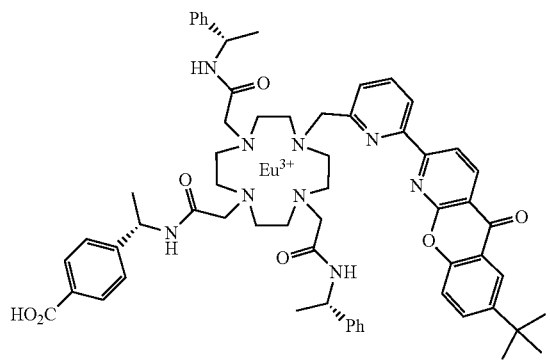
C49
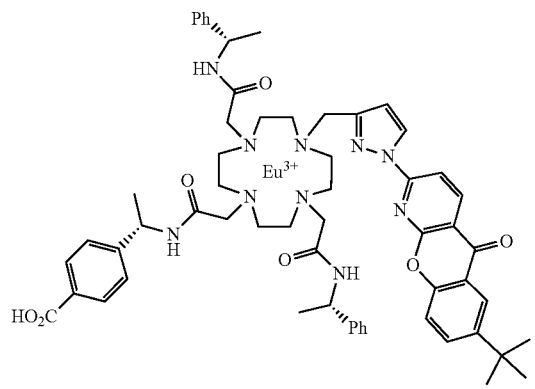
C50
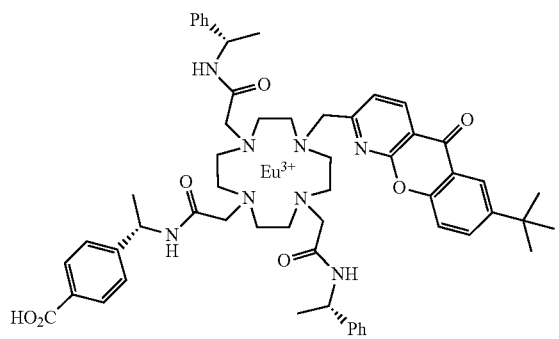
C51
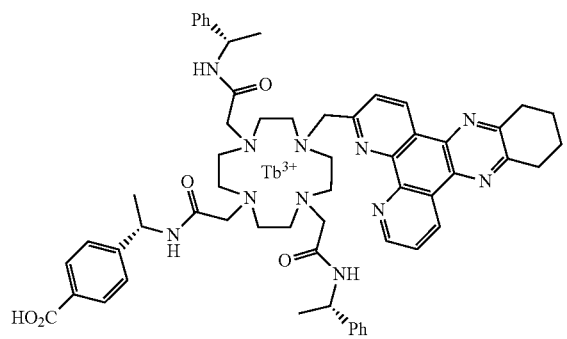
C52
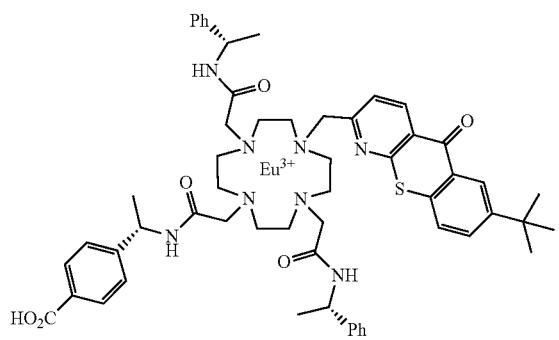
C53
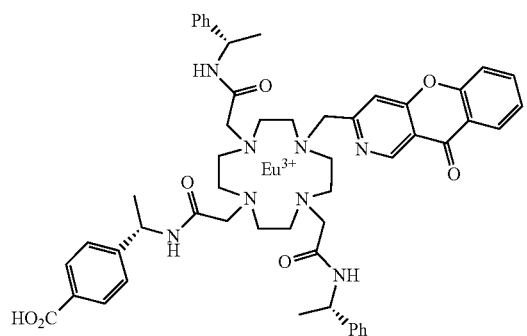

C54
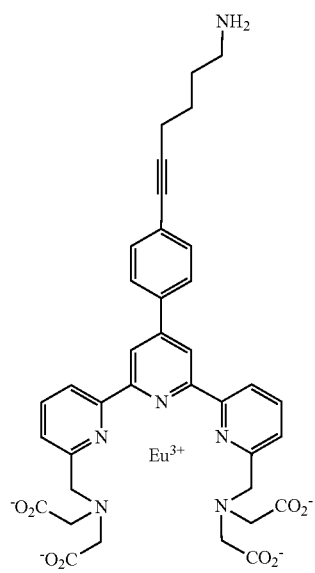
C55
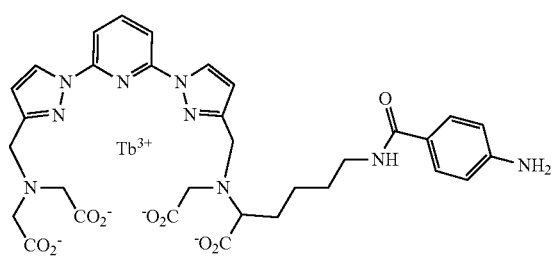
C56
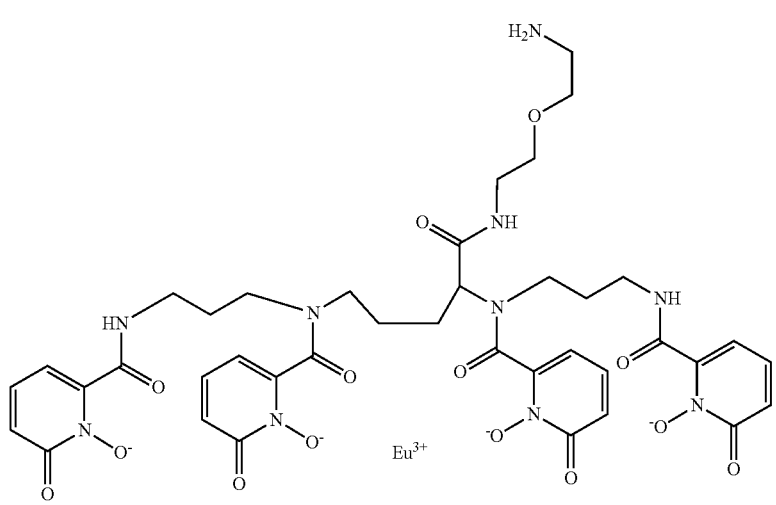
C57
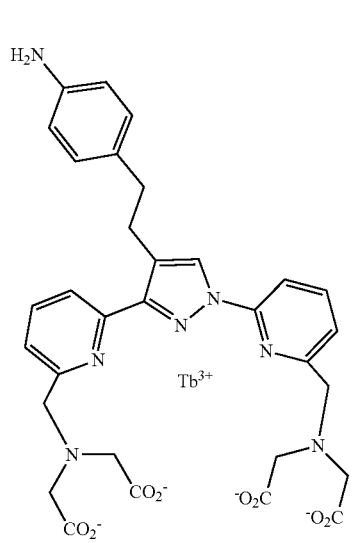
C58
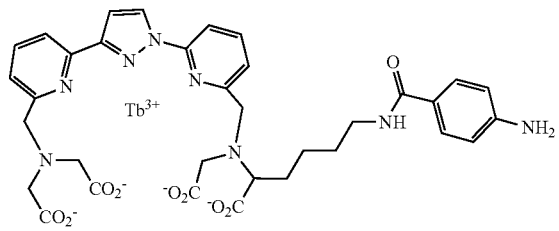

-continued
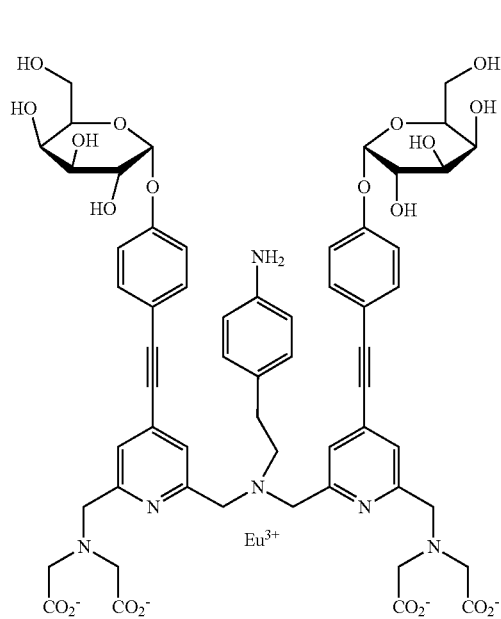
C59
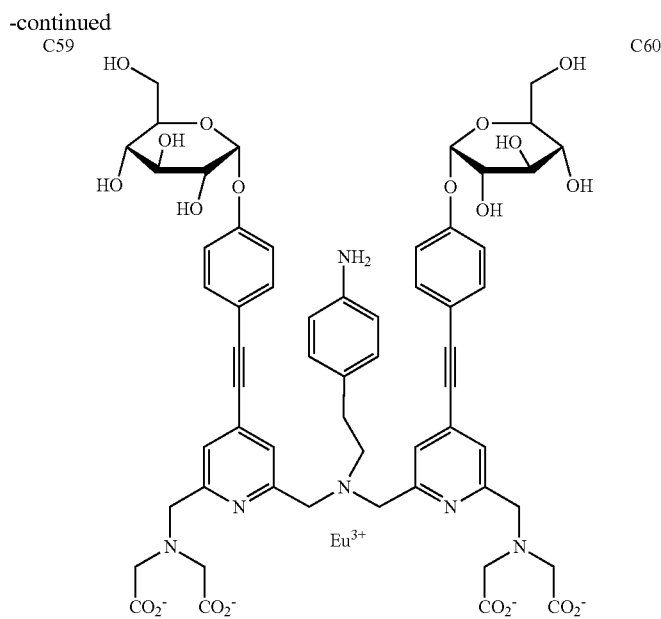
C60
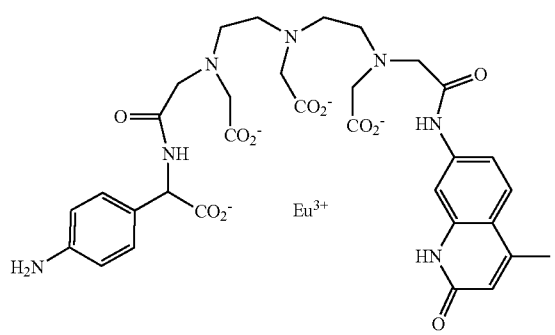
C61
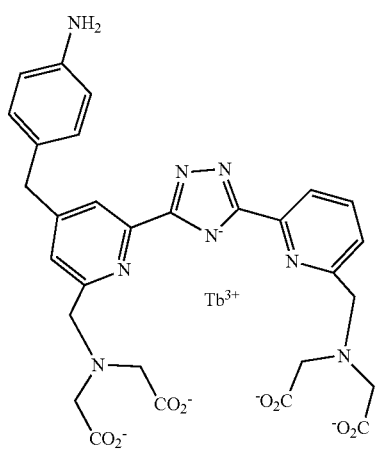
C62
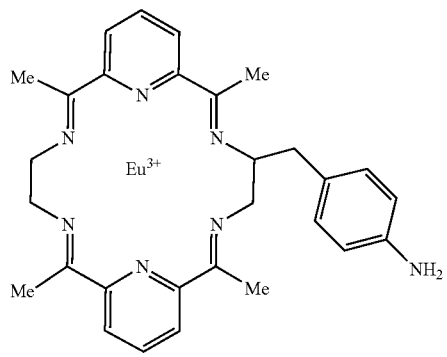
C63
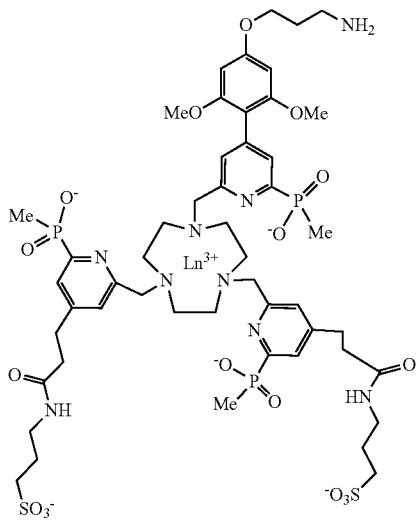
C64a, Ln = Eu
C64b, Ln = Tb -continued
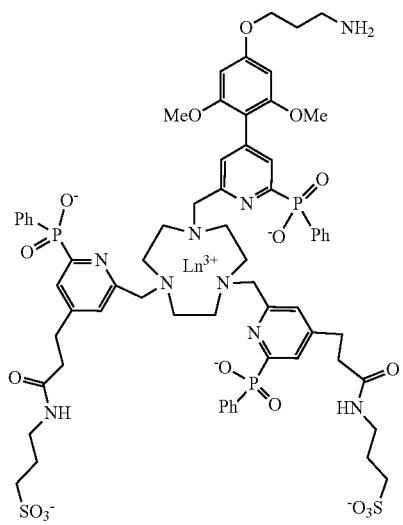
C65a, Ln = Eu
C65b, Ln = Tb
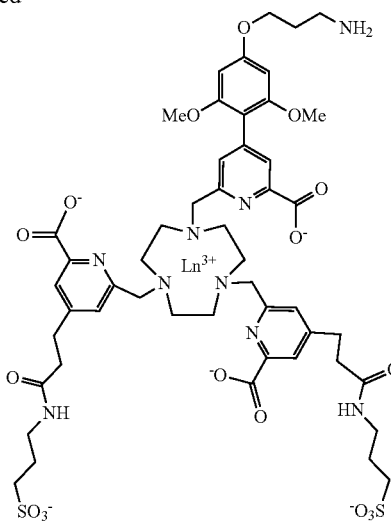
C66a, Ln = Eu
C66b, Ln = Tb
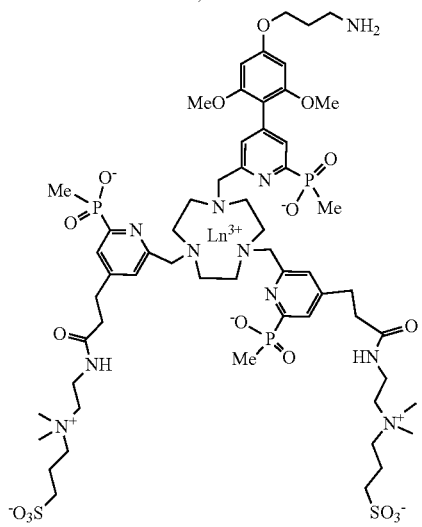
C67a, Ln = Eu
C67b, Ln = Tb
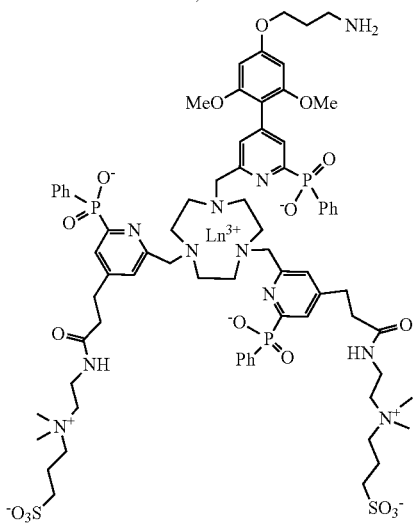
C68a, Ln = Eu
C68b, Ln = Tb
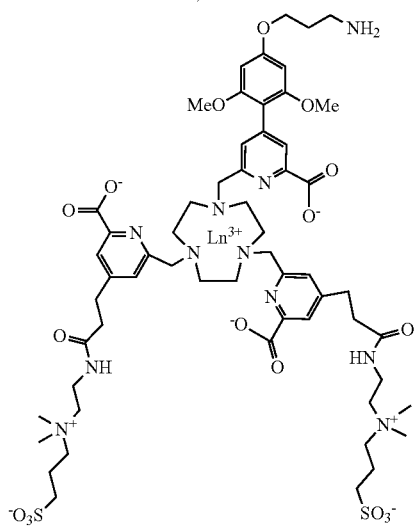
C69a, Ln = Eu
C69b, Ln = Tb
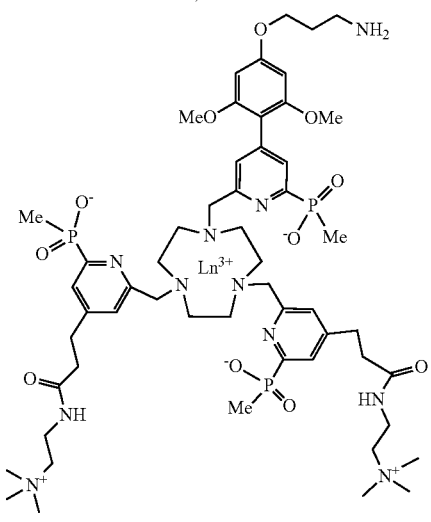
C70a, Ln = Eu
C70b, Ln = Tb

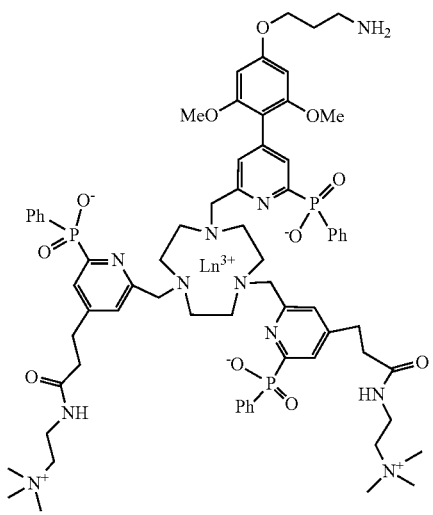
C71a, Ln = Eu
C71b, Ln = Tb
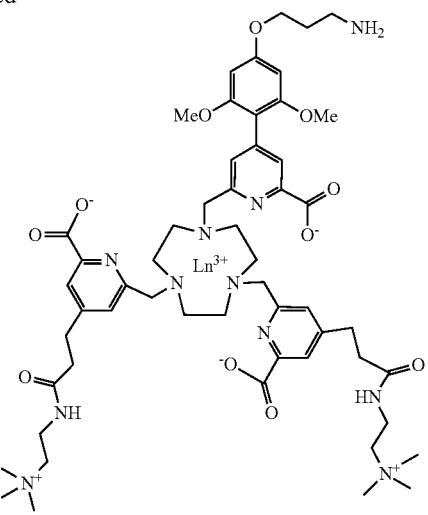
C72a, Ln = Eu
C72b, Ln = Tb
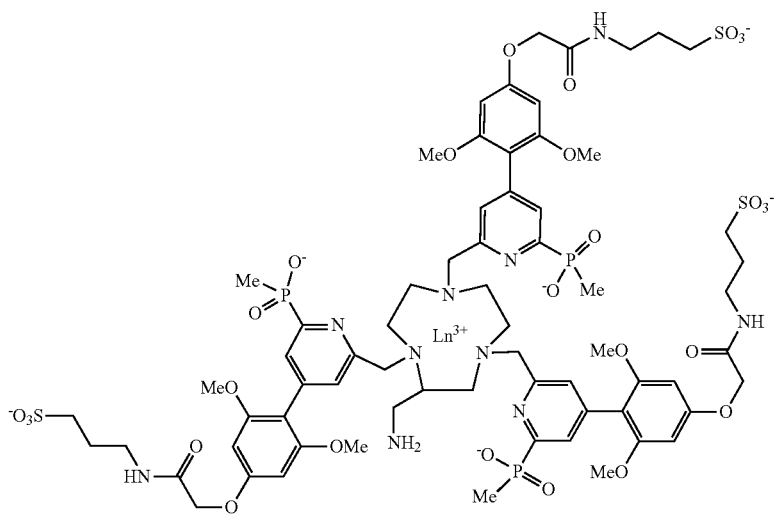
C73a, Ln = Eu
C73b, Ln = Tb
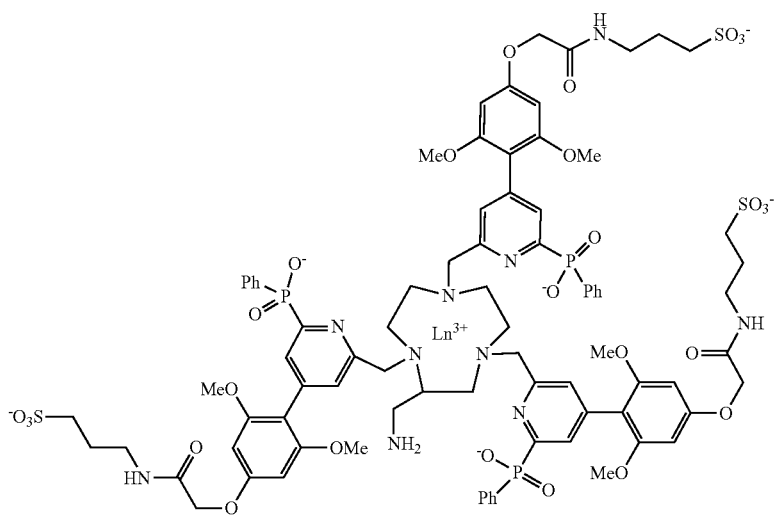
C74a, Ln = Eu
C74b, Ln = Tb -continued
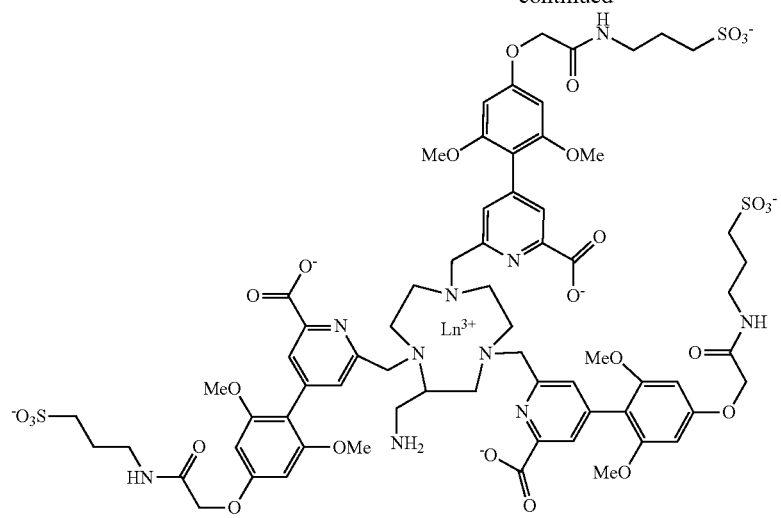
C75a, Ln = Eu
C75b, Ln = Tb
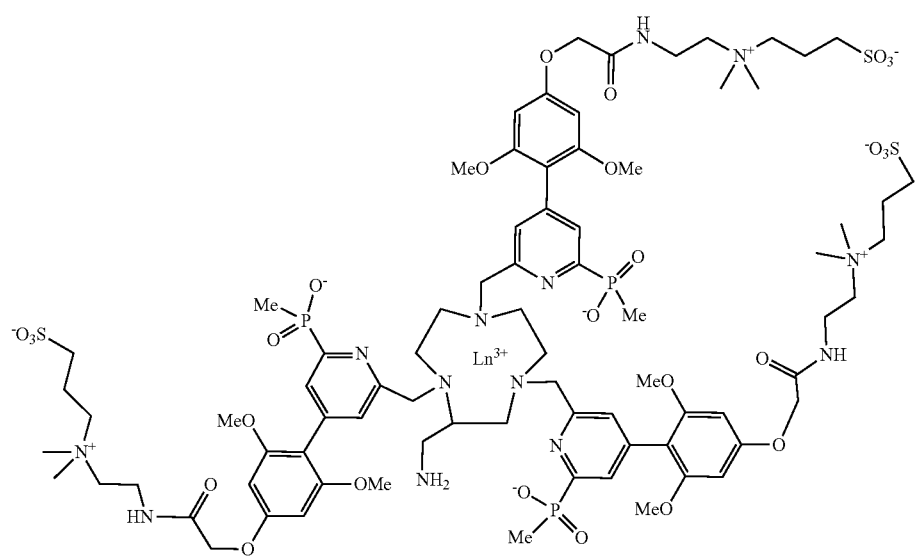
C76a, Ln = Eu
C76b, Ln = Tb

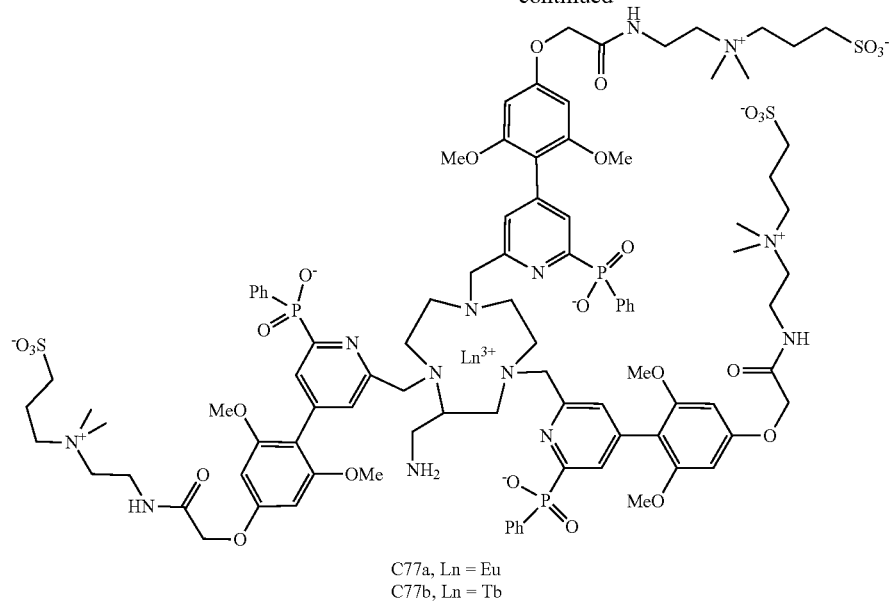
C77a, Ln = Eu
C77b, Ln = Tb
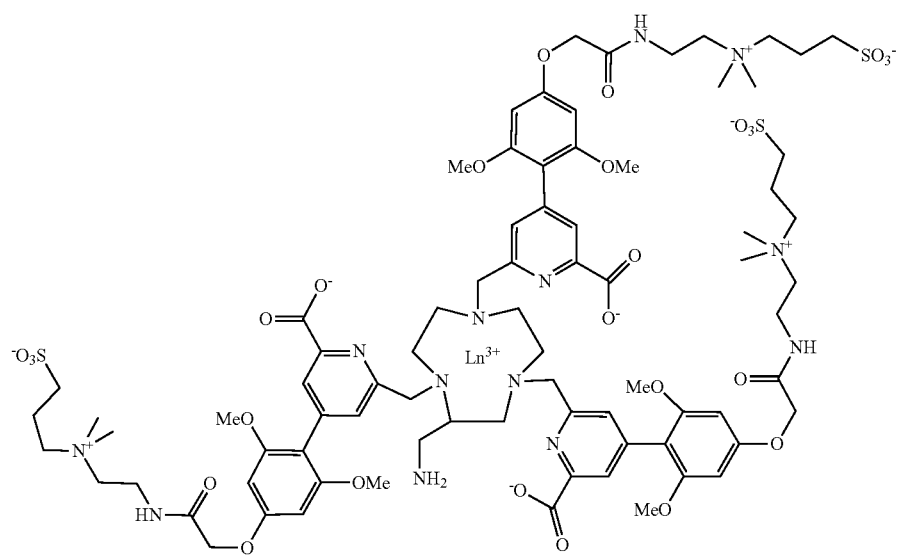
C78a, Ln = Eu
C78b, Ln = Tb

-continued
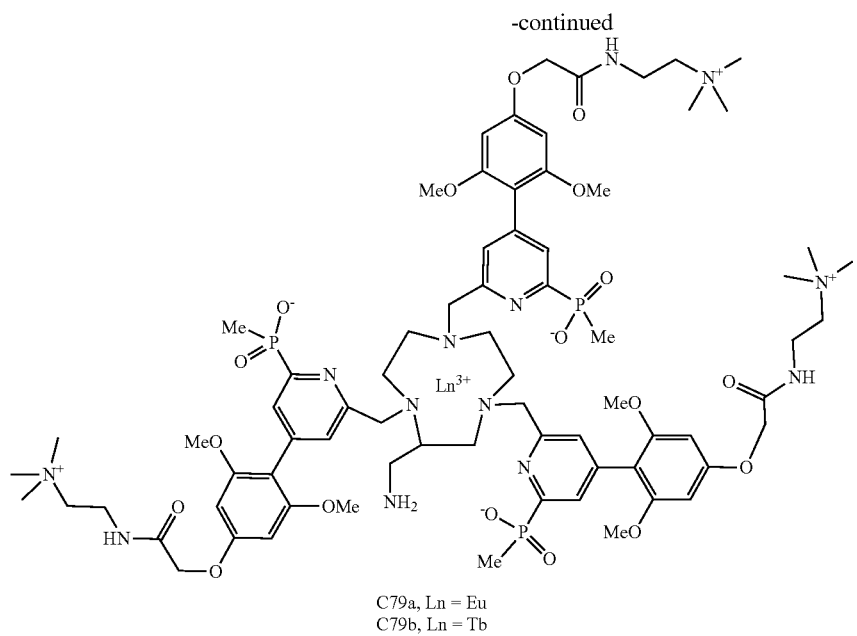
C79a, Ln = Eu
C79b, Ln = Tb
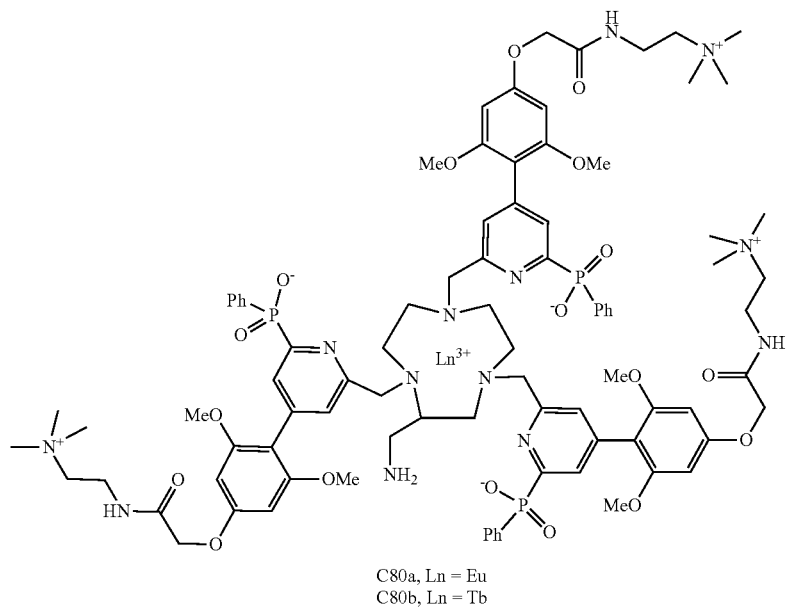
C80a, Ln = Eu
C80b, Ln = Tb -continued
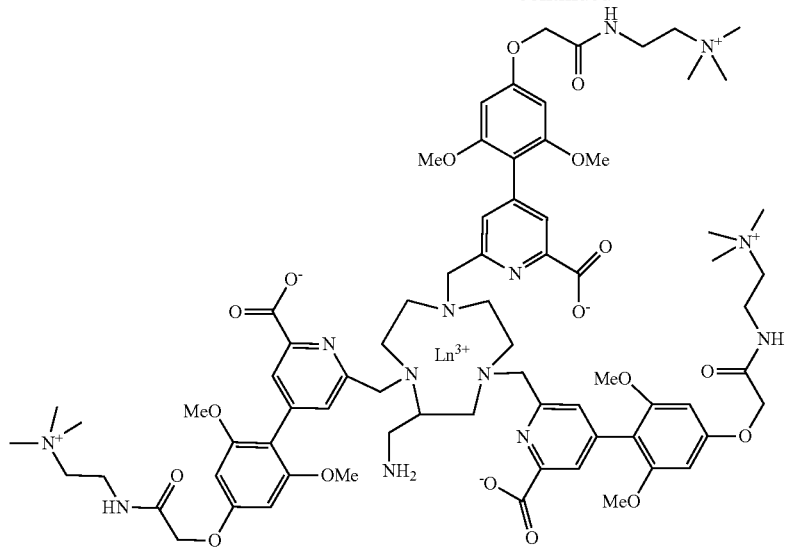
C81a, Ln = Eu
C81b, Ln = Tb
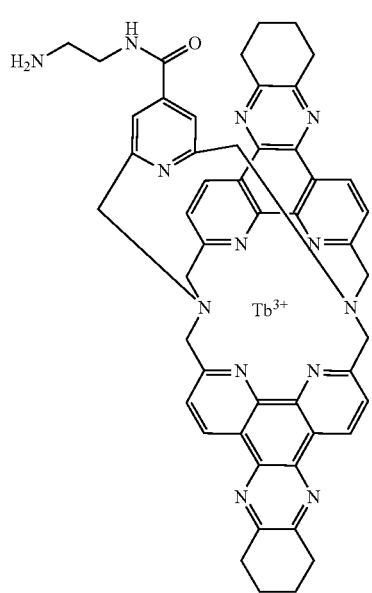
C82
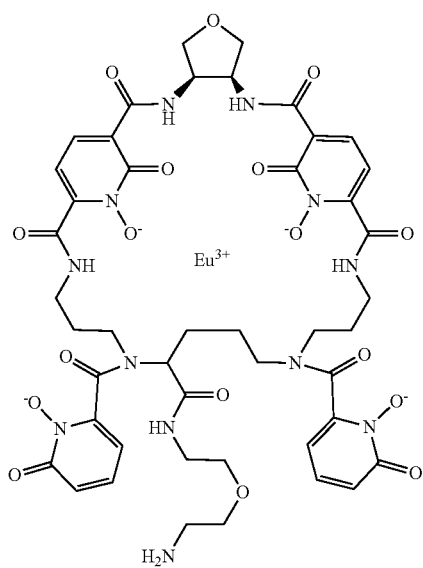
C83

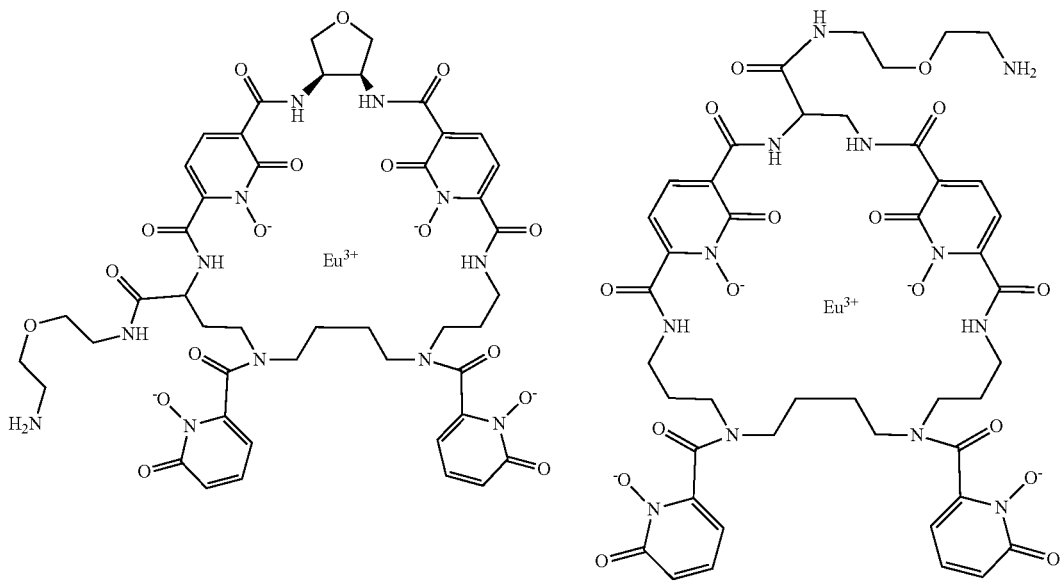
C84
C85
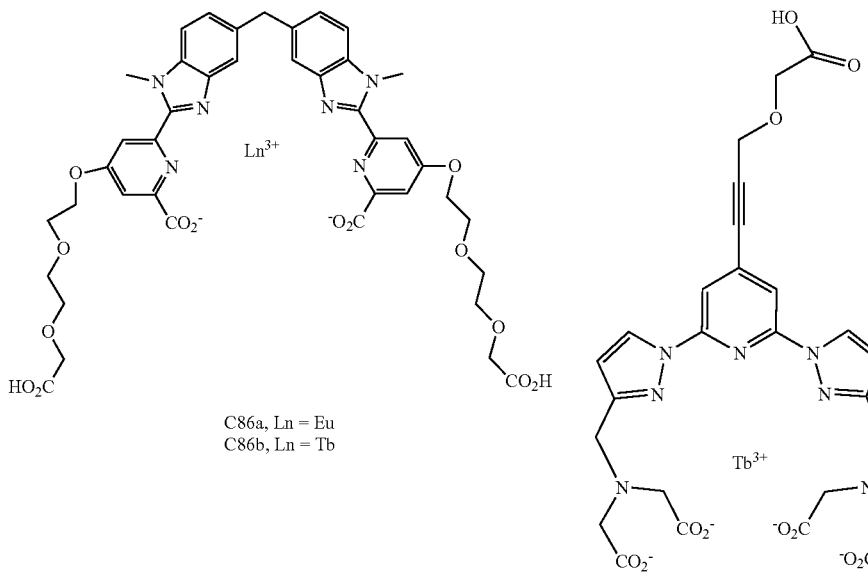
C86a, Ln = Eu
C86b, Ln = Tb
C87
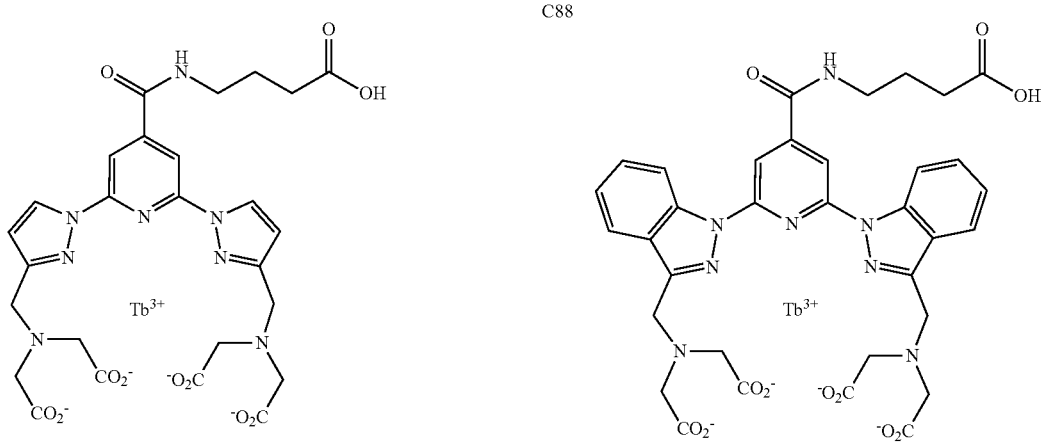
C88
C89

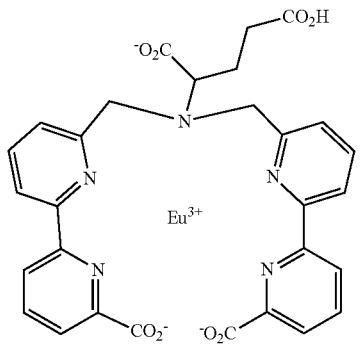

C90

Depending on the pH, the —SO$_3$H, —CO$_2$H and —PO(OH)$_2$ groups are or are not in deprotonated form. These groups thus also denote—SO$_3$—, —CO$_2$— and —PO(OH)O— groups. Advantageously, the lanthanide complex Ln$^{3+}$ is chosen from one of the complexes C1 to C17, C24 to C32 and C36 to C44. More advantageously, the lanthanide complex Ln$^{3+}$ is chosen from one of the complexes C1 to C17 and C36 to C44. More advantageously still, the lanthanide complex Ln$^{3+}$ is chosen from one of the complexes C1 to C17. More advantageously still, the lanthanide complex Ln$^{3+}$ is chosen from one of the complexes C1 to C4 and C11 to C17. More advantageously still, the lanthanide complex Ln$^{3+}$ is chosen from one of the complexes C1 to C4 and C11. Entirely advantageously, the lanthanide complex Ln$^{3+}$ is the complex C2 or the complex C3.

The lanthanide complexes C1 to C90 are described in the publications below. These complexes are either commercially available or can be obtained by the synthesis routes described in said publications.
C1: WO 03/076938
C2: EP-A-0 203 047
C3-C4: WO 2008/025886
C5: Spectrochimica Acta; Part A, Molecular and Biomolecular Spectroscopy, 2001, 57(11), 2197.
C6: Spectrochimica Acta; Part A, Molecular and Biomolecular Spectroscopy, 2001, 57(11), 2197.
C7: Analytical Biochemistry, 2000, 286(1), 17.
C8: WO 01/96877
C9: Spectrochimica Acta; Part A, Molecular and Biomolecular Spectroscopy, 2001, 57(11), 2197.
C10: WO 01/96877
C11: WO 2008/063721
C12-C17: WO 2017/098180.
C18-C20: WO 2013/011236
C21-C35: WO 2014/111661
C36-C44: WO 2018/229408
C45-C47: Organic & Biomolecular Chemistry, 2012, 10, 8509.
C48: WO 2010/084090
C49: WO 2009/010580
C50-C51: Chemical Communications, 2007, 3841
C52: WO 2006/120444
C53: European Journal of Inorganic Chemistry, 2010, 3961.
C54: Bioconjugate Chemistry, 2009, 20(3), 625.
C55: EP-A-0 770 610
C56: WO 2016/106241
C57-C58: EP-A-0 770 610
C59-C60: Analytical Chemistry, 2003, 75, 3193-3201
C61: Bioconjugate Chemistry, 1997, 8(2), 127
C62: WO 93/11433
C63: U.S. Pat. No. 5,696,240
C64a-C81b: WO 2018/22932
C82: WO 2010/070232
C83-C85: WO 2018/045385
C86a-b: Analyst, 2010, 135(1), 42
C87-C89: Chemistry—A European Journal, 2011, 17, 9164
C90: Journal of the American Chemical Society, 2004, 126(15), 4888

The synthesis of the compounds of formula (I) is described in more detail below in schemes 1 to 19. Typically these compounds are obtained by techniques for the conjugation of two organic molecules based on the use of reactive groups, techniques which come within the general knowledge of a person skilled in the art and which are described, for example, in Bioconjugate Techniques, G. T. Hermanson, Academic Press, Second Edition, 2008, pp. 169-211. In order to obtain the GTP-gamma-O compounds, first of all GTP is reacted with a compound of formula G$_2$-L-G$_1$, and the intermediate compound thus formed is conjugated with the lanthanide complex. In this formula, G$_2$-L-G$_1$:

L is the divalent linking group as defined above;

G$_1$ is a reactive electrophilic group capable of reacting with the OH functional group of the phosphate at the gamma position of the GTP;

G$_2$ is a reactive group capable of reacting with a reactive group (G$_3$) carried by the lanthanide complex Ln$^{3+}$.

The conjugation reaction between the intermediate compound (comprising a reactive group G$_2$) and the lanthanide complex (comprising a reactive group G$_3$) results in the formation of a covalent bond comprising one or more atoms of the reactive group.

In one embodiment, the electrophilic group G$_1$ is:
either an OH group activated by a reactant forming in an intermediate way a reactive entity which can react with the hydroxyl functional group of the phosphate at the gamma position,
or a reactive group of the leaving group type, such as, for example, an aliphatic chloride, an aliphatic bromide, an aliphatic iodide, an aliphatic mesylate, an aliphatic tosylate, an aliphatic triflate, and the like.

In one embodiment, the reactive groups G$_2$ and G$_3$ are independently of one another chosen from one of the following groups: an acrylamide, an optionally activated amine (for example a cadaverine or an ethylenediamine), an activated ester, an aldehyde, an alkyl halide, an anhydride, an aniline, an azide, an aziridine, a carboxylic acid, a diazoalkane, a haloacetamide, a halotriazine, such as monochlorotriazine or dichlorotriazine, a hydrazine (including hydrazides), an imido ester, an isocyanate, an isothiocyanate, a maleimide, a sulfonyl halide, a thiol, a ketone, an acid halide, a succinimidyl ester, a hydroxysuccinimidyl ester, a hydroxysulfosuccinimidyl ester, an azidonitrophenyl, an azidophenyl, a 3-(2-pyridyldithio)propionamide, a glyoxal, a triazine, an acetylenic group, and in particular a group chosen from the groups of formulae:

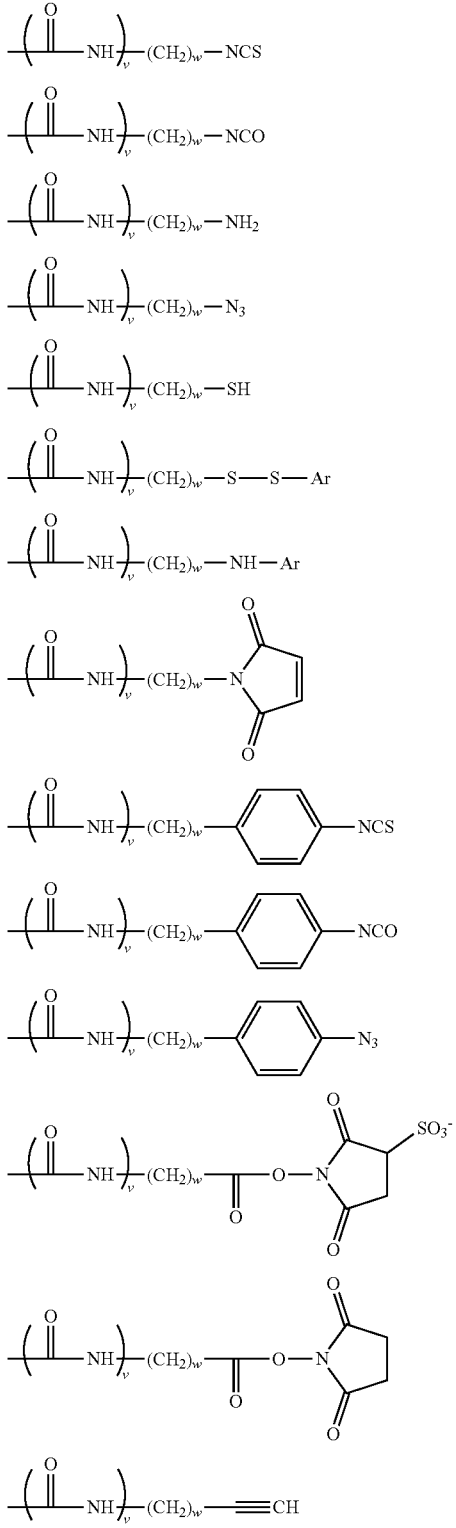

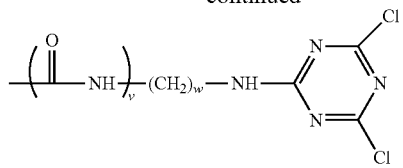

in which w varies from 0 to 8 and v is equal to 0 or 1, and Ar is a saturated or unsaturated 5- or 6-membered heterocycle comprising from 1 to 3 heteroatoms which is optionally substituted by a halogen atom.

$G_2$ and $G_3$ can originate from their form protected by a compatible protective group.

Preferably, the reactive groups $G_2$ and $G_3$ are independently of one another chosen from an amine (optionally protected in the —NHBoc form), a succinimidyl ester, a hydroxysuccinimidyl ester, a haloacetamide, a hydrazine, a halotriazine, an isothiocyanate, a maleimide group or a carboxylic acid (optionally protected in the form of a —$CO_2$Me or —$CO_2$tBu group). In the latter case, the acid will have to be activated in the ester form in order to be able to react with a nucleophilic entity.

In order to obtain GTP-gamma-N compounds, GTP can be reacted directly with a lanthanide complex when the latter has an $NH_2$ group. GTP can also be reacted with a compound of formula $_2HN$—$(CH_2)_n$—$NH_2$ in which n is as defined above and one of the amino groups is optionally protected by a protective group, and then the intermediate compound obtained can be coupled with a lanthanide complex functionalized by a reactive group $G_3$ as defined above.

The compounds according to the invention are capable of binding to G protein. This property is demonstrated by an immunoassay based on a FRET principle, by incubating a membrane preparation comprising GPCRs and a Gα protein in the presence of a pair of FRET partners consisting of a compound according to the invention and of an anti-Gα protein antibody labeled with an acceptor fluorophore. Incubation is carried out in the presence or absence of a non-hydrolyzable or slowly hydrolyzable GTP analog, such as GTPγS. When the partners of the FRET pair bind to the same Gα protein, a FRET signal appears, thereby demonstrating the binding of the compound of the invention to the Gα protein. The compounds of the invention can thus advantageously be used to identify, by the FRET technique, molecules capable of modulating the activation of a G protein-coupled receptor.

Synthesis

The syntheses of GTPs coupled in the gamma position to lanthanide complexes are described in schemes 1 to 19.

Synthesis of the Compounds of the GTP-Gamma-O (GTPγO) Family

Compound 2, which is a precursor of the compounds of the invention (lanthanide complex GTP), can be synthesized by following the protocols known to a person skilled in the art. Starting from commercially available GTP, the linking group "L1" is introduced at the gamma position of the GTP by nucleophilic substitution between the GTP and the linking group having a leaving group (I, Br, mesyl, tosyl) at the alpha position and a protected amino group on its omega position, thus resulting in compound 1. Analogous coupling examples are available when P=CBz or $COCF_3$ (cf. WO 2009/105077 or WO 2009/091847). The protective group is removed using the deprotection conditions corresponding to the protective groups (cf. WO 2009/014612). Compound 2 is then covalently coupled via an amide bond to the lanthanide complex using conventional methods known to a person skilled in the art (scheme 1).

Scheme 1

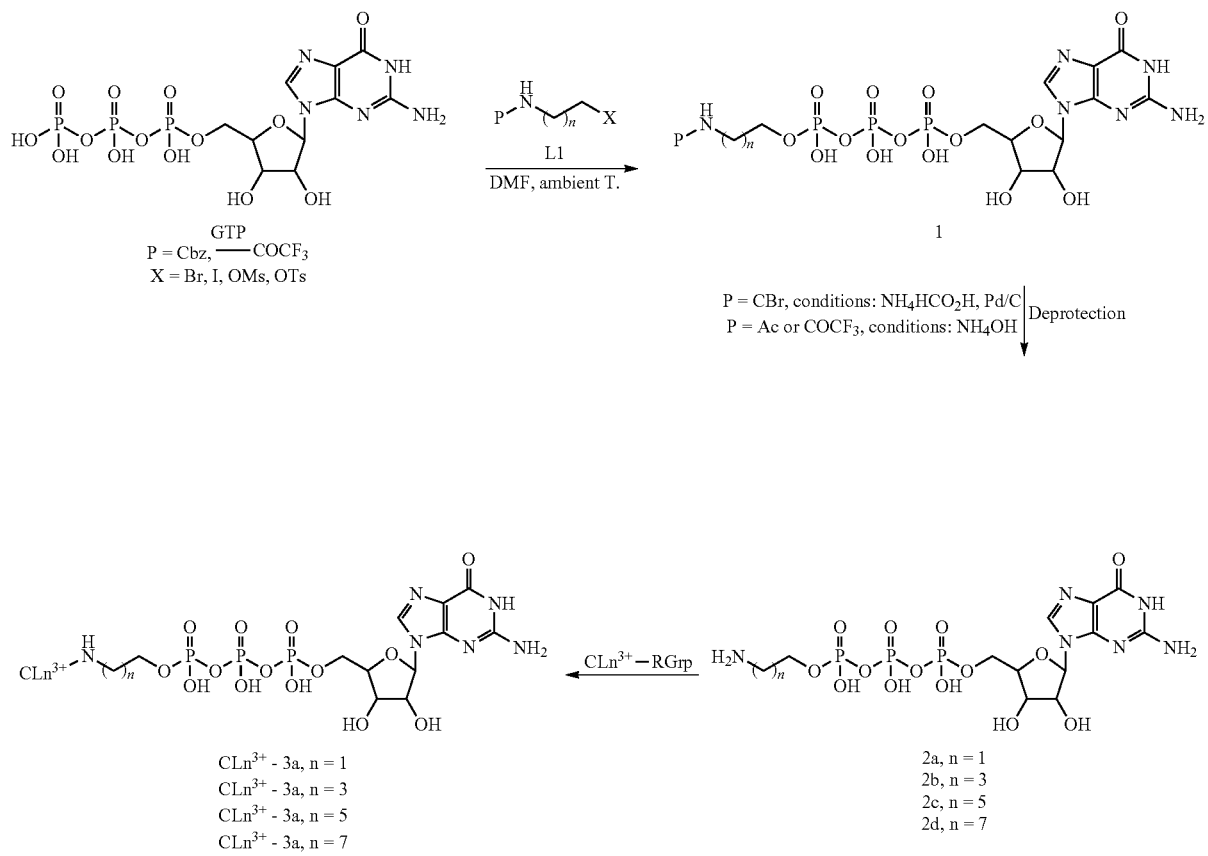

Another alternative for coupling the lanthanide complex at the gamma position of the GTP is the use of "click chemistry". For this, it is necessary, to begin with, to introduce either an azido group (scheme 2) or an acetylenic group (scheme 3). As above, these groups are introduced via a nucleophilic substitution reaction between the linking group L2 or L3 and the GTP (schemes 2 and 3). Examples of couplings between a nucleotide and a linking group are described, for example, by Hacker et al. (The Journal of Organic Chemistry, 2012, 77 (22), 17450).

Scheme 2

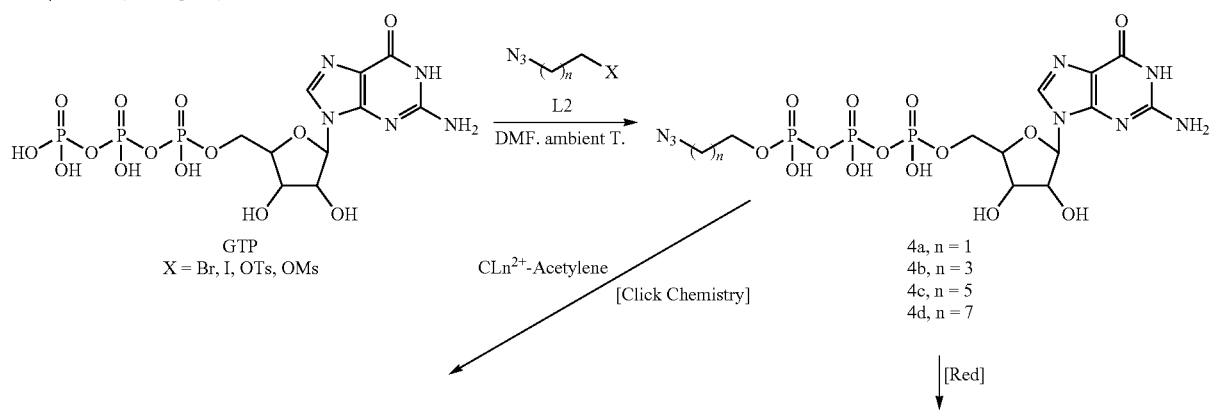

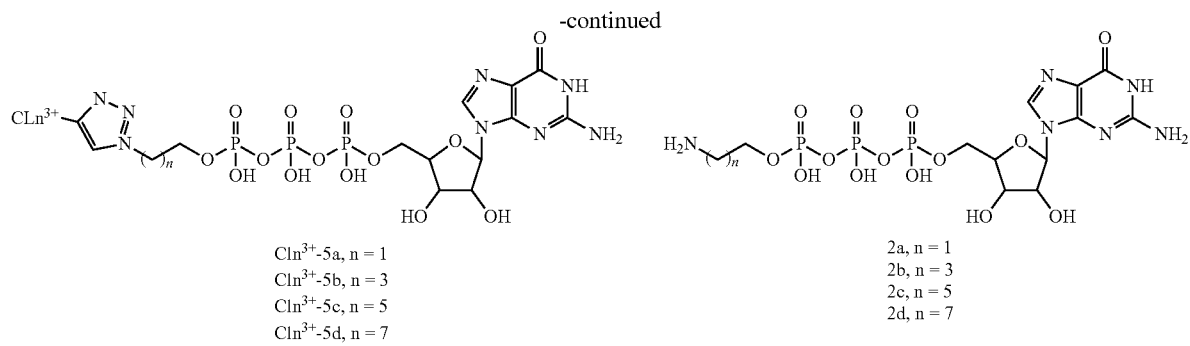

CLn³⁺-5a, n = 1
CLn³⁺-5b, n = 3
CLn³⁺-5c, n = 5
CLn³⁺-5d, n = 7

2a, n = 1
2b, n = 3
2c, n = 5
2d, n = 7

Scheme 3

GTPγO series (acetylenic option)

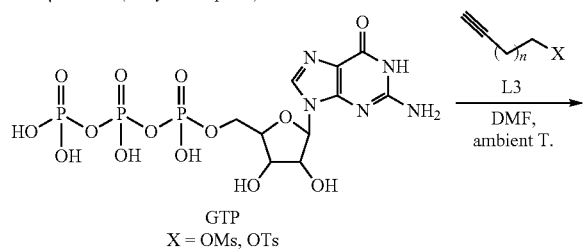

GTP
X = OMs, OTs

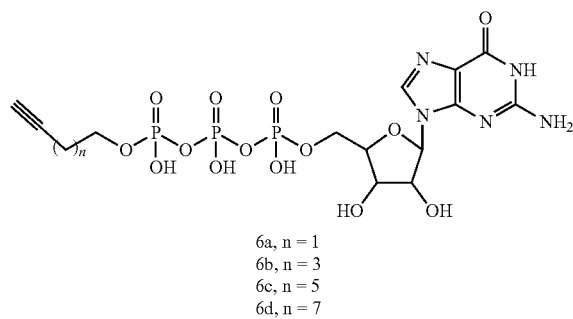

6a, n = 1
6b, n = 3
6c, n = 5
6d, n = 7

| CLn³⁺—N₃

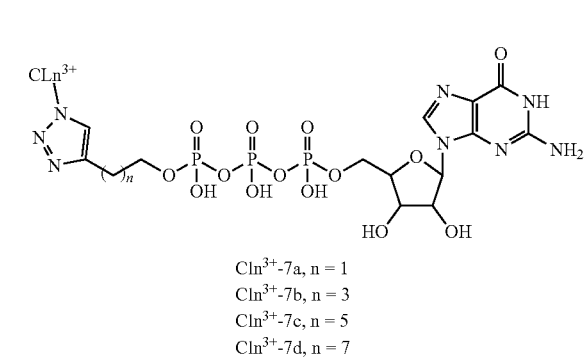

CLn³⁺-7a, n = 1
CLn³⁺-7b, n = 3
CLn³⁺-7c, n = 5
CLn³⁺-7d, n = 7

Conversely, the acetylenic group can be introduced in a first stage onto the GTP, resulting in the compounds of the series 6. An example of coupling to other nucleotides is available in the literature (Journal of the American Chemical Society, 2003, 125, 9588). Then the cycloaddition reaction can be carried out with a lanthanide complex functionalized in the azide form to result in the compounds CLn³⁺-7a-d.

Synthesis of the Compounds of the GTP-Gamma-N Family

In the same way as for the GTP-gamma-O family, the GTP-gamma-N compounds can be prepared according to an analogous strategy. The NH₂-functionalized lanthanide complex is condensed directly onto the GTP molecule without intercalation of linker (scheme 4).

Scheme 4

Direct GTPγN series

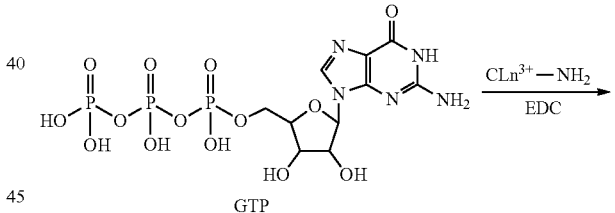

GTP

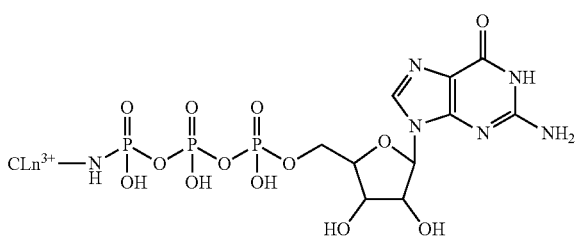

CLn³⁺-B

The lanthanide complexes can be coupled using a GTP-gamma-N molecule already comprising a terminal NH₂ linking group previously introduced 9a-e.

Scheme 5

GTPγN series with introduction of a diamino linker

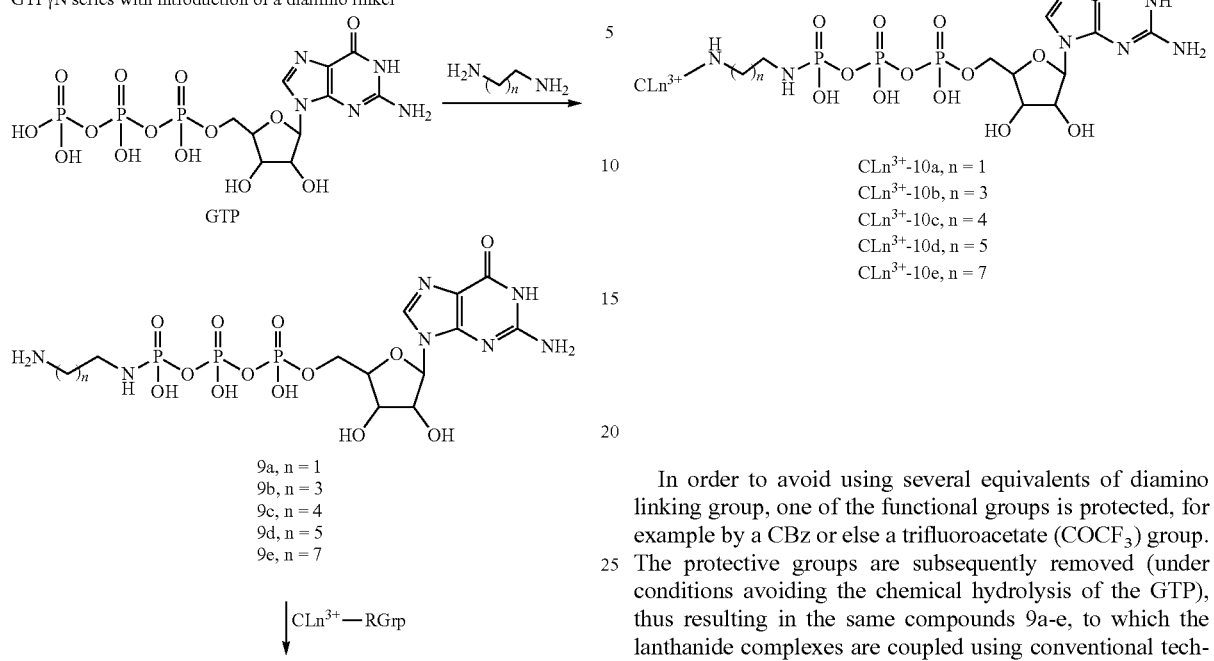

9a, n = 1
9b, n = 3
9c, n = 4
9d, n = 5
9e, n = 7

CLn³⁺-10a, n = 1
CLn³⁺-10b, n = 3
CLn³⁺-10c, n = 4
CLn³⁺-10d, n = 5
CLn³⁺-10e, n = 7

In order to avoid using several equivalents of diamino linking group, one of the functional groups is protected, for example by a CBz or else a trifluoroacetate (COCF₃) group. The protective groups are subsequently removed (under conditions avoiding the chemical hydrolysis of the GTP), thus resulting in the same compounds 9a-e, to which the lanthanide complexes are coupled using conventional techniques known to a person skilled in the art (scheme 6).

Scheme 6

GTPγN series (with protective group)

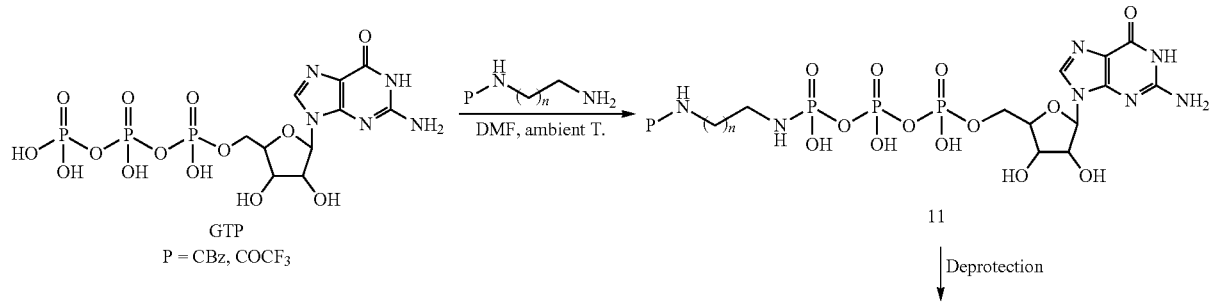

P = CBz, COCF₃

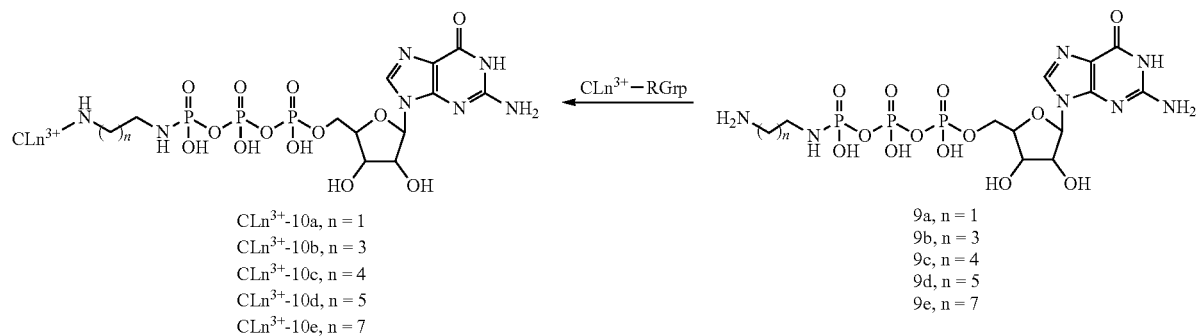

CLn³⁺-10a, n = 1
CLn³⁺-10b, n = 3
CLn³⁺-10c, n = 4
CLn³⁺-10d, n = 5
CLn³⁺-10e, n = 7

9a, n = 1
9b, n = 3
9c, n = 4
9d, n = 5
9e, n = 7

Synthesis of the Compounds of the GTP-Gamma-C Family

The GTP-gamma-C series is synthesized by condensation of GDP (guanosine diphosphate) with phosphonic acids, the terminal position of which can be substituted in different ways. When the terminal position is a protected (trifluoroacetamide 15a-f or CBz 16a-f) amine functional group, these compounds are prepared using the method described in the literature (EP 0 959 077 (TFA); WO 2012/150866 and The Journal of Organic Chemistry, 1984, 49, 1158 (CBz)). N-Phthalimidoalkyl bromides (12a-f) are condensed with triethyl phosphite in a first stage, subsequently followed by treatment with hydrazine to deprotect the amine functional group. The ethyl phosphonates are hydrolyzed in the presence of hydrobromic acid to result in compounds 14a-f. The primary amine functional group is protected either by a CBz or by a trifluoroacetamide in order to prevent a self-condensation reaction during the coupling reaction with GDP. This reaction sequence makes it possible to obtain the intermediate compounds 15a-f and 16a-f.

Scheme 7

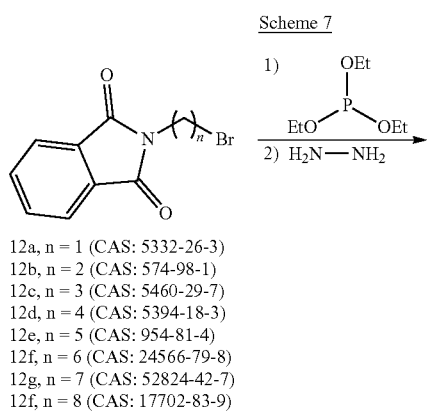

12a, n = 1 (CAS: 5332-26-3)
12b, n = 2 (CAS: 574-98-1)
12c, n = 3 (CAS: 5460-29-7)
12d, n = 4 (CAS: 5394-18-3)
12e, n = 5 (CAS: 954-81-4)
12f, n = 6 (CAS: 24566-79-8)
12g, n = 7 (CAS: 52824-42-7)
12f, n = 8 (CAS: 17702-83-9)

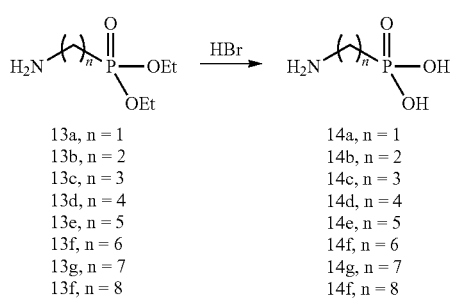

13a, n = 1
13b, n = 2
13c, n = 3
13d, n = 4
13e, n = 5
13f, n = 6
13g, n = 7
13f, n = 8

14a, n = 1
14b, n = 2
14c, n = 3
14d, n = 4
14e, n = 5
14f, n = 6
14g, n = 7
14f, n = 8

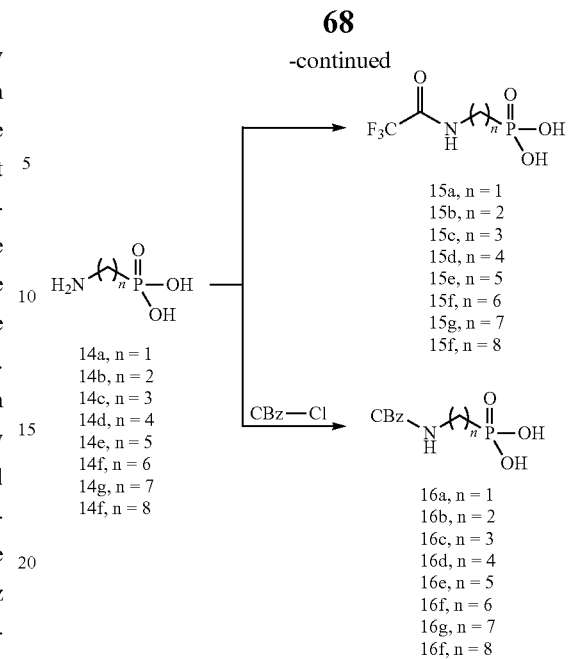

14a, n = 1
14b, n = 2
14c, n = 3
14d, n = 4
14e, n = 5
14f, n = 6
14g, n = 7
14f, n = 8

15a, n = 1
15b, n = 2
15c, n = 3
15d, n = 4
15e, n = 5
15f, n = 6
15g, n = 7
15f, n = 8

16a, n = 1
16b, n = 2
16c, n = 3
16d, n = 4
16e, n = 5
16f, n = 6
16g, n = 7
16f, n = 8

Instead of introducing a masked primary amine functional group, it is also possible to have available GTP-gamma-C, the terminal part of the linker of which is an acetylenic unit. This functional group makes it possible to carry out a "Click Chemistry" reaction between the acetylenic GTP-gamma-C and a lanthanide complex carrying an azide functional group available for a coupling reaction. Scheme 8 briefly describes the various intermediates prepared according to the protocols available in the literature (Bioorganic Medicinal Chemistry, 2018, 26, 191, and Angewandte Chemie International Edition, 2011, 50, 10699). The commercial acetylenic alkyl bromide derivatives are condensed with trimethylsilyl phosphite, then hydrolyzed to result in the 18a-f series.

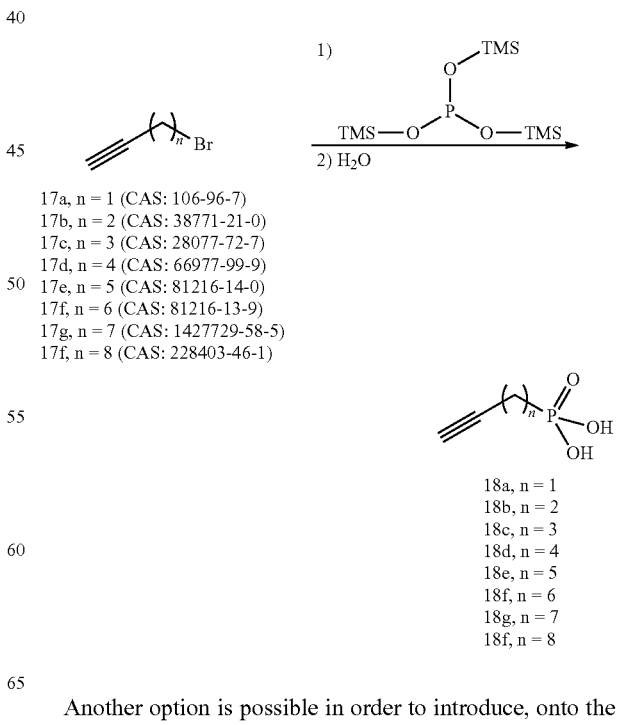

17a, n = 1 (CAS: 106-96-7)
17b, n = 2 (CAS: 38771-21-0)
17c, n = 3 (CAS: 28077-72-7)
17d, n = 4 (CAS: 66977-99-9)
17e, n = 5 (CAS: 81216-14-0)
17f, n = 6 (CAS: 81216-13-9)
17g, n = 7 (CAS: 1427729-58-5)
17f, n = 8 (CAS: 228403-46-1)

18a, n = 1
18b, n = 2
18c, n = 3
18d, n = 4
18e, n = 5
18f, n = 6
18g, n = 7
18f, n = 8

Another option is possible in order to introduce, onto the linker of the GTP-gamma-C compounds, a functional group making possible bioconjugation. In this approach, the azido group is introduced onto the phosphonic acid using the sequence described in scheme 9. The protocols are described in the literature, for example in Chemistry, A European Journal, 2010, 16, 12718, Langmuir, 2010, 26, 10725, or indeed also in The Journal of Organic Chemistry, 2012, 77, 10450. The dibrominated derivatives react with triethyl phosphite to give compounds 20a-f. The azido functional group is subsequently introduced by a simple nucleophilic substitution with sodium azide. The diesters are subsequently hydrolyzed in the presence of TMS-Br, which results in derivatives 22a-f.

Scheme 9

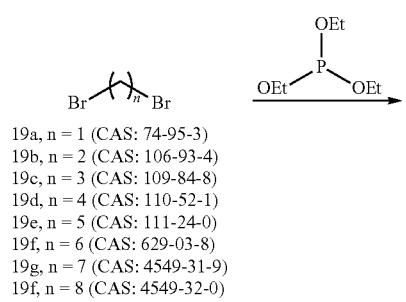

19a, n = 1 (CAS: 74-95-3)
19b, n = 2 (CAS: 106-93-4)
19c, n = 3 (CAS: 109-84-8)
19d, n = 4 (CAS: 110-52-1)
19e, n = 5 (CAS: 111-24-0)
19f, n = 6 (CAS: 629-03-8)
19g, n = 7 (CAS: 4549-31-9)
19f, n = 8 (CAS: 4549-32-0)

20a, n = 1
20b, n = 2
20c, n = 3
20d, n = 4
20e, n = 5
20f, n = 6
20g, n = 7
20f, n = 8

21a, n = 1
21b, n = 2
21c, n = 3
21d, n = 4
21e, n = 5
21f, n = 6
21g, n = 7
21f, n = 8

22a, n = 1
22b, n = 2
22c, n = 3
22d, n = 4
22e, n = 5
22f, n = 6
22g, n = 7
22f, n = 8

Scheme 10

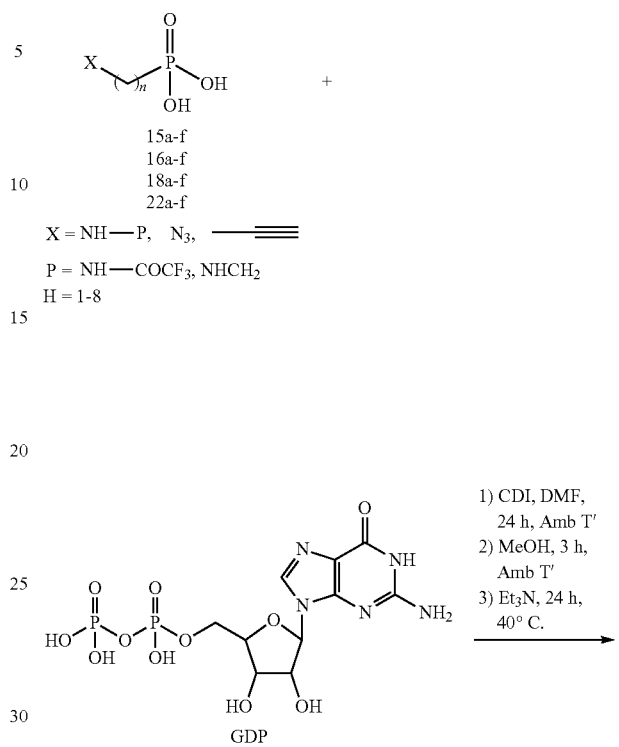

15a-f
16a-f
18a-f
22a-f

X = NH—P, $N_3$, —≡

P = NH—$COCF_3$, $NHCH_2$
H = 1-8

Functionalized GTP-gamma-C compounds

Scheme 11

X = NH—P

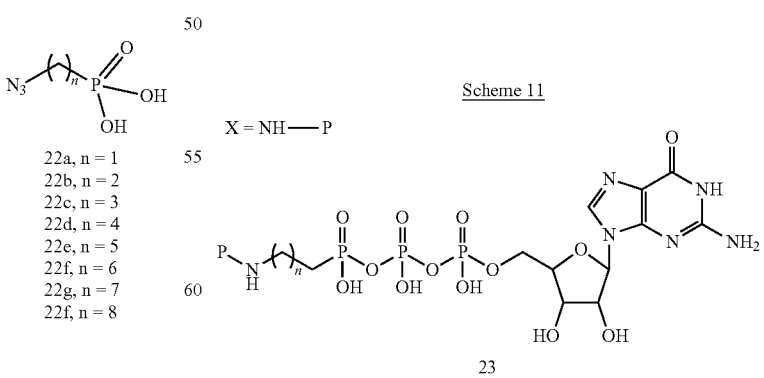

23

Deprotection ↓

The coupling of compounds 15a-f, 16a-f, 18a-f or 22a-f with the lanthanide complexes is carried out using conventional techniques known to a person skilled in the art (schemes 10 to 13).

-continued

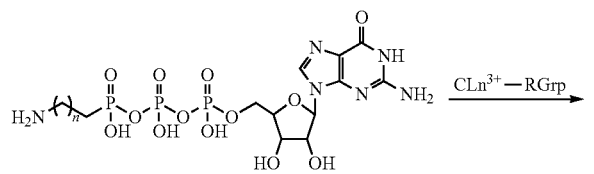

24a, n = 0
24b, n = 1
24c, n = 2
24d, n = 3
24e, n = 4
24f, n = 5
24g, n = 6
24h, n = 7

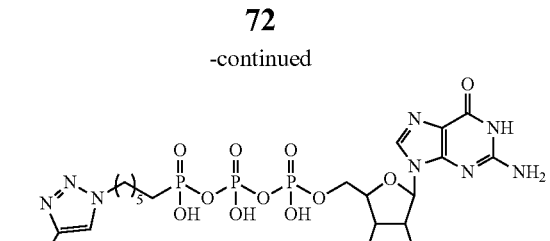

CLn$^{3+}$-27a, n = 0
CLn$^{3+}$-27b, n = 1
CLn$^{3+}$-27c, n = 2
CLn$^{3+}$-27d, n = 3
CLn$^{3+}$-27e, n = 4
CLn$^{3+}$-27f, n = 5
CLn$^{3+}$-27g, n = 6
CLn$^{3+}$-27h, n = 7

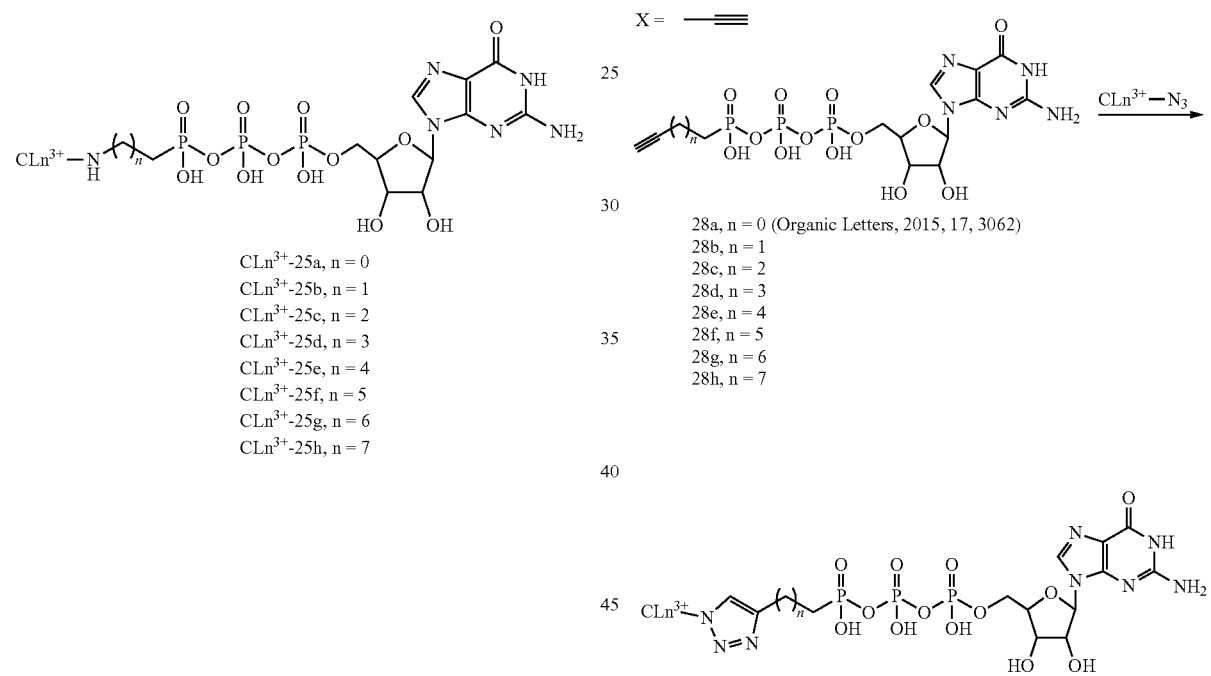

CLn$^{3+}$-25a, n = 0
CLn$^{3+}$-25b, n = 1
CLn$^{3+}$-25c, n = 2
CLn$^{3+}$-25d, n = 3
CLn$^{3+}$-25e, n = 4
CLn$^{3+}$-25f, n = 5
CLn$^{3+}$-25g, n = 6
CLn$^{3+}$-25h, n = 7

Scheme 13

28a, n = 0 (Organic Letters, 2015, 17, 3062)
28b, n = 1
28c, n = 2
28d, n = 3
28e, n = 4
28f, n = 5
28g, n = 6
28h, n = 7

CLn$^{3+}$-29a, n = 0
CLn$^{3+}$-29b, n = 1
CLn$^{3+}$-29c, n = 2
CLn$^{3+}$-29d, n = 3
CLn$^{3+}$-29e, n = 4
CLn$^{3+}$-29f, n = 5
CLn$^{3+}$-29g, n = 6
CLn$^{3+}$-29h, n = 7

Scheme 12

X = N$_3$

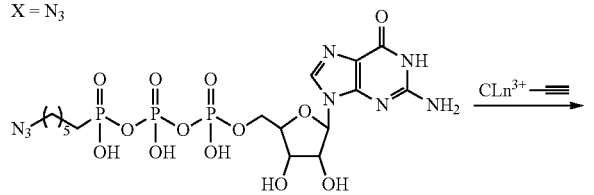

26a, n = 0
26b, n = 1
26c, n = 2
26d, n = 3
26e, n = 4
26f, n = 5 (Journal of Organic Chemistry, 2012, 77, 10450)
26g, n = 6
26h, n = 7

In the same way as for the GTPs, the analog GPPNHP (commercial, CAS: 64564-03-0) can be coupled with lanthanide complexes at the gamma position using the same synthesis strategies. For the derivatives substituted at gamma O, the synthesis is described, for example, in scheme 14. For the derivatives substituted at gamma N, the syntheses are described in schemes 15 and 16. These couplings have also been exemplified in the application WO 2009/068751, which uses ATP analogs.

Scheme 14
GPPNHPγO series (with protective group)
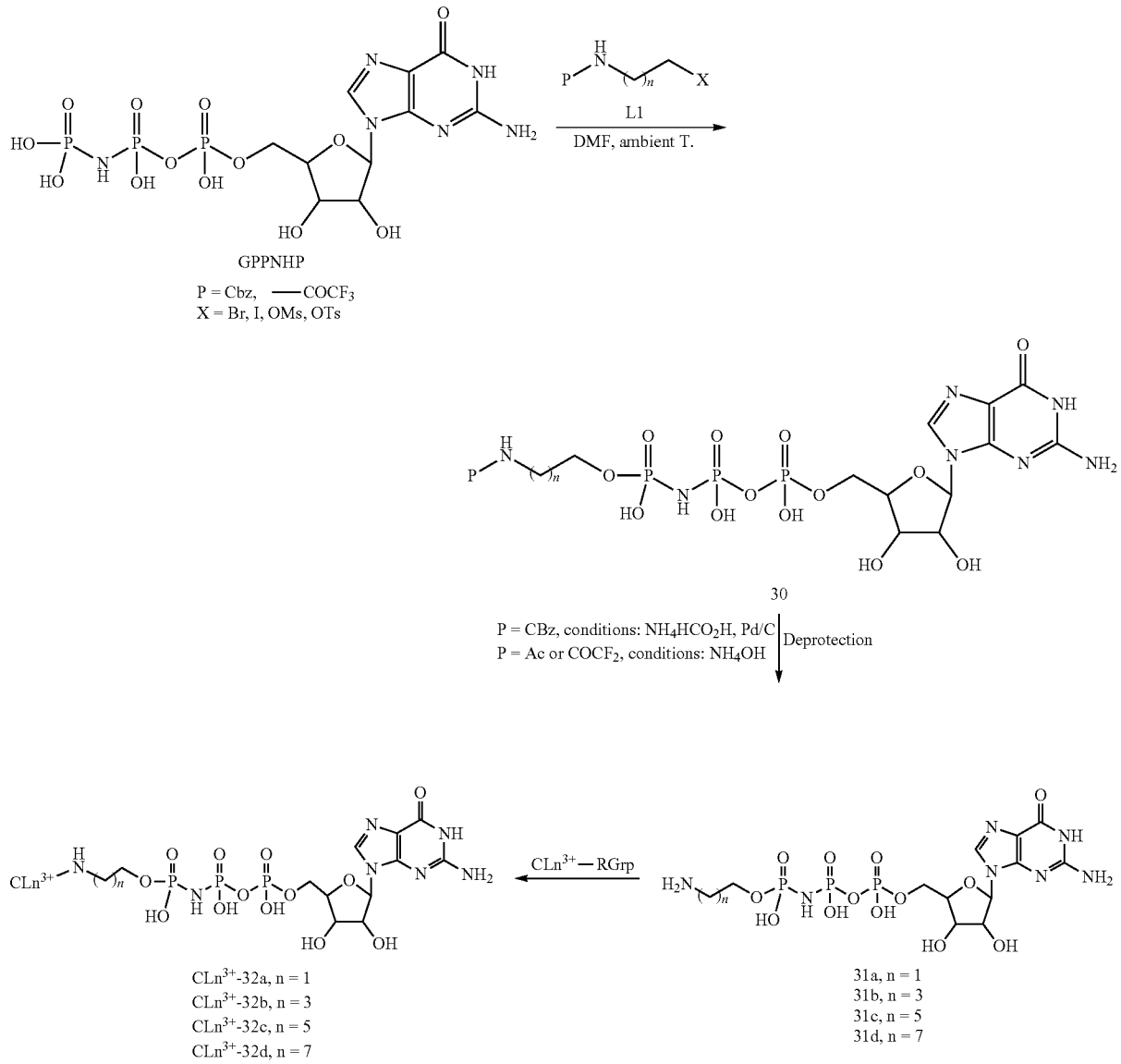
Scheme 15
GPPNHPγNH series (with protective group)
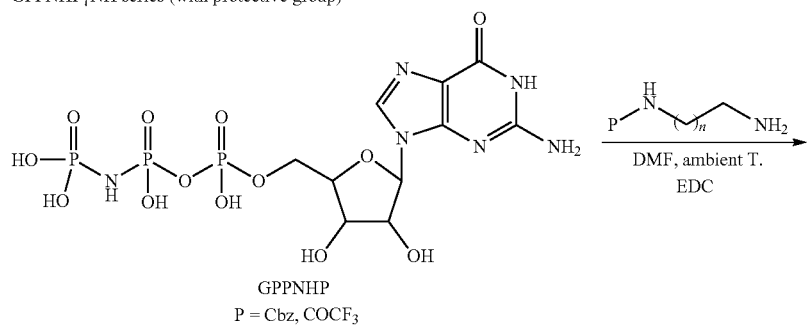

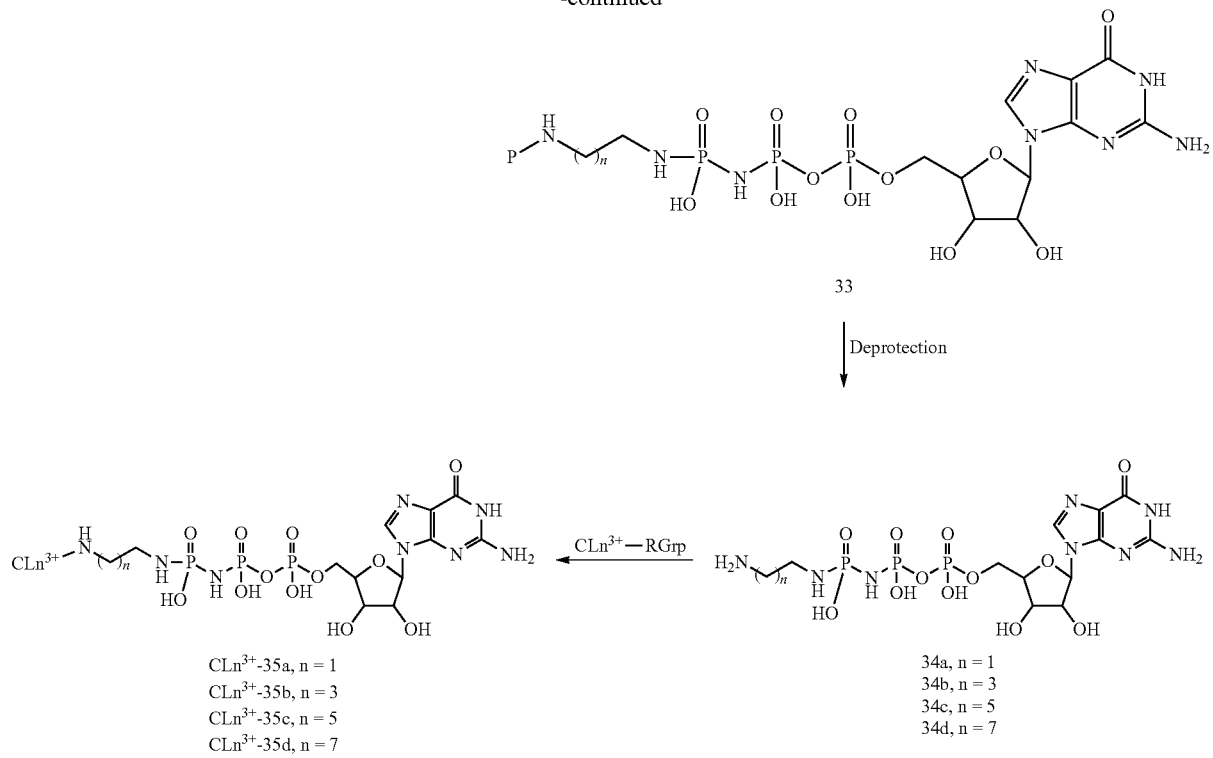

33

Deprotection

CLn³⁺-35a, n = 1
CLn³⁺-35b, n = 3
CLn³⁺-35c, n = 5
CLn³⁺-35d, n = 7

← CLn³⁺—RGrp 34a, n = 1
34b, n = 3
34c, n = 5
34d, n = 7

Scheme 16

Direct GPPNHPγN series

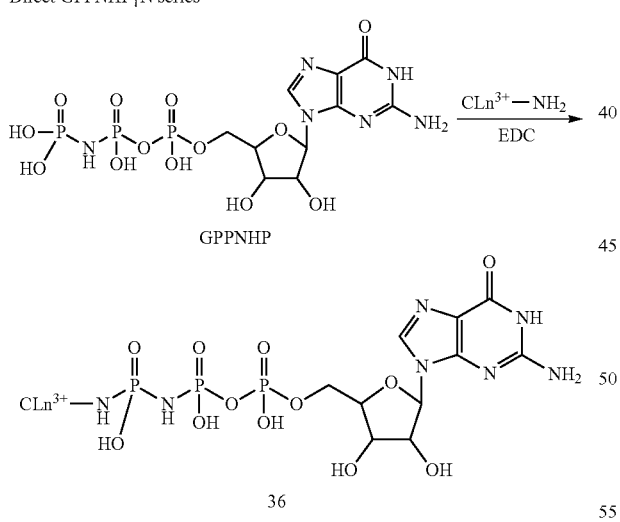

GPPNHP

36

In the same way as for the GTPs, the GPPCH₂P analog (commercial, CAS: 13912-93-1 or 10470-57-2 in the form of the Na salt) can be coupled with lanthanide complexes in the gamma position using the same synthesis strategies. For the derivatives substituted at gamma 0, the synthesis is described, for example, in scheme 17. For the derivatives substituted at gamma N, the syntheses are described in schemes 18 and 19. These couplings have also been exemplified in the application WO 2009/068751, which uses ATP analogs.

Scheme 17
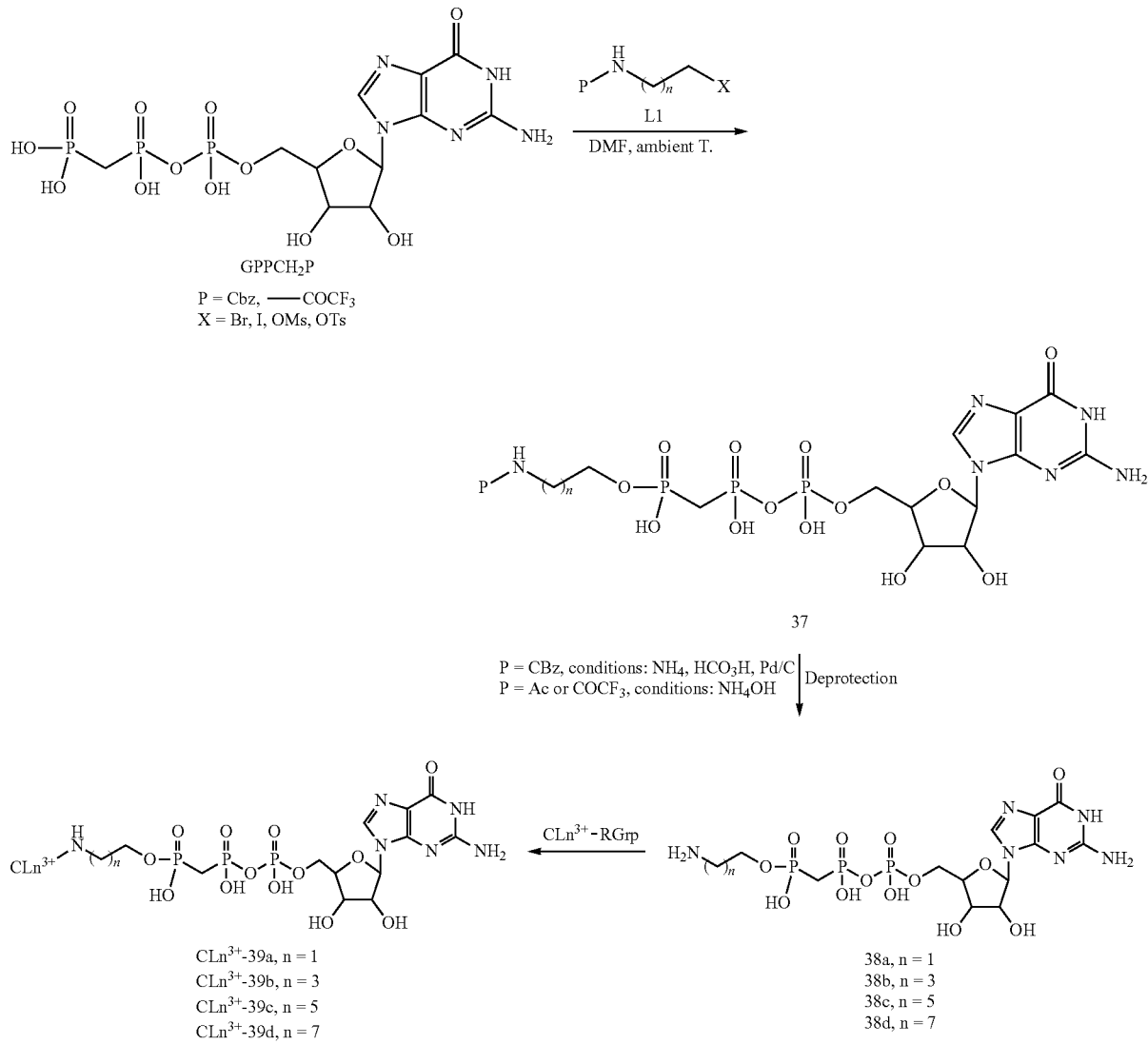
Scheme 18
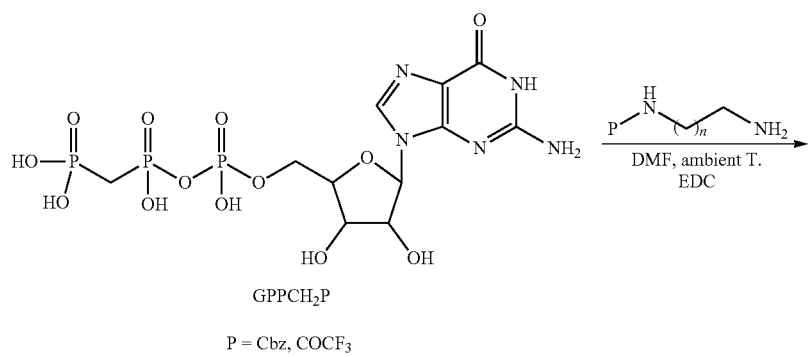

-continued

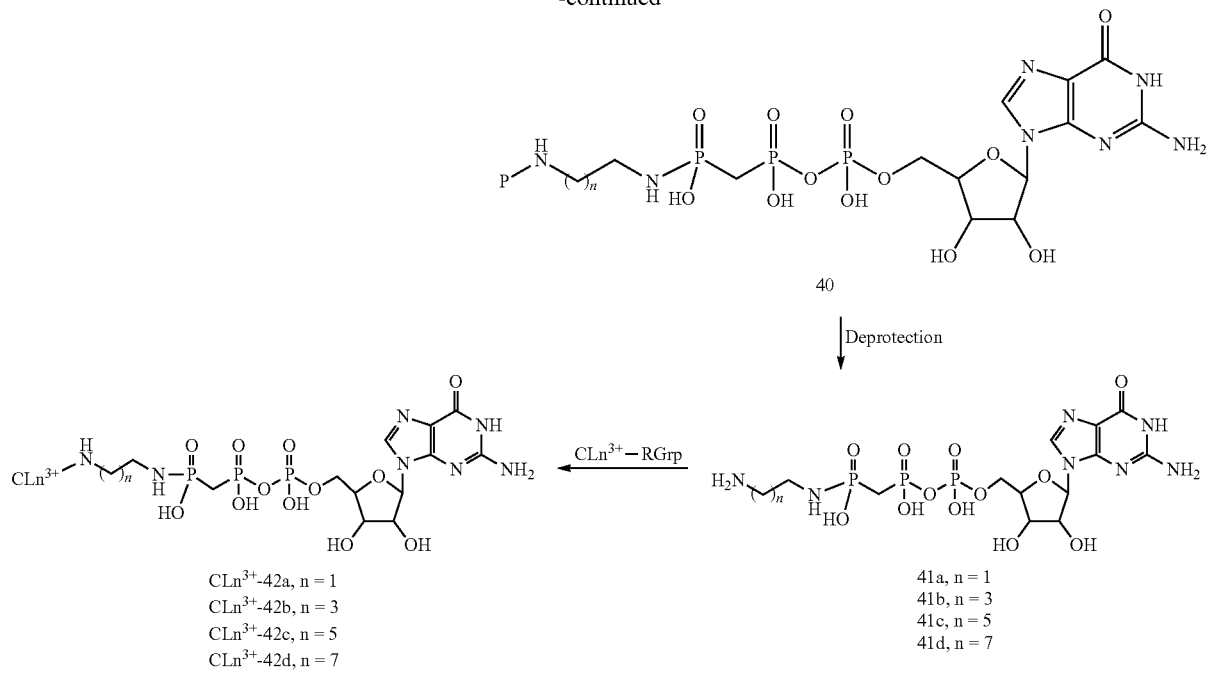

Scheme 19
Direct GPPCH₂PγN series

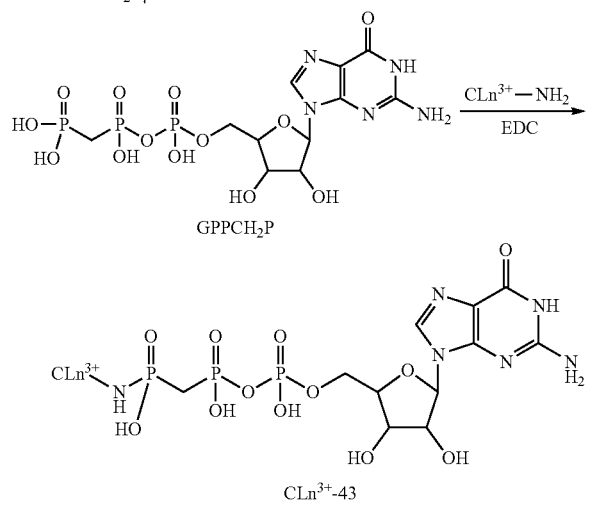

The invention is illustrated by the examples below, given by way of illustration.

Abbreviations Used
BRET: Bioluminescence Resonance Energy Transfer
BSA: Bovine Serum Albumin
DMSO: dimethyl sulfoxide
EDC: N-(3-dimethylaminopropyl)-N'-ethylcarbodiimide
eq: equivalent
ESI+: positive electrospray ionization mode
FRET: Forster Resonance Energy Transfer
GDP: guanosine diphosphate
GPCR: G protein-coupled receptors
GTP: guanosine triphosphate
GTPγS: guanosine 5'-[γ-thio]triphosphate
h: hour
HEPES: 4-(2-hydroxyethyl)-1-piperazineethanesulfonic acid
HPLC: high performance liquid chromatography
LC-MS: high performance liquid chromatography coupled with mass spectrometry
LRMS: low resolution mass spectrometry
MES: 2-(N-morpholino)ethanesulfonic acid
MOPS: 3-morpholino-1-propanesulfonic acid
NCS: isothiocyanate
NHS: N-hydroxysuccinimide
Py: pyridine
GPCR: G protein-coupled receptors
AT: ambient temperature
TEA: triethylamine
TRIS: trishydroxymethylaminomethane
UPLC: ultra high performance liquid chromatography
UPLC-MS: ultra high performance liquid chromatography coupled with mass spectrometry
UV: Ultraviolet Chromatography Analytical and preparative high performance liquid chromatography (HPLC) procedures were carried out on two appliances:

Analytical HPLC: ThermoScientific, P4000 quaternary pump, UV 1000 detector having a deuterium lamp (190-350 nm), Waters XBridge C₁₈, 3.5 μm, 4.6×100 mm, analytical column.

Preparative HPLC: Shimadzu, 2 LC-8A pumps, Varian ProStar diode array UV detector, Waters XBridge prep. C₁₈, 5 μm: 19×100 mm or 50×150 mm, preparative column.

Analytical ultra-high performance liquid chromatography (UPLC) procedures were carried out on a Waters Acquity HClass appliance with, as detector, either a PDA-type diode array UV detector or an SQD2-type single quadrupole mass detector. The probe used is an electrospray in positive mode: capillary voltage at 3.2 kV-cone voltage at 30 V.

Gradient A Waters Xbridge $C_{18}$, 5 µm, 10×100 mm, column, A/water 25 mM triethylammonium acetate pH 7-B/acetonitrile-t=0 to 5 min 1% B-t=10 min 10% B-20 ml·min$^{-1}$ at 260 nm.

Gradient B

Waters Xbridge $C_{18}$, 5 µm, 4.6×100 mm, column, A/water 25 mM triethylammonium acetate pH 7-B/acetonitrile-t=0 to 2 min 2% B-t=19 min 40% B-1 ml·min$^{-1}$.

Gradient C

Waters Xbridge $C_{18}$, 3.5 µm, 4.6×100 mm, column-A/water 5 mM ammonium acetate pH 5-B/acetonitrile t=0 min 2% B-t=1 min 2% B-t=15 min 40% B-1 ml·min$^{-1}$.

Gradient D

Waters Xbridge $C_{18}$, 5 µm, 19×100 mm, column-A/water 5 mM ammonium acetate pH 6.6-B/acetonitrile t=0 min 2% B-t=2.5 min 2% B-t=27 min 40% B-12 ml·min$^{-1}$ at 280 and 320 nm.

Gradient E

Waters Xbridge $C_{18}$, 5 µm, 19×100 mm, column-A/water 25 mM triethylammonium acetate pH 7-B/acetonitrile t=0 min 2% B-t=2 min 2% B-t=20 min 50% B-20 ml·min$^{-1}$ at 280 and 320 nm.

Gradient F

Waters Acquity $C_{18}$, 300 Å, 1.7 µm, 2.1×50 mm, column-A/water 5 mM ammonium acetate pH 5-B/acetonitrile t=0 min 2% B-t=0.2 min 2% B-t=5 min 40% B-0.6 ml·min$^{-1}$.

Gradient G

Waters Xbridge $C_{18}$, 300 Å, 5 µm, 10×100 mm, column-A/water 25 mM triethylammonium acetate-B/acetonitrile t=0 min 2% B-t=19 min 20% B-5 ml·min$^{-1}$.

Gradient H

Waters Xbridge $C_{18}$, 5 µm, 4.6×100 mm, column, A/water 25 mM triethylammonium acetate pH 7-B/acetonitrile-t=0 to 2 min 2% B-t=19 min 50% B-1 ml·min$^{-1}$.

Gradient I

Waters Xbridge $C_{18}$, 5 µm, 10×100 mm, column-A/water 25 mM triethylammonium acetate pH 7-B/acetonitrile t=0 min 2% B-t=2 min 2% B-t=27 min 50% B-3.5 ml·min$^{-1}$ at 280 nm.

Gradient J

Waters Xbridge $C_{18}$, 5 µm, 19×100 mm, column-A/water 25 mM triethylammonium acetate-B/acetonitrile t=0 min 5% B-t=17 min 45% B-20 ml·min$^{-1}$.

Gradient K

Waters Xbridge $C_{18}$, 300 Å, 5 µm, 10×100 mm, column-water 25 mM triethylammonium acetate-B/acetonitrile t=0 min 2% B-t=19 min 40% B-5 ml·min$^{-1}$.

Preparation of the Compounds

Preparation 1: GTP gamma-N-pentyl-NH$_2$ (9c)

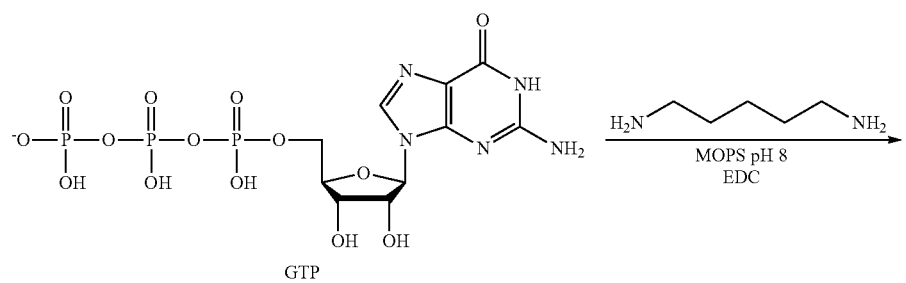

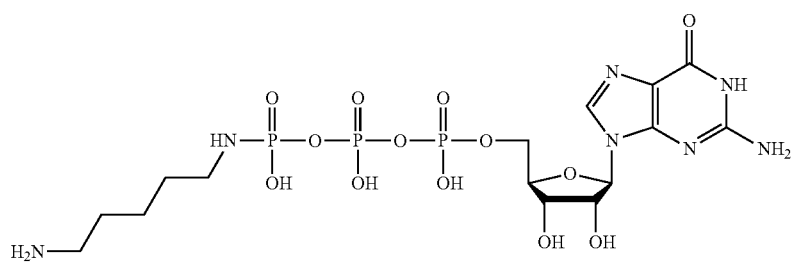

EDC (40 mg; 210 µmol, 11 eq) and a solution of cadaverine (58 mg, 573 µmol, 30 eq) in MOPS at pH 8 were added to a round-bottomed flask containing GTP (10 mg; 19.1 µmol, 1 eq) in solution in water (500 µl). The reaction mixture was stirred at AT overnight before being purified by preparative HPLC (Gradient A). A white solid was obtained corresponding to the compound 9c (5 mg). (ESI+): calculated $C_5H_{28}N_7O_{13}P_3[M+H]^+$, m/z=608.10, found 608.55.

Preparation 2: GTP gamma-O-hexyl-C2

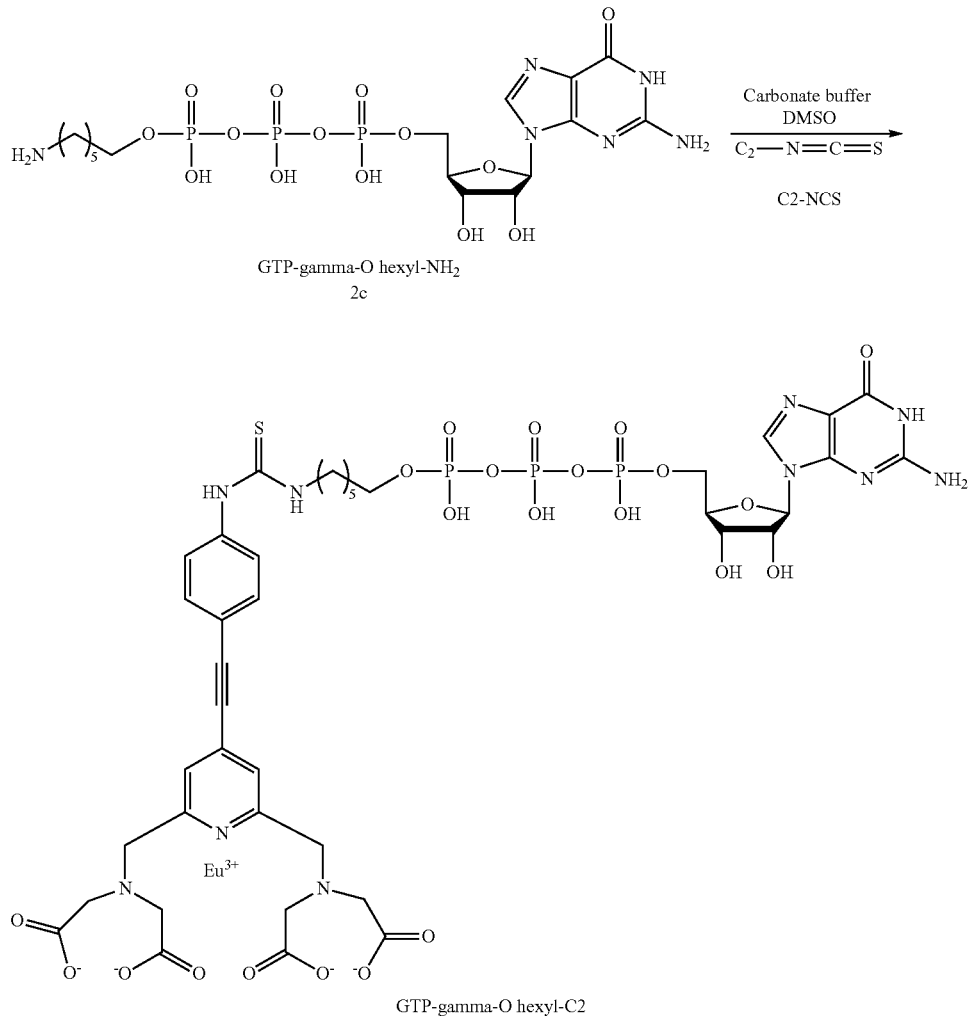

GTP-gamma-O hexyl-C2

Complex C2 functionalized in its NCS (isothiocyanate) form (473 µg, 700 nmol) in solution in DMSO (200 µl) was added all at once to a solution of compound 2c (0.454 mg, 700 nmol) in 100 mM carbonate buffer pH 9 (500 µl). The mixture was stirred at AT overnight. The progress of the reaction was monitored by HPLC (Gradient B) and UPLC-MS (Gradient C); after this period, the reaction was complete. The reaction mixture was directly purified by semi-preparative HPLC (Gradient D) to result in the compound GTP-gamma-O-hexyl-C2 (125 µg, 96 nmol, 14%) in the form of a white powder. LRMS (ESI+): calculated for $C_{40}H_{47}EuN_{10}O_{22}P_3S^-$ $[M+3H]^{2+}$, m/z=650.06, found 650.32.

Preparation 3: GTP gamma-O-hexyl-C3

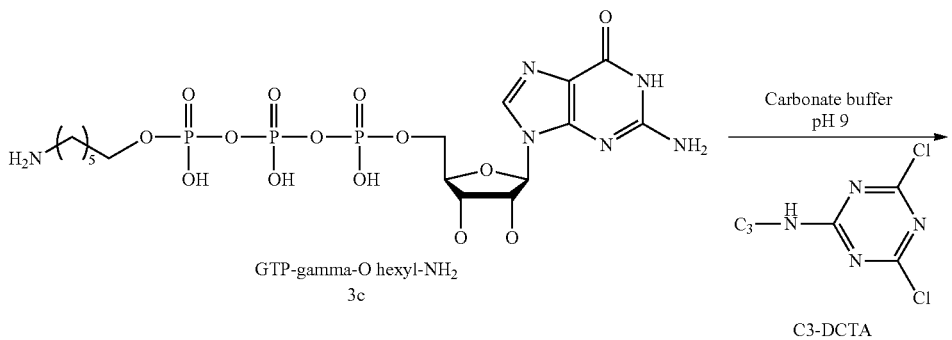

GTP-gamma-O hexyl-NH$_2$
3c

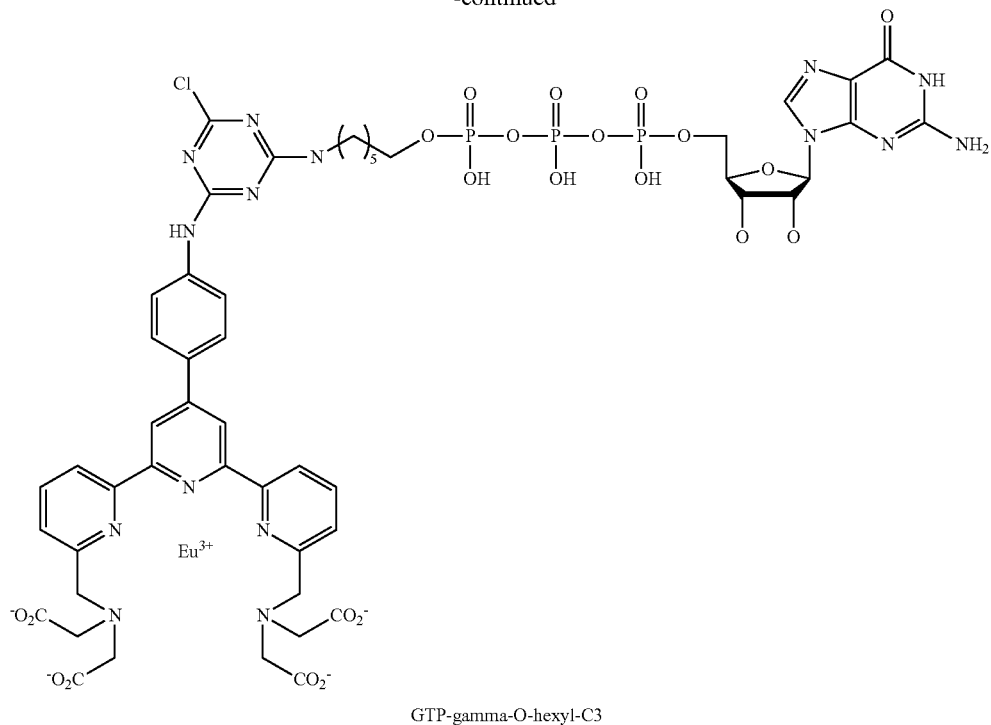

GTP-gamma-O-hexyl-C3

Complex C3 functionalized in its dichlorotriazine form (0.647 mg, 708 nmol) in solution in 100 mM carbonate buffer pH 9 (200 µl) was added all at once to a solution of compound 2c (0.442 mg, 710 nmol) in 100 mM carbonate buffer pH 9 (200 µl). The mixture was stirred at 4° C. overnight. The progress of the reaction was monitored by UPLC-MS (Gradient C); after this period, the reaction was complete. The reaction mixture was directly purified by preparative HPLC (Gradient E) to result in the compound GTP-gamma-O-hexyl-C3 (0.11 mg, 70 nmol, 10%) in the form of a white powder. LRMS (ESI+): calculated for $C_{50}H_{53}ClEuN_{15}O_{22}P_3^-$ $[M+3H]^{2+}$, m/z=749.59, found 750.29.

Preparation 4: GTP-gamma-N-C2

GTP +

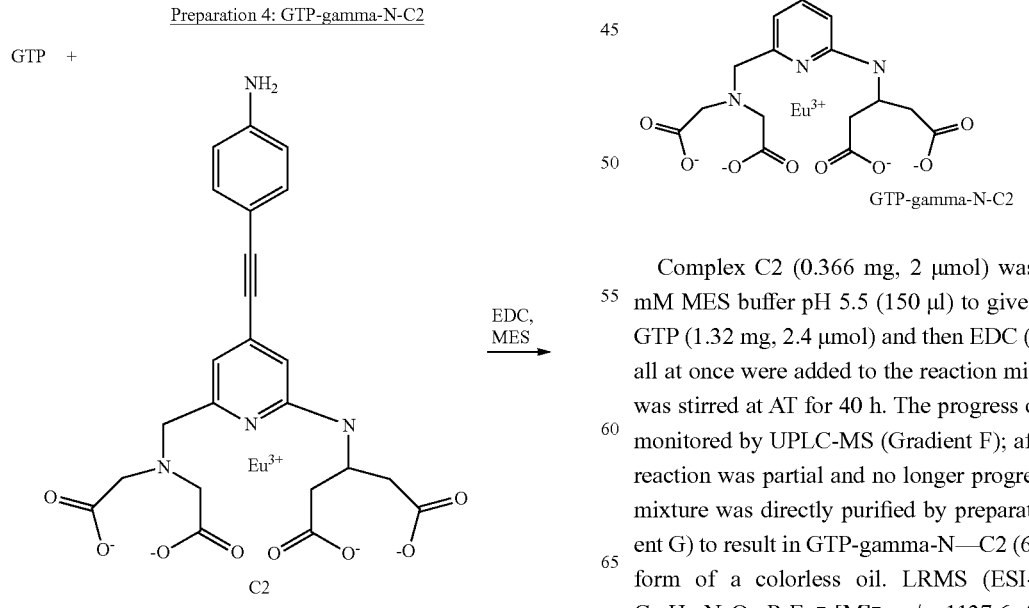

GTP-gamma-N-C2

Complex C2 (0.366 mg, 2 µmol) was dissolved in 500 mM MES buffer pH 5.5 (150 µl) to give a yellow solution. GTP (1.32 mg, 2.4 µmol) and then EDC (1.92 mg, 10 µmol) all at once were added to the reaction mixture. The mixture was stirred at AT for 40 h. The progress of the reaction was monitored by UPLC-MS (Gradient F); after this period, the reaction was partial and no longer progressed. The reaction mixture was directly purified by preparative HPLC (Gradient G) to result in GTP-gamma-N—C2 (60 nmol, 3%) in the form of a colorless oil. LRMS (ESI+): calculated for $C_{33}H_{34}N_9O_{21}P_3Eu^-$ $[M]^-$, m/z=1137.6, found 1138.2.

Preparation 5: GTP-gamma-N-C3

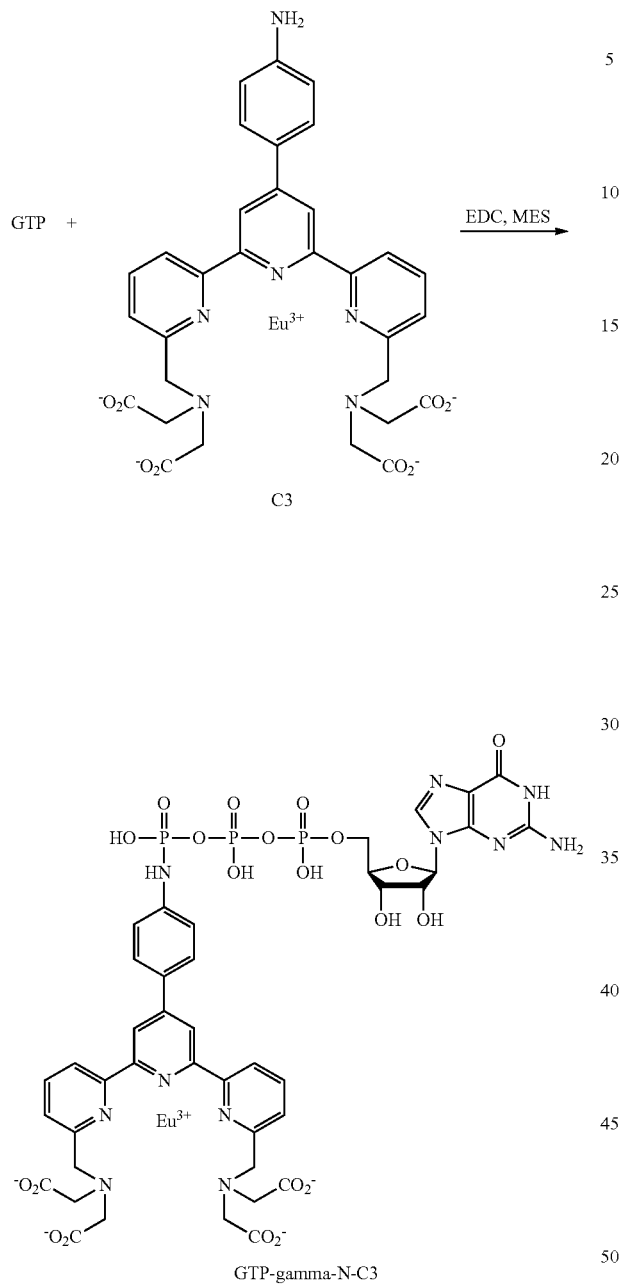

GTP-gamma-N-C3

Complex C3 (0.366 mg, 480 nmol) was dissolved in 500 mM MES buffer pH 5.5 (150 μl) to give a yellow solution. GTP (0.317 mg, 576 nmol) and then EDC (0.460 mg, 2.4 μmol) all at once were added to the reaction mixture. The mixture was stirred at AT overnight. The progress of the reaction was monitored by UPLC-MS (Gradient F); after this period, the reaction was partial and no longer progressed. The reaction mixture was directly purified by preparative HPLC (Gradient G) to result in GTP-gamma-N—C3 (45.6 nmol, 9.5%) in the form of a colorless oil. LRMS (ESI+): calculated for $C_{41}H_{40}N_{11}O_{21}P_3Eu^-$ [M+2H]$^+$, m/z=1269.7, found 1269.

Preparation 6: GTP-gamma-N-octyl-C2

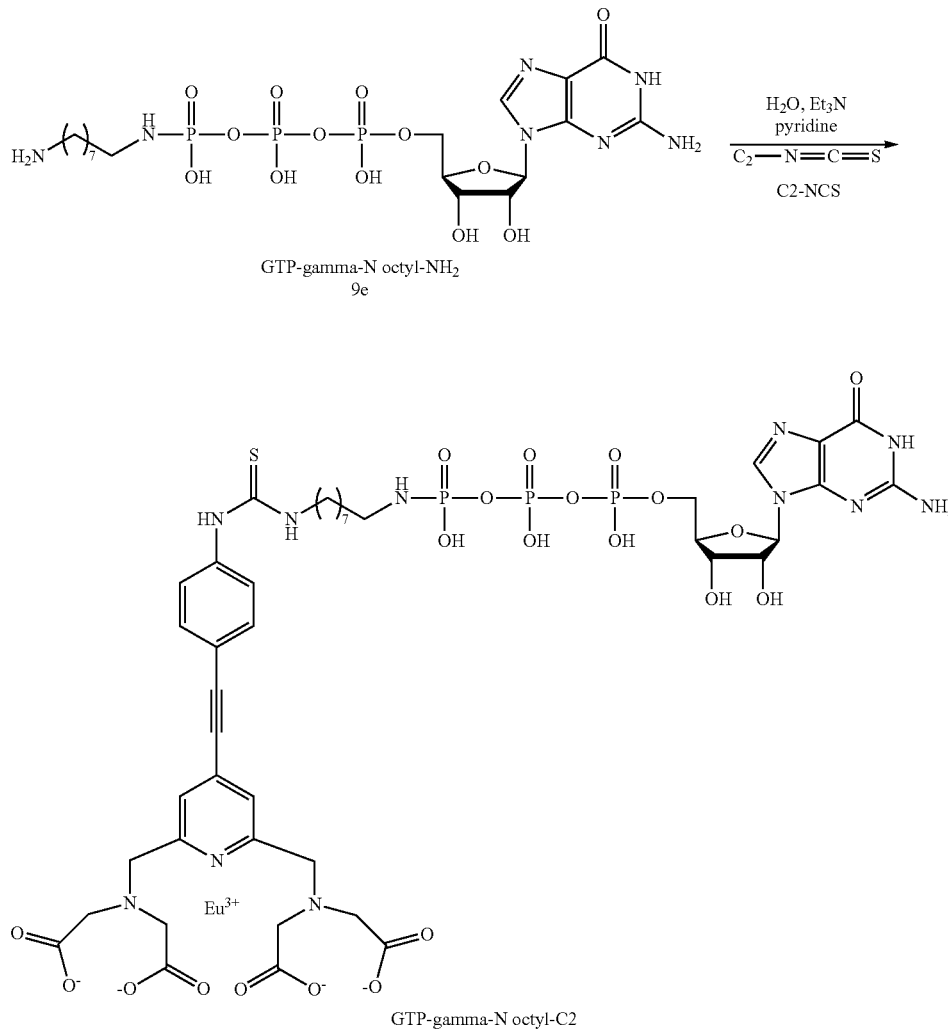

Compound 9e (50.0 µl, 500 nmol) was dissolved in water (100 µl). Pyridine (300 µl) and triethylamine (6 µl) were added to the reaction mixture. The reaction mixture was added to a tube containing complex C2 functionalized in its NCS (isothiocyanate) form (0.438 mg, 650 nmol) all at once. The mixture was stirred at 24° C. for 12 h. The progress of the reaction was monitored by UPLC-MS (Gradient F); after this period, the reaction was partial. The reaction mixture was directly purified by preparative HPLC (Gradient G) to result in GTP-gamma-N-octyl-C2 (16.9 nmol, 3.4%) in the form of a colorless oil. LRMS (ESI+): calculated for $C_{42}H_{52}N_{11}O_{21}P_3SEu^-$ $[M+3H]^{2+}$, m/z=663.5, found 663.9.

Preparation 7: GTP-gamma-N-octyl-C3

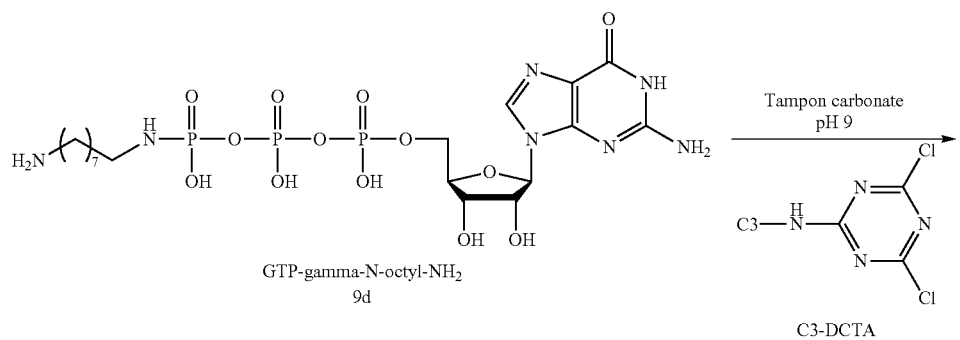

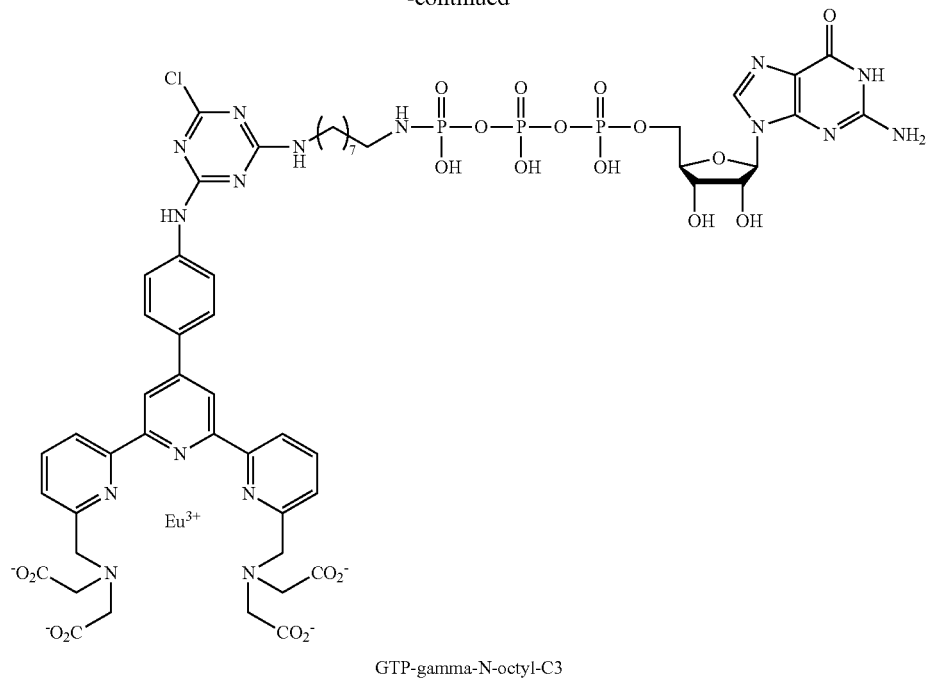

GTP-gamma-N-octyl-C3

Complex C3 functionalized in its dichlorotriazine form (400 µg, 438 nmol) in solution in water (200 µl) was added all at once to a solution of compound 9e (0.545 mg, 840 nmol) in 100 mM carbonate buffer pH 9 (500 µl). The mixture was stirred at 20° C. overnight. The progress of the reaction was monitored by HPLC (Gradient H) and UPLC-MS (Gradient C). After this period, the reaction was complete. The reaction mixture was directly purified by semi-preparative HPLC (Gradient 1) to result in the compound GTP-gamma-N-octyl-C3 (7.6 µg, 5 nmol, 1%) in the form of a white powder. LRMS (ESI+): calculated for $C_{52}H_{58}ClEuN_{16}O_{21}P_3^-$ $[M+3H]^{2+}$, m/z=763.11, found 763.29.

Preparation 8: GTP-gamma-N-hexyl-C11

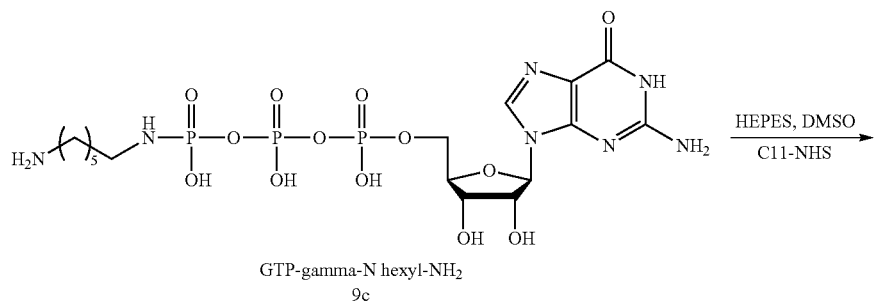

GTP-gamma-N hexyl-$NH_2$
9c

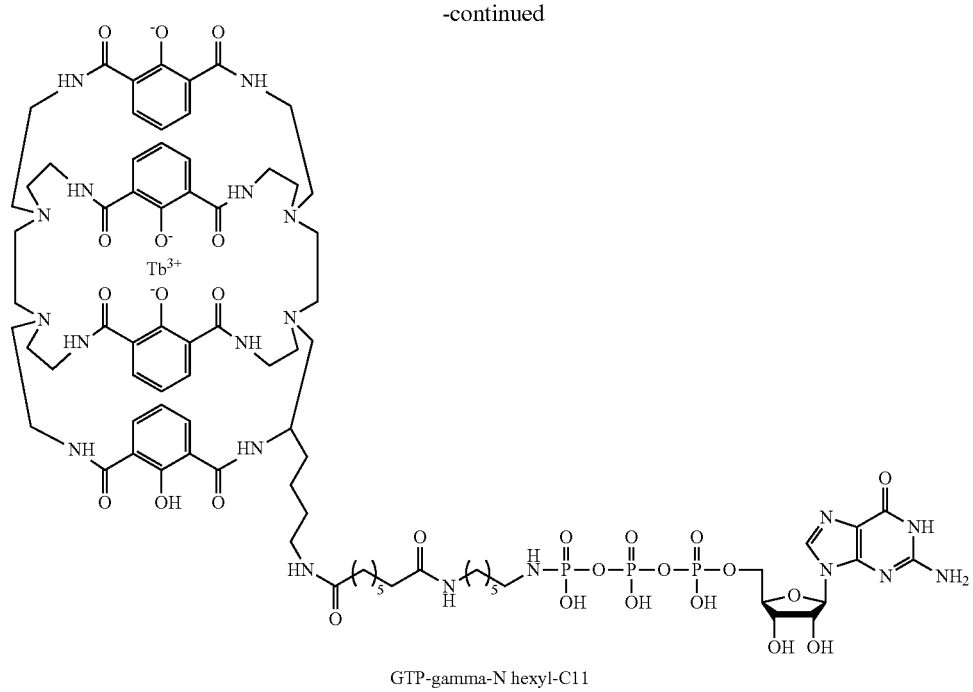

GTP-gamma-N hexyl-C11

Complex C11 functionalized in the NHS ester form (1.47 mg, 1 µmol) in solution in anhydrous DMSO (122 µl) was added all at once to a solution of compound 9d (0.62 mg, 1 µmol) in 50 mM HEPES buffer pH 8 (900 µl). The mixture was stirred at 24° C. for 1 h. The progress of the reaction was monitored by UPLC-MS (Gradient F); after this period, the reaction was complete. The reaction mixture was directly purified by preparative HPLC (Gradient J) to result in the compound GTP-gamma-N-hexyl-C11 (0.52 mg, 258 nmol, 26%) in the form of a white powder. LRMS (ESI+): calculated for $C_{80}H_{109}N_{20}O_{27}P_3Tb^{3+}$ $[M-H]^{2+}$, m/z=1018.9, found 1019.6, $[M+2Na^+-3H]^{2+}$, m/z=1040.8, found 1041.6.

Preparation 9: GTP-gamma-N-octyl-C11

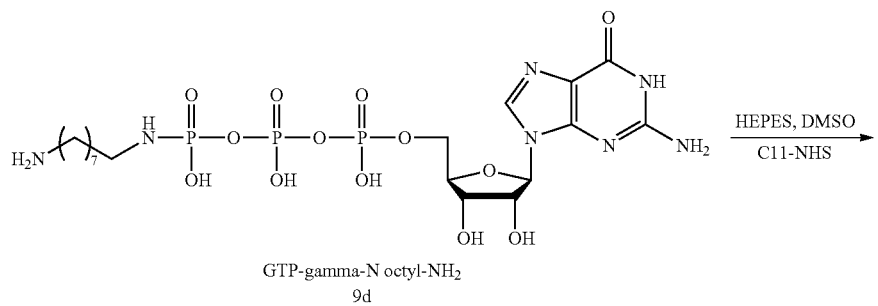

GTP-gamma-N octyl-NH$_2$
9d

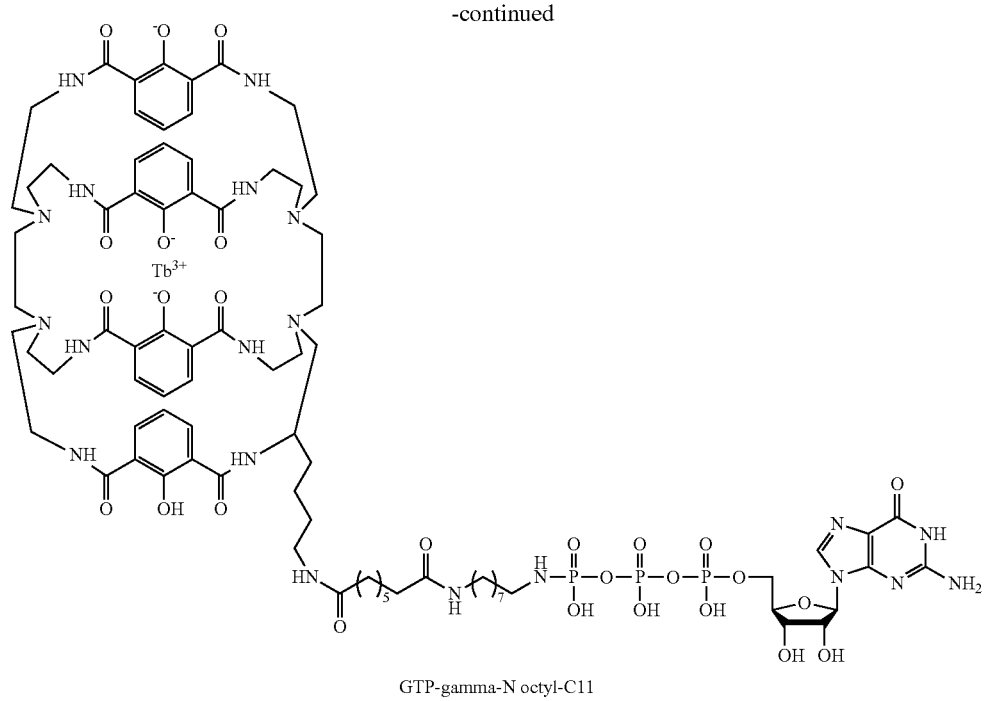

GTP-gamma-N octyl-C11

Complex C11 functionalized in the NHS ester form (0.76 mg, 500 nmol) in solution in anhydrous DMSO (102 µl) was added all at once to a solution of compound 9e (0.32 mg, 500 nmol) in 50 mM HEPES buffer pH 8 (300 µl). The mixture was stirred at 24° C. for 1 h. The progress of the reaction was monitored by UPLC-MS (Gradient F); after this period, the reaction was complete. The reaction mixture was directly purified by preparative HPLC (Gradient K) to result in the compound GTP-gamma-N-octyl-C11 (0.22 mg, 105 nmol, 21%) in the form of a white powder. LRMS (ESI+): calculated for $C_{82}H_{117}N_{20}O_{27}P_3Tb^{3+}$ $[M-2H]^+$, m/z=2064.8, found 2064.1.

Preparation 10: GTP-gamma-N-octyl-thiosuccinimdyl-C2

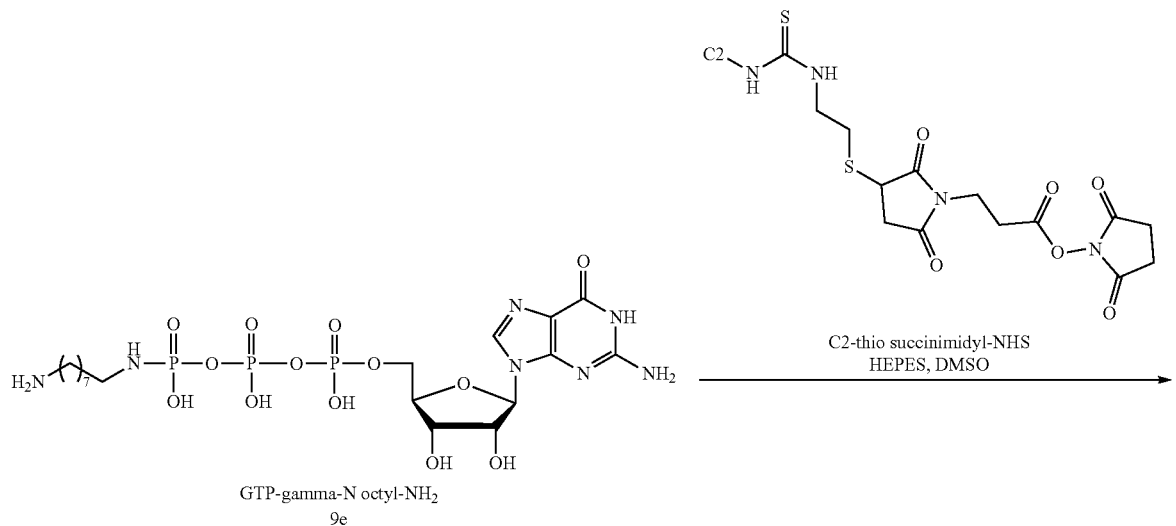

GTP-gamma-N octyl-NH₂
9e

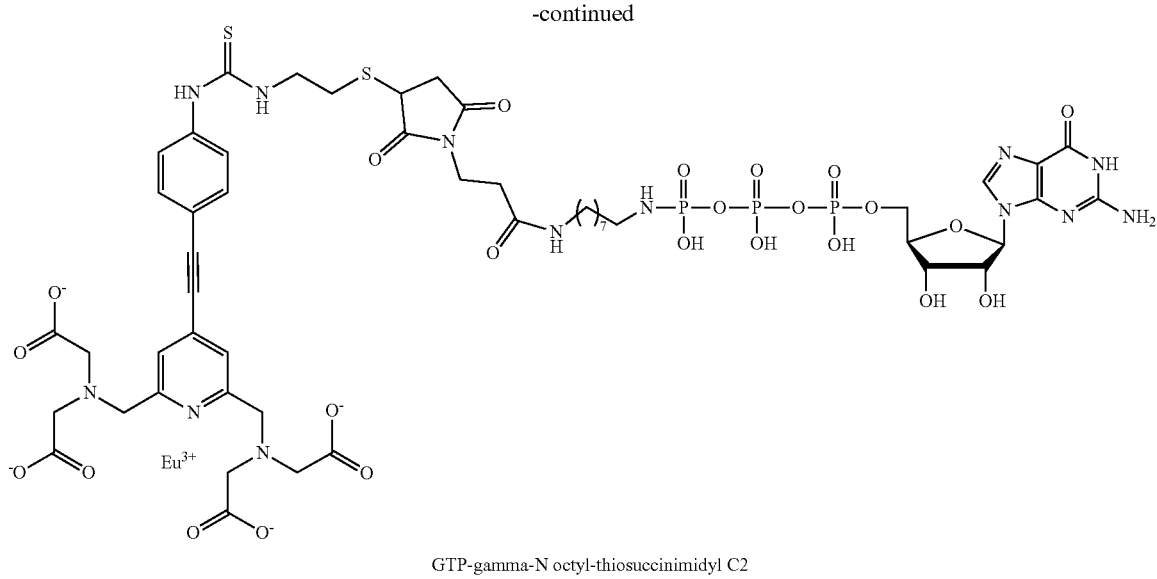

GTP-gamma-N octyl-thiosuccinimidyl C2

Compound 9e (0.649 mg, 1 µmol) in solution in water (100 µl) was diluted in 50 mM HEPES buffer pH 8 (757 µl) to give a colorless solution. Complex C2 functionalized in its NHS form (N-hydroxysuccinimide ester) (750 µl, 1 µmol) in solution in anhydrous DMSO (143 µl) was added to the reaction mixture in one go. The reaction was stirred at 25° C. for 1 h. The progress of the reaction was monitored by UPLC-MS (Gradient B). After this period, the reaction was not complete. Despite this, the reaction mixture was purified twice by preparative HPLC (Gradient E). The fractions corresponding to the expected product were collected and then concentrated under reduced pressure to result in the compound GTP-gamma-N-octyl-thiosuccinimidyl-C2 (0.241 µmol, 24%) in the form of a colorless solution. LRMS (ESI+): calculated for $C_{51}H_{68}EuN_{13}O_{24}P_3S_2^+$ [M+H]$^+$, m/z=1555.8, found 1555.8.

Binding Tests
Materials
   membrane preparations of cells expressing GPCRs and the G-alpha-i protein (Gαi) were purchased from Perkin Elmer or Euroscreen. The table below lists the cell backgrounds and references of the different samples used:

TABLE 1

| | Cell background | Provider | Reference |
|---|---|---|---|
| Delta Opioid | HEK293 | Perkin Elmer | 6110549400UA |
| Delta Opioid | CHO-K1 | Euroscreen | Service |
| Dopamine D2S | CHO-K1 | Euroscreen | Service | the DSV36 antibody was generated by Cisbio Bioassays and is available rom Cisbio Bioassays on request (under the reference DSV36S). The antibody was labeled with the fluorescent probe d2 (red acceptor) compatible for TR-FRET detection. The DSV36S antibody binds at the switch II of the Gαi protein.

the GTP and GTPγS nucleotides were purchased from Sigma Aldrich (respective catalog references G8877 and G8634).

the 384-well, low volume, white plates with a white background were purchased from Greiner Bio One (catalog reference 784075).

the non-hydrolyzable/slowly hydrolyzable GTP analogs labeled with donor fluorophores of lanthanide complex type were synthesized at Cisbio Bioassays.

Methods

Preparation of the Reagents

Except for other specific mention, all the reagents were diluted in 50 mM Tris HCl pH 7.4, 10 mM MgCl$_2$, 0.1% BSA, 10 mM NaCl, buffer. The membranes were prepared 4× to distribute 1 or 10 µg/well (amount specified in the key of each figure). The GTPγS nucleotide (non-specific signal condition) was prepared 6.67× to obtain a final concentration in the wells of 100 µM. The anti-Gαi antibody DSV36S-d2 used for the detection was prepared 4× to target the final concentration in the wells of 10 nM. The non-hydrolyzable/slowly hydrolyzable GTP analogs labeled with fluorescent donor probes (lanthanide complexes) were prepared 4× to target the final concentrations in the wells mentioned in the keys of each figure.

Distribution of the Reagents in the 384-Well Plates:
   Membranes expressing GPCR and the G protein: 5 µl
   GTPγS buffer or nucleotide (for the non-specific signal condition): 3 µl
   Non-hydrolyzable/slowly hydrolyzable GTP analog-donor: 5 µl
   Anti-Gαi antibody-acceptor (DSV36S-d2): 5 µl
   Buffer: 2 µl The non-specific signal (background fluorescence noise) was measured with wells containing an excess of GTPγS (10 or 100 µM).

Reading the HTRF Signal

The plates were incubated at 21° C. for 20 h and then the HTRF signal was measured on the PHERAstar reader (BMG Labtech) with the following configuration:
   Module: HTRF (Excitation 337 nm, Emission 665 nm and 620 nm)
   Excitation: laser, 40 flashes or lamp, 100 flashes
   Reading window: delays: 60 µs-Integration: 400 ρs Signal Processing From the raw signals at 665 nm and 620 nm, the HTRF Ratio was calculated according to the following formula:

HTRF Ratio=[(Signal at 665 nm)/(Signal at 620 nm)]×10 000

Test Format

Figure 2:
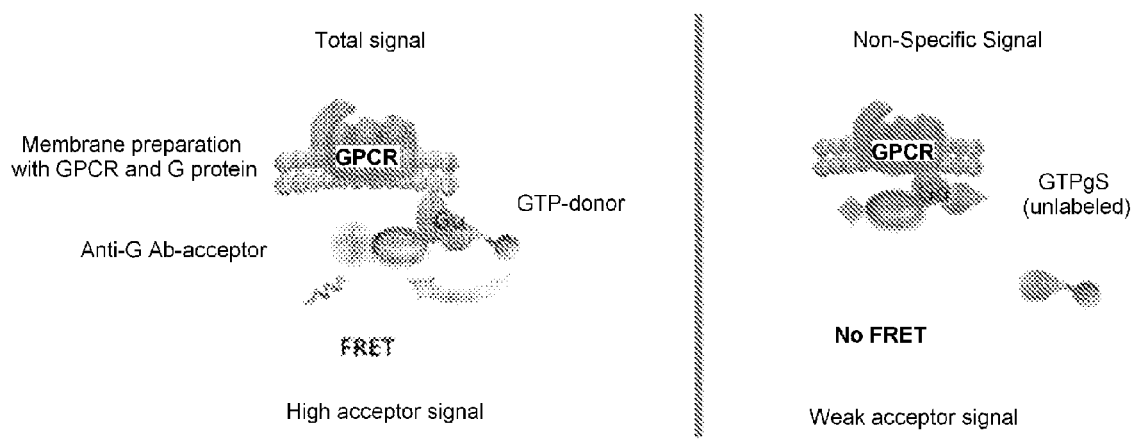
FIG. 2 illustrates the assay format used to detect the binding of the compounds of the invention to the G protein.

FIG. 2 illustrates the test format used to detect the binding of the compounds of formula (I) to the G protein. A membrane preparation comprising GPCRs and Gαi proteins was incubated in the presence of the test compounds and of an anti-Gα protein antibody labeled with an acceptor fluorophore, in the presence or absence of a non-hydrolyzable or slowly hydrolyzable GTP analog (typically, GTPγS). When the two FRET partners (test compound and anti-Gα protein antibody) bind to the same Gα protein, a FRET signal appears (left part of the figure: "Total Signal") and is distinguished from the non-specific signal (background noise corresponding to the right part of the figure: "Non-Specific Signal"), which comprises a large excess of unlabeled GTPγS (displacement of the fluorescent GTP analog).

Example 1—GTPgN—C2 Analog Binding Test

Figure 3:
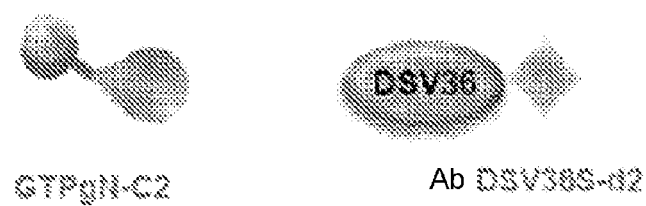
FIG. 3 illustrates a test for binding a compound of the invention to the Gαi protein.

The ability of the GTPgN—C2 (preparation 2)/anti-Gαi antibody DSV36S-d2 pair to generate a specific TR-FRET signal by binding to the G protein was demonstrated using membrane preparations of CHO-K1 cells expressing the Delta Opioid GPCR and the Gαi protein (10 μg per well). GTPgN—C2 was used at a final concentration of 6 nM in the wells. The membranes were incubated in the absence or in the presence of a large excess of GTPγS (100 μM). The difference in TR-FRET signal (HTRF Ratio total signal/non-specific signal=16.6) observed between these two conditions shows that the GTPgN—C2 analog is capable of binding to the Gαi protein and generating a TR-FRET signal with an anti-Gαi antibody-acceptor (FIG. 3).

Example 2—GTPgN—C3 Analog Binding Test

Figure 4:
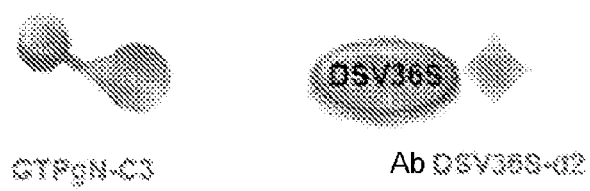
FIG. 4 illustrates a test for binding a compound of the invention to the Gαi protein.

The ability of the GTPgN—C3 (preparation 5)/anti-Gαi antibody DSV36S-d2 pair to generate a specific TR-FRET signal by binding to the G protein was demonstrated using membrane preparations of HEK293 cells expressing the Delta Opioid GPCR and the Gαi protein (1 μg per well). GTPgN—C3 was used at a final concentration of 1 nM in the wells. The membranes were incubated in the absence or in the presence of a large excess of GTPγS (100 μM). The difference in TR-FRET signal (HTRF Ratio total signal/non-specific signal=1.7) observed between these two conditions shows that the GTPgN—C3 analog is capable of binding to the Gαi protein and generating a TR-FRET signal with an anti-Gα antibody-acceptor (FIG. 4).

Example 3—GTPgN-octyl-C2 Analog Binding Test

Figure 5:
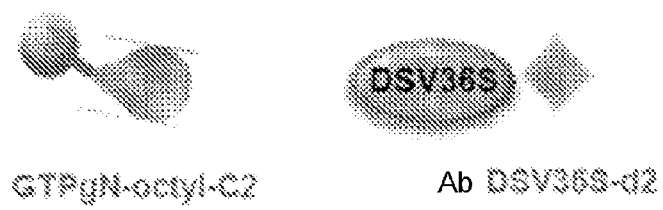
FIG. 5 illustrates a test for binding a compound of the invention to the Gαi protein.
Figure 5:
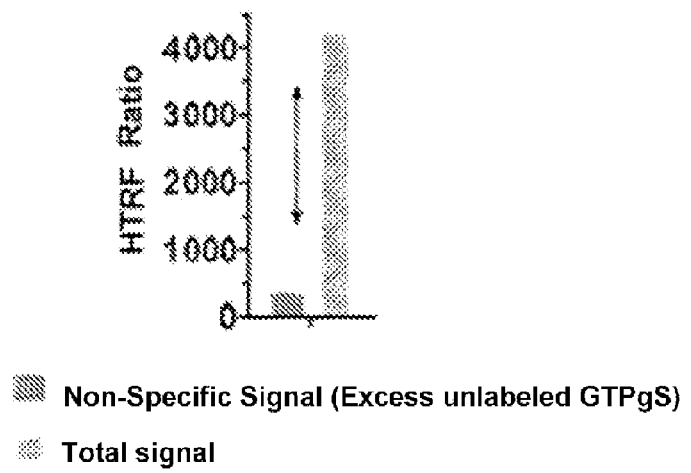

The ability of the GTPgN-octyl-C2 (preparation 6)/anti-Gαi antibody DSV36S-d2 pair to generate a specific TR-FRET signal by binding to the G protein was demonstrated using membrane preparations of CHO-K1 cells expressing the Delta Opioid GPCR and the Gαi protein (10 μg per well). GTPgN-octyl-C2 was used at a final concentration of 6 nM in the wells. The membranes were incubated in the absence or in the presence of a large excess of GTPγS (100 μM). The difference in TR-FRET signal (HTRF Ratio total signal/non-specific signal=12.4) observed between these two conditions shows that the GTPgN-octyl-C2 analog is capable of binding to the Gαi protein and generating a TR-FRET signal with an anti-Gαi antibody-acceptor (FIG. 5).

Example 4—GTPgN-octyl-C11 Analog Binding Test

Figure 6:
FIG. 6 illustrates a test for binding a compound of the invention to the Gαi protein.
Figure 6:
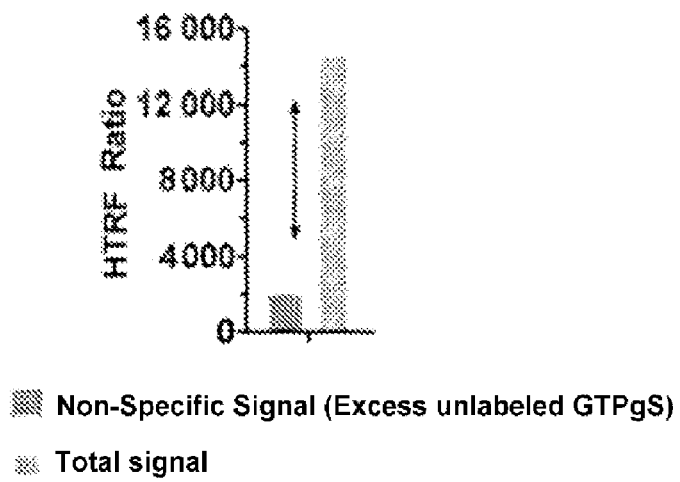

The ability of the GTPgN-octyl-C11 (preparation 9)/anti-Gαi antibody DSV36S-d2 pair to generate a specific TR-FRET signal by binding to the G protein was demonstrated using membrane preparations of CHO-K1 cells expressing the Delta Opioid GPCR and the Gαi protein (10 μg per well). GTPgN-octyl-C11 was used at a final concentration of 6 nM in the wells. The membranes were incubated in the absence or in the presence of a large excess of GTPγS (100 μM). The difference in TR-FRET signal (HTRF Ratio total signal/non-specific signal=7.6) observed between these two conditions shows that the GTPgN-octyl-C11 analog is capable of binding to the Gαi protein and generating a TR-FRET signal with an anti-Gαi antibody-acceptor (FIG. 6).

Example 5—GTPgN-octyl-C3 Analog Binding Test

Figure 7:
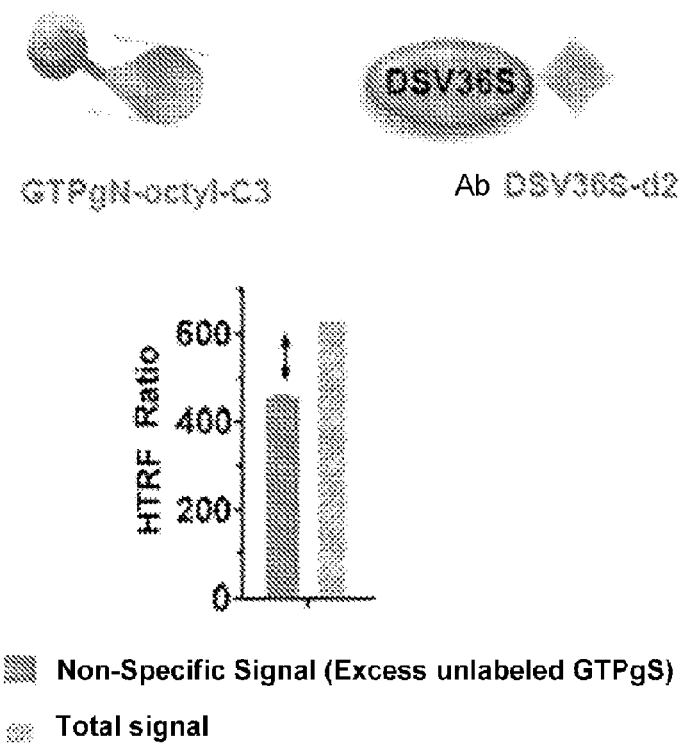
FIG. 7 illustrates a test for binding a compound of the invention to the Gαi protein.

The ability of the GTPgN-octyl-C3 (preparation 7)/anti-Gαi antibody DSV36S-d2 pair to generate a specific TR-FRET signal by binding to the G protein was demonstrated using membrane preparations of HEK293 cells expressing the Delta Opioid GPCR and the Gαi protein (1 μg per well). GTPgN-octyl-C3 was used at a final concentration of 1 nM in the wells. The membranes were incubated in the absence or in the presence of a large excess of GTPγS (100 μM). The difference in TR-FRET signal (HTRF Ratio total signal/non-specific signal=1.4) observed between these two conditions shows that the GTPgN-octyl-C3 analog is capable of binding to the Gαi protein and generating a TR-FRET signal with an anti-Gαi antibody-acceptor (FIG. 7).

Example 6—GTPgO-hexyl-C2 Analog Binding Test

Figure 8:
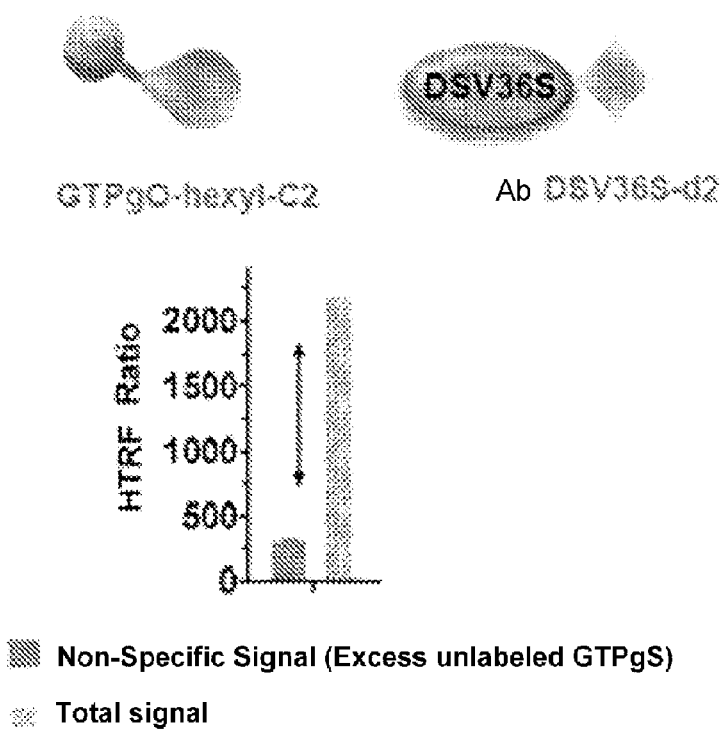
FIG. 8 illustrates a test for binding a compound of the invention to the Gαi protein.

The ability of the GTPgO-hexyl-C2 (preparation 2)/anti-Gαi antibody DSV36S-d2 pair to generate a specific TR-FRET signal by binding to the G protein was demonstrated using membrane preparations of CHO-K1 cells expressing the Delta Opioid GPCR and the Gαi protein (10 μg per well). GTPgO-hexyl-C2 was used at a final concentration of 6 nM in the wells. The membranes were incubated in the absence or in the presence of a large excess of GTPγS (100 μM). The difference in TR-FRET signal (HTRF Ratio total signal/non-specific signal=7.1) observed between these two conditions shows that the GTPgO-hexyl-C2 analog is capable of binding to the Gαi protein and generating a TR-FRET signal with an anti-Gαi antibody-acceptor (FIG. 8).

Example 7—GTPgO-hexyl-C3 Analog Binding Test

Figure 9:
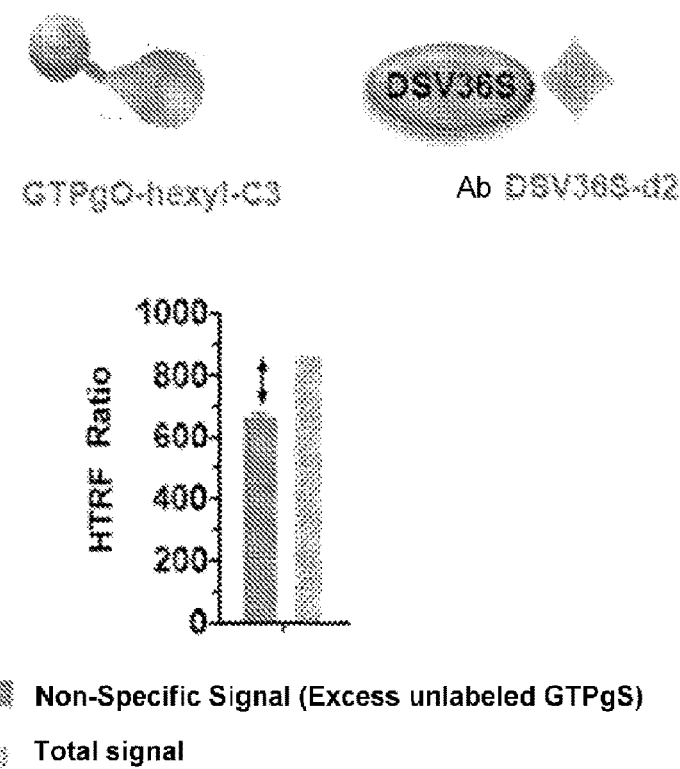
FIG. 9 illustrates a test for binding a compound of the invention to the Gαi protein.

The ability of the GTPgO-hexyl-C3 (preparation 3)/anti-Gαi antibody DSV36S-d2 pair to generate a specific TR-FRET signal by binding to the G protein was demonstrated using membrane preparations of HEK293 cells expressing the Delta Opioid GPCR and the Gαi protein (1 μg per well). GTPgO-hexyl-C3 was used at a final concentration of 1 nM in the wells. The membranes were incubated in the absence or in the presence of a large excess of GTPγS (100 μM). The difference in TR-FRET signal (HTRF Ratio total signal/non-specific signal=1.3) observed between these two conditions shows that the GTPgO-hexyl-C3 analog is capable of binding to the Gαi protein and generating a TR-FRET signal with an anti-Gαi antibody-acceptor (FIG. 9).

Example 8—GTPgN-octyl-C2 Analog Binding Test

Figure 10:
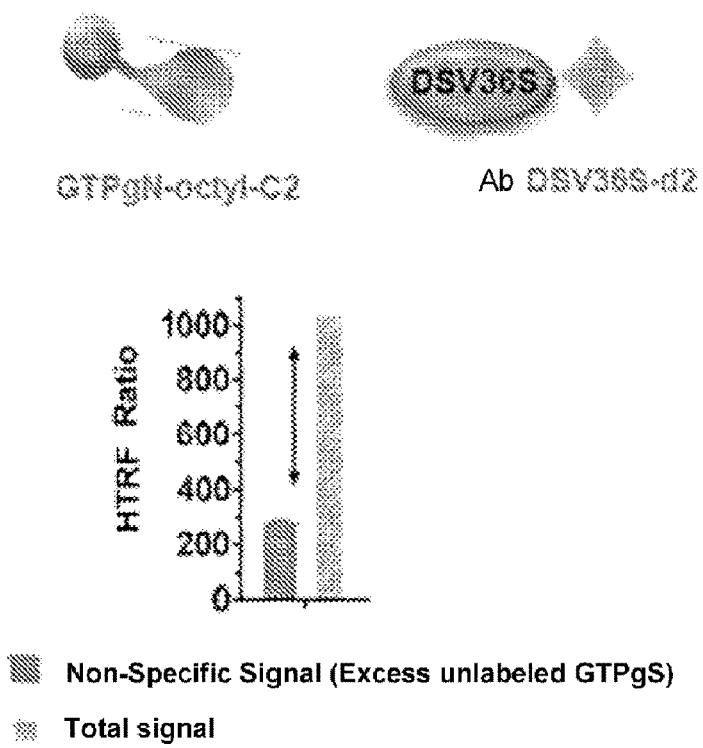
FIG. 10 illustrates a test for binding a compound of the invention to the Gαi protein.

The ability of the GTPgN-octyl-C2 (preparation 6)/anti-Gαi antibody DSV36S-d2 pair to generate a specific TR-FRET signal by binding to the G protein was demonstrated using membrane preparations of CHO-K1 cells expressing the Dopamine D2S GPCR and the Gαi protein (10 µg per well). GTPgN-octyl-C2 was used at a final concentration of 6 nM in the wells. The membranes were incubated in the absence or in the presence of a large excess of GTPγS (100 µM). The difference in TR-FRET signal (HTRF Ratio total signal/non-specific signal=3.8) observed between these two conditions shows that the GTPgN-octyl-C2 analog is capable of binding to the Gαi protein and generating a TR-FRET signal with an anti-Gαi antibody-acceptor (FIG. 10).

Example 9—Effect of the Concentration of Membranes and of GTP Analog-Lanthanide on the GTPgN-octyl-C2 Analog Binding Test The ability of the GTPgN-octyl-C2 (preparation 6)/anti-Gαi antibody DSV36S-d2 pair to generate a specific TR-FRET signal by binding to the G protein was demonstrated using membrane preparations of CHO-K1 cells expressing the Delta Opioid GPCR and the Gαi protein (1 or 10 µg/well). GTPgN-octyl-C2 was used at a final concentration of 2 or 6 nM in the wells. The membranes were incubated in the absence or in the presence of a large excess of GTPγS (100 µM). The difference in TR-FRET signal (HTRF Ratio total signal (S)/non-specific signal (N)) observed between these two conditions shows that the GTPgN-octyl-C2 analog is capable of binding to the Gαi protein and generating a TR-FRET signal with an anti-Gαi antibody-acceptor (FIGS. 11A and 11B). Moreover, it emerges from FIG. 11A that an increase in the signal amplitude (S/N) is observed by increasing the amount of membrane from 1 to 10 µg per well. It emerges from FIG. 11B that an increase in the amplitude of the signal (S/N) is observed by increasing the concentration of GTPgN-octyl-C2 from 2 to 6 nM.

Example 10—GTPgN-octyl-thiosuccinimidyl-C2 Analog Binding Test

The ability of the GTPgN-octyl-thiosuccinimidyl-C2 (preparation 10)/anti-Gαi antibody DSV36S-d2 pair to generate a specific TR-FRET signal by binding to the G protein was demonstrated using membrane preparations of CHO-K1 cells expressing the Delta Opioid GPCR and the Gαi protein (10 µg per well). The reagents were diluted in 50 mM Tris HCl buffer pH 7.4, 60 mM $MgCl_2$, 0.1% BSA, 150 mM NaCl. GTPgN-octyl-thiosuccinimidyl-C2 was used at a final concentration of 7.5 nM in the wells. The fluorescent conjugates were incubated in the absence or in the presence of membrane preparation. The difference in TR-FRET signal (HTRF Ratio total signal/non-specific signal=2.8) observed between these two conditions shows that the GTPgN-octyl-thiosuccinimidyl-C2 analog is capable of binding to the Gαi protein and generating a TR-FRET signal with an anti-Gαi antibody-acceptor (FIG. 12).

The invention claimed is:
1. A compound which is:

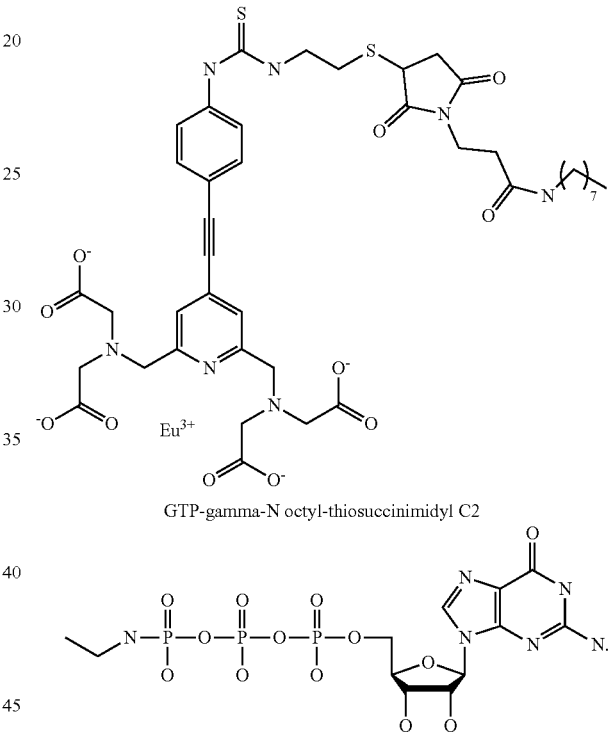

GTP-gamma-N octyl-thiosuccinimidyl C2